United States Patent [19]
Boyer, Jr. et al.

[11] Patent Number: 6,046,355
[45] Date of Patent: Apr. 4, 2000

[54] DIHYDROPYRONES WITH IMPROVED ANTIVIRAL ACTIVITY

[75] Inventors: Frederick Earl Boyer, Jr., Canton Township; John Michael Domagala, Canton; Edmund Lee Ellsworth, Brighton; Christopher Andrew Gajda, Ann Arbor; Susan Elizabeth Hagen, Canton Township; Harriet Wall Hamilton, Chelsea; Elizabeth Ann Lunney, Ann Arbor; Larry James Markoski, Ypsilanti; Josyula Venkata Nagendra Vara Prasad, Ann Arbor; Bradley Dean Tait, Canton, all of Mich.

[73] Assignee: Warner-Lambert Company, Morris Plains, N.J.

[21] Appl. No.: 09/124,190

[22] Filed: Jul. 28, 1998

Related U.S. Application Data

[62] Division of application No. 08/883,743, Jun. 27, 1997, Pat. No. 5,834,506
[60] Provisional application No. 60/029,906, Nov. 1, 1996.
[51] Int. Cl.[7] .................................................. C07D 309/31
[52] U.S. Cl. .......................... 562/91; 544/383; 548/323.5; 560/12; 556/428; 558/387
[58] Field of Search ............................... 560/12; 558/387; 562/430, 91; 556/428; 544/383; 548/323.5

[56] References Cited

PUBLICATIONS

H. Skulnick et al., "Structure–Based Design of Nonpeptidic HIV Protease Inhibitors: The Sulfonamide–Substituted Cyclooctylpyranones" *J. Med. Chem.*, 1997, 40:7, 1149–1164.

K. Romines et al., "Cycloalkylpyranones and Cycloalkylpyrones as HIV Protease Inhibitors: Exploring the Impact of Ring Size on Structure–Activity Relationships", *J. Med. Chem.*, 1996, 39:20, 4125–4130.

S. Thaisrivongs et al., "Structure–Based Design of HIV Protease Inhibitors: 5,6–Dihydro–4–hydroxy–2–pyrones as Effective, Nonpeptidic Inhibitors", *J. Med. Chem.*, 1996, 39:23, 4630–4642.

S. Thaisrivongs et al., "Structure–Based Design of HIV Protease Inhibitors: 5,6–Dihydro–4–hydroxy–2–pyrones as Non–Peptidic Inhibitors", *J. Med. Chem.*, 1996, 39:22, 4349–4353.

T. Judge et al., "Asymmetric Syntheses and Absolute Stereochemistry of 5,6–Dihydro–α–pyrones, A New Class of Potent HIV Protease Inhibitors", *J. Am. Chem. Soc.*, 1997, 119:15, 3627–3628.

*Primary Examiner*—Amelia Owens
*Attorney, Agent, or Firm*—Elizabeth M. Anderson

[57] ABSTRACT

This invention pertains to improved antiviral activity of 6,6-disubstituted-5,6-dihydropyran-2-ones caused by judicious placement of certain polar substituents at the 3 and/or 6 positions.

The same substituents which enhance the cellular activity also diminish cytotoxicity further enhancing the desirable properties of these agents as antivirals.

1 Claim, No Drawings

DIHYDROPYRONES WITH IMPROVED ANTIVIRAL ACTIVITY

This application is a divisional of 08/883,743 filed Jun. 27, 1997 now U.S. Pat. No. 5,834,506 and is related to provisional application 60/029,906 filed Nov. 1, 1996.

INTRODUCTION

Certain 6,6-disubstituted-3-thio-4-hydroxy-5,6-dihydro-2H-pyran-2-ones have been prepared in co-pending U.S. application Ser. No. 08/319,820 and references therein. All of these compounds were designed to have potent activity vs the HIV protease enzyme and on that basis to be potent antivirals for the treatment of Acquired Immunodeficiency Disease Syndrome (AIDS).

It is well known in the art that other factors may influence the level of actual antiviral activity in cells causing less cellular antiviral activity than expected based on the HIV protease inhibition. Such factors may include instability of the compound in the cellular media, the inability of the agent to enter the cells, binding of the agent to plasma related proteins or cellular proteins, etc. Likewise, some agents may be cytotoxic to the cells themselves thus diminishing their antiviral activity. These are all problems that all antiviral agents must eventually overcome.

SUMMARY OF THE INVENTION

The present invention relates to the extraordinary discovery by the inventors that certain polar substituents judiciously placed at the 3 and/or 6 positions of the 6,6-disubstituted-5,6-dihydropyrones can dramatically enhance cellular activity, and thus greatly improve the antiviral properties of such substituted agents. The same substituents which enhance the cellular activity also diminish cytotoxicity further enhancing the desirable properties of these agents as antivirals.

The selectively substituted 5,6-dihydropyrones are expected to be extremely useful in the development of treatments for infections caused by viruses, especially by retroviruses that rely on aspartyl protease activities for replication and infectivity. One such retrovirus is HIV. For this reason, the antiviral 5,6-dihydropyrones are also expected to be very useful in the treatment of diseases and syndromes associated with viral pathogens. One such syndrome is AIDS.

The present invention relates to compounds or pharmaceutically acceptable salts thereof of formula I, shown below:

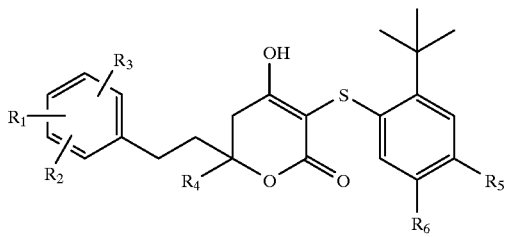

I wherein:

$R_1$ is H, 2- or 3- or 4- $(CH_2)_{n'}OR'$ or $(CH_2)_{n'}N(R')_2$ where n' is 0 or 1 and wherein 2- or 3- or 4- refer to the point of substitution on the phenyl ring;

$R_2$ and $R_3$ are independently H, OR, $N(R)_2$, a straight or branched alkyl of 1–4 carbons, a cycloalkyl of 3–6 carbons, F, Cl, Br, NRCOR, COR, $CON(R)_2$, OCOR, $CO_2R$, $NRSO_2R$, $SO_2N(R)_2$, $NRSO_3R$, $NRSO_2N(R)_2$, $NRCON(R)_2$, or $R_2$ and $R_3$ may be taken together to form a ring of 5–6 atoms optionally containing 1 or 2 heteroatoms;

$R_4$ is a straight or branched alkyl of 1–7 carbons, a cycloalkyl of 3–7 carbons, a heterocycle of 4–7 atoms containing 1–2 heteroatoms, or $(CH_2)_nPh$, all of which may be optionally substituted by F, Cl, Br, R, OR, SR, $N(R)_2$, $CON(R)_2$, NRCOR, $SO_2R$ and COR;

$R_5$ is H, $(CH_2)_nOR$, $(CH_2)_nN(R)_2$, $(CH_2)_nNRCOR$, $(CH_2)_nOSO_2N(R)_2$, $(CH_2)_nOSO_2R$, $(CH_2)_nNRSO_2N(R)_2$, $OCH_2CH_2OR$, $NRCH_2CH_2(CH_2)_nCN$, $(CH_2)_nCON(R)_2$, $(CH_2)_nNRCON(R)_2$, $C(CH_3)_2OR$, $(CH_2)_nCOR$, $(CH_2)_nNRSO_2R$, $(CH_2)_nCO_2R$, $O(CH_2)_{n''}CO_2R$, $OCON(R)_2$, $NR(CH_2)_nCO_2R$, $-(CH_2)_n-NR-CS-N(R)_2$, $(CH_2)_n-NRSO_2OR$, wherein n is an integer of from 0 to 3;

R6 is methyl, ethyl or isopropyl;

R is independently H, a straight or branched alkyl of 1–5 carbons, a $-(CH_2)_n$-cycloalkyl wherein the cycloalkyl is of 3–6 carbons and wherein n is an integer of from 0 to 3, $-(CH_2)_m$-Ph, a $(CH_2)_m$-heterocycle wherein the heterocycle is of 5–6 atoms with 1–3 heteroatoms and wherein m is an integer of from 0 to 3, and wherein the $(R)_2$ in $N(R)_2$ may be a heterocycle containing the nitrogen, all optionally substituted by F, Cl, Br, =O (the =O represents a ketone), -CN, -$CF_3$, OR', COR', $N(R')_2$, $CON(R')_2$, or NR'COR';

R' is H, a straight or branched alkyl of 1–3 carbons, or Ph; and n" is an integer of from 1–2.

A compound which upon administering to a human being converts into a compound according to formula I is within the scope of this invention.

Preferred compounds of formula I are those wherein:

$R_1$ is H, 2- or 3- or 4-$(CH_2)_{n'}OH$ or $(CH_2)_{n'}NH_2$ where n' is 0 or 1;

$R_2$ and $R_3$ are independently H, an alkyl of 1–3 carbons, F, Cl Br, or $R_2$ and $R_3$ may be taken together to form a 5 membered ring optionally containing one or two heteroatoms;

$R_4$ is a straight or branched alkyl of 1–7 carbons, a cycloalkyl of 3–7 carbons, a heterocycle of 4–7 atoms containing 1–2 heteroatoms, or $(CH_2)_nPh$, all of which may be optionally substituted by F, Cl, Br, R, OR, SR, $N(R)_2$, $CON(R)_2$, NRCOR, $SO_2R$ and COR;

$R_5$ is H, $(CH_2)_nOR$, $(CH_2)_nN(R)_2$, $(CH_2)_nNRCOR$, $(CH_2)_nOSO_2N(R)_2$, $(CH_2)_nOSO_2R$, $(CH_2)_nNRSO_2N(R)_2$, $OCH_2CH_2OR$, $NRCH_2CH_2OR$, $(CH_2)_nCN$, $(CH_2)_nCON(R)_2$, $(CH_2)_nNRCON(R)_2$, $C(CH_3)_2OR$, $(CH_2)_nCOR$, $(CH_2)_nNRSO_2R$, $(CH_2)_nCO_2R$, $O(CH_2)_nCO_2R$, $OCON(R)_2$, $NR(CH_2)_nCO_2R$, $-(CH_2)_n-NR-CS-N(R)_2$, $(CH_2)_n-NRSO_2OR$, wherein n is an integer of from 0 to 2, and n" is an integer of from 1 to 2;

R6 is $CH_3$;

R is independently H, a straight or branched alkyl of 1–5 carbons, a $-(CH_2)_m$-cycloalkyl wherein the cycloalkyl is of 3–6 carbons and wherein m is an integer of from 0 to 3, $-(CH2)_m-$, Ph, a $(CH_2)_m$-heterocycle wherein the heterocycle is of 5–6 atoms with 1–3 heteroatoms and wherein m is an integer of from 0 to 3, and wherein the $(R)_2$ in $N(R)_2$ may be a heterocycle containing the nitrogen, all optionally substituted by F, Cl, Br, -CN, -$CF_3$, OR', COH, $N(R')_2$, $CON(R')_2$, NR'COR'; and R' is H, a straight or branched alkyl of 1–3 carbons, or Ph; n is 0–2 and n" is 1–2.

More preferred compounds of formula I are those wherein:

$R_1$ is H, 3- or 4-$(CH_2)_{n'}OH$ or $(CH_2)_{n'}NH_2$ where n' is 0 or 1;
$R_2$ and $R_3$ are independently H, an alkyl of 1–3 carbons, F, Cl or Br;
$R_4$ is a straight or branched alkyl of 1–5 carbons, a cycloalkyl of 3–6 carbons, a heterocycle of 5–6 carbons containing one heteroatom or Ph, all of which may be optionally substituted by OR, $N(R)_2$, $SO_2R$, and COR;
$R_5$ is H, $(CH_2)_nOR$, $(CH_2)_nN(R)_2$, $(CH_2)_nNRCOR$, $(CH_2)_nOSO_2N(R)_2$, $(CH_2)_nOSO_2R$, $(CH_2)_nNRSO_2N(R)_2$, $OCH_2CH_2OR$, $NRCH_2CH_2OR$, $(CH_2)_nCN$, $(CH_2)_nCON(R)_2$, $(CH_2)_nNRCON(R)_2$, $C(CH_3)_2OR$, $(CH_2)_nCOR$, $(CH_2)_nNRSO_2R$, $(CH_2)_nCO_2R$, $O(CH_2)_{n''}CO_2R$, $OCON(R)_2$, $NR(CH_2)_nCO_2R$, $—(CH_2)_n—NR—CS—N(R)_2$, $(CH_2)_n—NRSO_2OR$;
n is an integer of from 0 to 2;
$R_6$ is $CH_3$;
R is independently H, a straight or branched alkyl of 1–5 carbons, a $—(CH_2)_m$-cycloalkyl wherein the cycloalkyl is of 3–6 carbons and wherein m is an integer of from 0 to 3, $—(CH_2)_m$-Ph, a $(CH_2)_m$-heterocycle wherein the heterocycle is of 5–6 atoms with 1–3 heteroatoms and wherein m is an integer of from 0 to 3, and wherein the $(R)_2$ in $N(R)_2$ may be a heterocycle containing the nitrogen, all optionally substituted by F, Cl, Br, —CN, —CF_3, OR', COH, $N(R')_2$, $CON(R')_2$, or NR'COR'; and
R' is H, a straight or branched alkyl of 1–3 carbons, or Ph;
n is 0–2 and n" is 1–2.

More preferred compounds of formula I are those wherein:
$R_1$ is H;
$R_2$ and $R_3$ are H;
$R_4$ is Ph or pyridinyl optionally substituted by OR, SR, $N(R)_2$, $CON(R)_2$, NRCOR, $SO_2R$, or COR;
$R_5$ is H, $CH_2OH$, $OCH_2CH_2OH$, OH, or $NH_2$;
$R_6$ is $CH_3$;
R is a $(CH_2)_m$ heterocycle of 5–6 atoms with 1–2 heteroatoms optionally substituted by OR', $N(R')_2$, $CON(R')_2$, or NR'COR';
m is an integer of from 2 to 3; and
R' is H, a straight or branched alkyl of 1–3 carbons, or Ph;
n is 0–2 and n" is 1–2.

Most preferred compounds are those wherein:
$R_1$ is 3- or 4-$(CH_2)_{n'}OH$ or a $(CH_2)_{n'}NH_2$ where n' is 0 or 1;
$R_2$ and $R_3$ are independently H, an alkyl of 1–3 carbons, F, Cl or Br;
$R_4$ is a straight or branched alkyl of 1–6 carbons, a cycloalkyl of 3–6 carbons;
$R_5$ is $CH_2OH$, $OCH_2CH_2OH$, OH, or $NH_2$; and
$R_6$ is methyl.

Other most preferred compounds of formula I are those wherein:
$R_1$ is 3- or 4-$(CH_2)_{n'}OH$ or a $(CH_2)_{n'}NH_2$ where n' is 0 or 1;
$R_2$ and $R_3$ are H;
$R_4$ is a straight or branched alkyl of 1–6 carbons, or a cycloalkyl of 3–6 carbons;
$R_5$ is $(CH_2)_nOH$, $OSO_2N(R)_2$, $NRSO_2N(R)_2$, $CON(R)_2$, $NRSO_2R$, $(CH_2)_nN(R)_2$, or $OSO_2R$;
$R_6$ is $CH_3$;
R is independently H, a straight or branched alkyl of 1–5 carbons, a $—(CH_2)_m$-cycloalkyl wherein the cycloalkyl is of 3–6 carbons and wherein m is an integer of from 0 to 3, $—(CH_2)_m—$, Ph, a $(CH_2)_m$-heterocycle wherein the heterocycle is of 5–6 atoms with 1–3 heteroatoms and wherein m is an integer of from 0 to 3, and wherein the $(R)2$ in $N(R)_2$ may be a heterocycle containing the nitrogen, all optionally substituted by F, Cl, Br, —CN, —CF_3, OR', COH, $N(R')_2$, $CON(R')_2$, or NR'COR'; and
R' is H, a straight or branched alkyl of 1–3 carbons, or Ph;
n is 0–2.

The most preferred compounds of formula I are those wherein:
$R_1$ is 4-OH or $NH_2$;
$R_2$ and $R_3$ are H;
$R_4$ is isopropyl, cyclobutyl, cyclopentyl, or cyclohexyl;
$R_5$ is $(CH_2)_nOH$, $OSO_2N(R)_2$, $NHSO_2N(R)_2$, $NH_2$, or $OSO_2R$;
$R_6$ is methyl;
R is H, a straight or branched alkyl of 1–4 carbons, Ph, a heterocycle wherein the heterocycle is of 5 or 6 atoms with 1–2 heteroatoms, all may be optionally substituted by $N(R')_2$, $CON(R')_2$, NR'COR'; and
R' is H, a straight or branched alkyl of 1–3 carbons, or Ph;
n is 0–2.

Other most preferred compounds are those of formula I wherein:
$R_1$ is 3-OH or $NH_2$;
$R_2$ and $R_3$ are H;
$R_4$ is isopropyl, cyclobutyl, cyclopentyl, or cyclohexyl;
$R_5$ is $(CH_2)_nOH$, $OSO_2N(R)_2$, $NHSO_2N(R)_2$, $NH_2$, or $OSO_2R$;
$R_6$ is methyl;
R is H, a straight or branched alkyl of 1–4 carbons, Ph, a heterocycle wherein the heterocycle is of 5 or 6 atoms with 1–2 heteroatoms optionally substituted by $N(R')_2$, $CON(R')_2$, or NR'COR';
R' is H, a straight or branched alkyl of 1–3 carbons, or Ph;
n is 0–2.

Especially preferred compounds are selected from:
3-[2-tert-Butyl-4-(2-hydroxy-ethoxy)-5-methyl-phenylsulfanyl]-4-hydroxy-6-[2-(4-hydroxy-phenyl)-ethyl]-6-methyl-5,6-dihydro-pyran-2-one, (+/−);
3-[2-tert-Butyl-4-hydroxymethyl-5-methyl-phenylsulfanyl]-4-hydroxy-6-[2-(4-hydroxy-phenyl)-ethyl]-6-isopropyl-5,6-dihydro-pyran-2-one, (+/−);
Ethyl-sulfamic acid 5-tert-Butyl-4-{4-hydroxy-6-[2-(4-hydroxy-phenyl)-ethyl]-6-methyl-2-oxo-5,6-dihydro-2H-pyran-3-ylsulfanyl}-phenyl ester, (+/−);
Dimethyl-sulfamic acid 5-tert-Butyl-4-{4-hydroxy-6-[2-(4-hydroxy-phenyl)-ethyl]-6-methyl-2-oxo-5,6-dihydro-2H-pyran-3-ylsulfanyl}-phenyl ester, (+/−);
3-[2-tert-Butyl-4-(2-hydroxy-ethoxy)-5-methyl-phenylsulfanyl]-4-hydroxy-6-[2-(4-hydroxy-phenyl)-ethyl]-6-isopropyl-5,6-dihydro-pyran-2-one, (+/−);
(S)-3-(2-tert-Butyl-4-hydroxymethyl-5-methyl-phenylsulfanyl)-4-hydroxy-6-[2-(4-hydroxy-phenyl)-ethyl]-6-isopropyl-5,6-dihydro-pyran-2-one (+);
(S) 3-(2-tert-Butyl-4-hydroxymethyl-5-methyl-phenylsulfanyl)-6-cyclopentyl-4-hydroxy-6-[2-(3-hydroxy-phenyl)-ethyl]-5,6-dihydro-pyran-2-one (+);
(S)-(6-[2-(4-Amino-phenyl)-ethyl]-3-(2-tert-butyl4-hydroxymethyl-5-methyl-phenylsulfanyl)-4-hydroxy-6-isopropyl-5,6-dihydro-pyran-2-one;
(S) 3-(4-Amino-2-tert-butyl-5-methyl-phenylsulfanyl)-4-hydroxy-6-[2-(4-hydroxy-phenyl)-ethyl]-6-isopropyl-5,6-dihydro-pyran-2-one;
tert-Butyl-sulfamic acid 5-tert-Butyl-4-{4-hydroxy-6-[2-(4-hydroxy-phenyl)-ethyl]-6-methyl-2-oxo-5,6-dihydro-2H-pyran-3-ylsulfanyl}-2-methyl-phenyl ester, (+/−);
6-Butyl-3-[2-tert-butyl-4-hydroxymethyl-5-methyl-phenylsulfanyl]-4-hydroxy-6-[2-(4-hydroxy-phenyl)-ethyl]-5,6-dihydro-pyran-2-one, (+/−);
Ethyl-sulfamic acid 5-tert-butyl-4-{6-cyclohexyl-4-hydroxy-6-[2-(4-hydroxy-phenyl)-ethyl]-2-oxo-5,6-dihydro-2H-pyran-3-ylsulfanyl}-2-methyl-phenyl ester;

3-(2-tert-Butyl-4-hydroxymethyl-5-methyl-phenylsulfanyl)-6-cyclohexyl-4-hydroxy-6-[2-(4-hydroxy-phenyl)-ethyl]-5,6-dihydro-pyran-2-one;

3-(2-tert-Butyl-4-hydroxy-5-methyl-phenylsulfanyl)-6-cyclohexyl-4-hydroxy-6-[2-(4-hydroxy-phenyl)-ethyl]-5,6-dihydro-pyran-2-one;

3-(4-Amino-2-tert-butyl-5-methyl-phenylsulfanyl)-4-hydroxy-6-[2-(4-hydroxy-phenyl)-ethyl]-6-methyl-5,6-dihydro-pyran-2-one monohydrochloride;

N-[4-[[5,6-Dihydro-4-hydroxy-6,6-bis[2-(4-hydroxyphenyl)ethyl]-2-oxo-2H-pyran-3-yl]thio]-5-(1,1-dimethylethyl)-2-methylphenyl]-N',N'-dimethyl-sulfamide;

N-(5-tert-Butyl-4-{4-hydroxy-6-[2-(4-hydroxy-phenyl)-ethyl]-6-methyl-2-oxo-5,6-dihydro-2H-pyran-3-ylsulfanyl}-2-methyl-phenyl)-4-cyano-benzenesulfonamide;

3-(2-tert-Butyl-4-hydroxymethyl-5-methyl-phenylsulfanyl)-4-hydroxy-6,6-bis-[2-(4-hydroxyphenyl)ethyl]-5,6-dihydro-pyran-2-one;

6-[2-(4-aminophenyl)ethyl]-3-(2-tert-butyl-4-hydroxymethyl-5-methyl-phenylsulfanyl)-4-hydroxy-6-phenyl-5,6-dihydro-pyran-2-one;

6,6-Bis-[2-(4-aminophenyl)ethyl]-3-(2-tert-butyl-4-hydroxymethyl-5-methyl-phenylsulfanyl)-4-hydroxy-5,6-dihydro-pyran-2-one;

3-(tert-Butyl-4-hydroxymethyl-5-methyl-phenylsulfanyl)-4-hydroxy-6-phenethyl-6-phenyl-5,6-dihydro-pyran-2-one (S isomer);

3-[2-tert-Butyl-4-(2-hydroxy-ethoxy)-5-methyl-phenylsulfanyl]-4-hydroxy- 6,6-bis-[2-(4-hydroxy-phenyl)-ethyl]-5,6-dihydro-pyran-2-one;

(5-tert-Butyl-4-{4-hydroxy-6,6-bis-[2-(4-hydroxy-phenyl)-ethyl]-2-oxo-5,6-dihydro-2H-pyran-3-ylsulfanyl}-2-methyl-phenoxy)-acetic acid ethyl ester;

3-(4-Amino-2-tert-butyl-5-methyl-phenylsulfanyl)-4-hydroxy-6,6-bis[2-(4-hydroxy-phenyl)ethyl]-5,6-dihydro-pyran-2-one;

3-(2-tert-Butyl-4-hydroxymethyl-5-methyl-phenylsulfanyl)-4-hydroxy-6,6-bis-[2-(3-hydroxy-phenyl)ethyl]-5,6-dihydro-pyran-2-one;

Dimethyl-sulfamic acid 5-tert-butyl-4-{4-hydroxy-6,6-bis-[2-(3-hydroxy-phenyl)-ethyl]-2-oxo-5,6-dihydro-2H-pyran-3-ylsulfanyl}-2-methyl-phenyl ester;

3-[2-tert-Butyl-4-(2-hydroxy-ethoxy)-5-methyl-phenylsulfanyl]-4-hydroxy-6,6-bis[2-(4-hydroxy-3-methoxy-phenyl)-ethyl]-5,6-dihydro-pyran-2-one;

3-(2-tert-Butyl-4-hydroxy-5-methyl-phenylsulfanyl)-4-hydroxy-6-[4-(2-hydroxy-ethoxy)-phenyl]-6-phenethyl-5,6-dihydro-pyran-2-one;

3-[2-tert-Butyl-4-(2-hydroxy-ethoxy)-5-methyl-phenylsulfanyl]-4-hydroxy-6-[4-(2-hydroxy-ethoxy)-phenyl]-6-phenethyl-5,6-dihydro-pyran-2-one;

Dimethyl-sulfamic acid 5-tert-butyl-4-{4-hydroxy-2-oxo-6-phenethyl-6-[4-(2-piperazin-1-yl-ethoxy)-phenyl]-5,6-dihydro-2H-pyran-3-ylsulfanyl }-2-methyl-phenyl ester;

Dimethyl-sulfamic acid 5-tert-butyl-4-{4-hydroxy-6,6-bis-[2-(4-hydroxy-phenyl)-ethyl]-2-oxo-5,6-dihydro-2H-pyran-3-ylsulfanyl}-2-methyl-phenyl ester;

Ethyl-sulfamic acid 5-tert-butyl-4-{4-hydroxy-6,6-bis-[2-(4-hydroxy-phenyl)-ethyl]-2-oxo-5,6-dihydro-2H-pyran-3-ylsulfanyl}-2-methyl-phenyl ester;

Ethyl-sulfamic acid 5-tert-butyl-4-{6,6-bis-[2-(4-amino-phenyl)-ethyl]-4-hydroxy-2-oxo-5,6-dihydro-2H-pyran-3-ylsulfanyl}2-methyl-phenyl ester;

4-Methyl-piperazine-1-sulfonic acid 5-tert-butyl-4-{4-hydroxy-6,6-bis-[2-(4-hydroxy-phenyl)-ethyl]-2-oxo-5,6-dihydro-2H-pyran-3-ylsulfanyl}-2-methyl-phenyl ester;

4-Methyl-piperazine-1-sulfonic acid 5-tert-butyl-4-{4-hydroxy-6-[2-(4-hydroxy-phenyl)-ethyl]-6-methyl-2-oxo-5,6-dihydro-2H-pyran-3-ylsulfanyl}-2-methyl-phenyl ester;

1-Methyl-1H-imidazole-4-sulfonic acid 5-tert-butyl4-{4-hydroxy-6-[2-(4-hydroxy-phenyl)-ethyl]-6-methyl-2-oxo-5 ,6-dihydro-2H-pyran-3-ylsulfanyl }-2-methyl-phenyl ester;

3-(2-tert-Butyl-5-methyl-phenylsulfanyl)-4-hydroxy-6-[4-(2-hydroxy-ethoxy)-phenyl]-6-phenethyl-5,6-dihydro-pyran-2-one;

3-(2-tert-Butyl-5-methyl-phenylsulfanyl)-4-hydroxy-6-[4-(2-morpholin-4-yl-ethoxy)-phenyl]-6-phenethyl-5,6-dihydro-pyran-2-one;

3-(2-tert-Butyl-5-methyl-phenylsulfanyl)-4-hydroxy-6-phenethyl-6-[4-(2-piperazin-1-yl-ethoxy)-phenyl]-5,6-dihydro-pyran-2-one;

3-(2-tert-Butyl-4-hydroxymethyl-5-methyl-phenylsulfanyl)-4-hydroxy-6-[2-(4-hydroxy-phenyl)-ethyl]-6-phenyl-5,6-dihydro-pyran-2-one; and 3-(2-tert-Butyl-4-hydroxymethyl-5-methyl-phenylsulfanyl)-4-hydroxy-6- [2-(3-hydroxy-phenyl)-ethyl]-6-phenyl-5,6-dihydro-pyran-2-one.

The testing of specific 5,6-dihydropyrones as inhibitors of the HIV aspartyl protease, based on the study of the hydrolysis of an undecapeptide enzyme substrate, and the testing of the 5,6-dihydropyrones as inhibitors of viral growth and infectivity, based on the study of infection of H9 cell lines by the HIV-1$_{iiib}$ strain, are also disclosed. Striking enzyme inhibitions, at nanomolar levels, with corresponding anti-HIV activities were observed. The methods employed follow the procedures of Tummino, et al. (*Archives of Biochemistry and Biophysics* 1995, 316, 523).

The inventors contemplate the preparation of pharmaceutically useful antiviral compositions comprising one or more of the invented 5,6-dihydropyrones and related compounds and a pharmaceutically acceptable carrier. They also contemplate the use of these compositions, alone or in combination with other antiviral treatments (including the use of nucleosides such as AZT, non-nucleosides such as RT inhibitors, and other protease inhibitors) in the treatment of infections and diseases caused by retroviruses, including AIDS. Other antiretroviral agents include, for example, AZT, TIBO, and ddC, which inhibit reverse transcriptase. The antiviral agents which inhibit transactivation by inhibiting the function of the transactivator protein can be administered with the compounds of the invention.

The processes for preparing the final products are also part of the instant invention. Novel intermediates include, but are not limited, to the following:

[1R-[1α(S*),2β,5α]]-3-Hydroxy-3,5-diphenyl-pentanoic acid 2-isopropyl-5-methyl-cyclohexyl ester;

(S)-3-Hydroxy-3,5-diphenyl-pentanoic acid;

3-[2-(4-Benzyloxy-phenyl)-ethyl]-3-hydroxy-4-methyl-pentanoic acid tert-butyl ester;

3-[2-(4-Benzyloxy-phenyl)-ethyl]-3-hydroxy-4-methyl-pentanoic acid;

3-[2-(4-Benzyloxy-phenyl)-ethyl]-3-hydroxy-4-methyl-pentanoic acid methyl ester;

(S)-3-Hydroxy-3-[2-(4-hydroxy-phenyl)-ethyl]-4-methyl-pentanoic acid methyl ester;

(S)-3-Hydroxy-3-[2-(4-hydroxy-phenyl)-ethyl]-4-methyl-pentanoic acid; 5-(3-Benzyloxy-phenyl)-3-cyclopentyl-3-hydroxy-pentanoic acid tert-butyl ester;

(S) 5-(3-Benzyloxy-phenyl)-3-cyclopentyl-3-hydroxy-pentanoic acid tert-butyl ester;

(S)-5-Hydroxy-3-oxo-5,7-diphenyl-heptanoic acid methyl ester;

4-Hydroxy-6-[2-(4-hydroxy-phenyl)-ethyl]-6-methyl-5,6-dihydro-pyran-2-one;
4-Hydroxy-6-[2-(4-hydroxy-phenyl)-ethyl]-6-isopropyl-5,6-dihydro-pyran-2-one;
6-Butyl-4-hydroxy-6-[2-(4-hydroxy-phenyl)-ethyl]5,6-dihydro-pyran-2-one;
6-Cyclohexyl-4-hydroxy-6-[2-(4-hydroxy-phenyl)-ethyl]-5,6-dihydro-pyran-2-one;
(1,1-Dimethylethyl)[(3,6-dihydro-4-hydroxy-6-oxo-2H-pyran-2,2-diyl)bis[2,1-ethanediyl-(4,1-phenylene)] bis-carbamate;
4-Hydroxy-6,6-bis-[2-(4-hydroxy-phenyl)-ethyl]-5,6-dihydro-pyran-2-one;
4-Hydroxy-6,6-bis-[2-(4-hydroxy-3-methoxy-phenyl)-ethyl]-5,6-dihydro-pyran-2-one;
N-{4-[2-(4-Hydroxy-6-oxo-2-phenyl-3,6-dihydro-2H-pyran-2-yl)-ethyl]-phenyl}-acetamide;
6-{4-[2-(tert-Butyl-dimethyl-silanyloxy)-ethoxy]-phenyl}-4-hydroxy-6-phenethyl-5,6-dihydro-pyran-2-one;
4-Hydroxy-6-[2-(4-hydroxy-phenyl)-ethyl]-6-phenyl-5,6-dihydro-pyran-2-one;
4-Hydroxy-6-[2-(3-hydroxy-phenyl)-ethyl]-6-phenyl-5,6-dihydro-pyran-2-one;
(S)-4-Hydroxy-6-phenethyl-6-phenyl-5,6-dihydro-pyran-2-one;
4-(2-{[4-Hydroxy-6-oxo-2-phenethyl-3,6-dihydro-2H-pyran-2-yl]-phenoxy}ethyl)-piperazine-1-carboxylic acid tert-butyl ester;
4-Hydroxy-6,6-bis-[2-(3-hydroxy-phenyl)-ethyl]-5,6-dihydro-pyran-2-one;
4-Hydroxy-6,6-diphenethyl-5,6-dihydro-pyran-2-one;
4-Hydroxy-6-(3-methyl-butyl)-6-phenethyl-5,6-dihydro-pyran-2-one;
(S)-4-Hydroxy-6-[2-(4-hydroxy-phenyl)-ethyl]-6-isopropyl-5,6-dihydro-pyran-2-one;
6-[2-(3-Benzyloxy-phenyl)-ethyl]-6-cyclopentyl-4-hydroxy-5,6-dihydro-pyran-2-one;
6-Cyclopentyl-4-hydroxy-6-[2-(3-hydroxy-phenyl)-ethyl]-5,6-dihydro-pyran-2-one;
Toluene-4-thiosulfonic acid S-(2-tert-butyl-4-hydroxymethyl-5-methyl-phenyl) ester;
Toluene-4-thiosulfonic acid S-[2-tert-butyl-4-(tert-butyl-dimethyl-silanyloxy)-5-methyl-phenyl] ester;
Toluene-4-thiosulfonic acid S-{2-tert-butyl-4-[2-(tert-butyl-dimethyl-silanyloxy)-ethoxy]-5-methyl-phenyl}ester;
Toluene-4-thiosulfonic acid S-(2-tert-butyl-4-hydroxy-5-methyl-phenyl) ester;
Toluene-4-thiosulfonic acid S-(2-tert-butyl-4-dimethylsulfamoyloxy-5-methyl-phenyl) ester;
Toluene-4-thiosulfonic acid S-(2-tert-butyl-4-ethylsulfamoyloxy-5-methyl-phenyl) ester;
4-Methyl-piperazine-1-sulfonic acid, 5-tert-butyl-2-methyl-4-(toluene-4-sulfonylsufanyl)-phenyl ester;
1-Methyl-1H-imidazole-4-sulfonic acid, 5-tert-butyl-2-methyl4-(toluene- 4-sulfonylsufanyl)-phenyl ester;
Toluene-4-thiosulfonic acid S-(2-tert-butyl-4-tert-butyllsulfamoyloxy-5-methyl-phenyl) ester;
Toluene 4-thiosulfonic acid S-[2-tert-butyl-4-(2-methoxymethoxy-ethoxy)-5-methyl-phenyl] ester;
[5-(1,1-Dimethylethyl)-2-methyl-4-[[(4-methylphenyl)sulfonyl]thio]-phenyl]-imidodicarbonic acid bis(1,1-dimethylethyl) ester;
Toluene4-thiosulfonic acid S-(4-amino-2-tert-butyl-5-methyl-phenyl) ester;
4-Methyl-benzenesulfonothioic acid[4-[[(dimethylamino)sulfonyl]amino]-2-(1,1-dimethylethyl)-5-methylphenyl] ester;
Toluene-4-thiosulfonic acid S-[2-tert-butyl-4-(4-cyano-benzenesulfonylamino)-5-methyl-phenyl] ester;
2-tert-Butyl-5-methylphenyl-p-toluenethiosulfonate; and
[5-tert-Butyl-2-methyl-4-(toluene-4-sulfonylsulfanyl)-phenoxy]-acetic acid.

DETAILED DESCRIPTION OF THE INVENTION

Here, the term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, and dodecyl. The alkyl groups may contain one or more sites of unsaturation such as double or triple carbon-carbon bonds. The alkyl group is unsubstituted or substituted by from 1 to 3 substituents selected from alkyl, alkoxy, thioalkoxy all as defined herein, hydroxy, thiol, nitro, halogen, amino, formyl, carboxyl, nitrile, —NH—CO—R, —CO—NH—, —CO$_2$R, —COR, aryl, or heteroaryl wherein alkyl (R), aryl, and heteroaryl are defined as herein.

The term "cycloalkyl" means a hydrocarbon ring which contains from 3 to 12 carbon atoms unless otherwise specified, for example, cyclopropyl, cyclobutyl, cyclopentyl, cyclohexyl, and adamantyl. Where possible, the cycloalkyl group may contain double bonds. The cycloalkyl ring may be unsubstituted or substituted by from 1 to 3 substituents selected alkyl, alkoxy, thioalkoxy all as defined herein, hydroxy, thiol, nitro, halogen, amino, formyl, carboxyl, nitrile, —NH—CO—R, —CO—NHR—, —CO$_2$R, —COR, aryl, or heteroaryl wherein alkyl (R), aryl, and heteroaryl are defined as herein.

The term alkylcycloalkyl means a cycloalkyl group as defined above attached directly to an alkyl group as defined above.

The terms "alkoxy" and "thioalkoxy" are O-alkyl or S-alkyl as defined above for alkyl.

The term spirocycle refers to a carbocyclic or heterocyclic ring whose ends meet at a single carbon in a chain or another ring.

The terms heteroaryl and heterocycle mean a heterocyclic radical which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isaxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl, 1- or 2-piperazinyl, 2-, 3-, or 4-morpholinyl, 2-, 3-, or 4-thiomorpholinyl, 1-, 2-, or 3-pyrrolidinyl, 2- or 3-tetrahydrofuranyl, 2-, 3-, or 4-tetrahydropyranyl, 2-, 3-, or 4-piperidinyl, 1-, 2-, 4-, 5-, or 6-tetrahydropyrimidinyl, 2-dioxolinyl, 2-, 4-, or 5-imidazolidinyl, 1-, 2-, 3-, 4-, 5-, 6-, or 7-indolinyl, unsubstituted or substituted by 1 to 2 substituents selected from alkyl as defined above, aryl as defined above, alkoxy as defined above, thioalkoxy as defined above, hydroxy, thiol, nitro, halogen, formyl, amino, carboxyl, nitrile,—NHCOR, —CO$_2$R, —COR, wherein alkyl in as defined above or phenyl. For heterocycles containing sulfur, the oxidized sulfur heterocycles containing SO or SO$_2$ groups are also included.

Halogen is fluorine, chlorine, bromine or iodine.

Some of the compounds of Formula 1 are capable of further forming pharmaceutically acceptable acid-addition and/or base salts. All of these forms are within the scope of the present invention.

Pharmaceutically acceptable acid addition salts of the compounds of Formula 1 include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al., "Pharmaceutical Salts," *Journal of Pharmaceutical Science,* 66: 1–19 (1977).

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S.M., et al., "Pharmaceutical Salts," *Journal of Pharmaceutical Science,* 66: 1–19 (1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula 1 or a corresponding pharmaceutically acceptable salt of a compound of Formula 1.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component as determined by a skilled physician. The composition can, if desired, also contain other compatible therapeutic agents.

In therapeutic use as antagonists of a retroviral protease, as agents for the treatment of infections caused by a retrovirus including HIV, or as agents for the treatment of diseases due to AIDS, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The compounds of the present invention can be prepared according to the various synthetic schemes that follow. Protecting groups may be used when appropriate throughout many of the schemes. Although specifically noted in certain schemes, the appropriate use and choice of protecting groups is well known by one skilled in the art, and is not limited to the specific examples below. It is also understood that such groups not only serve to protect chemically reactive sites, but also to enhance solubility or otherwise change physical properties. A good general reference for protecting group preparation and deprotection is "Protecting Groups in Organic Synthesis" by Theodora Green. A number of general reactions such as oxidations and reductions etc. are not shown in detail but can be done by methods understood by one skilled in the art. General transformations are well reviewed in "Comprehensive Organic Transformation" by Richard Larock, and the series "Compendium of Organic Synthetic Methods" published by Wiley-Interscience. In general, the starting materials were obtained from commercial sources unless otherwise indicated.

There are three major components of the synthesis of the desired products. The formation of a ketone precursor, the cyclization of that ketone into the dihydropyrone ring system and the addition of the thiol component to complete the preparation of the compounds of the invention. Schemes 1 through 6 address the various methods for preparation of ketones indicated as D,G,K and M.

See Scheme 1 (The schemes begin on page 122.)

The chalcones (C) can be prepared by reaction of the appropriate methylketones and aldehydes using Ba(OH)$_2$ in EtOH as described in Synthesis, 1983, 502–504, An. Quim, Ser. C, 1981, 77(2), 222–224, and Pol. J. Chem., 1982, 56(10–112), 1435. Alternatively the chalcones(C) can be prepared by reaction of the appropriate methylketones and aldehydes using NaOH in EtOH as described by Kohler and Chadwell, Org. Synth. Coll., Vol. I, 78, 1941. The relative ratio of aldehyde, ketone, base and temperature (RT to reflux) varied according to the substitution pattern of the aldehyde and ketone. There have also been reports of conversion of A and B to chalcones C under acidic conditions using H$_2$SO$_4$ and acetic anhydride. This may be accomplished by direct treatment with acid or the acid may be used to dehydrate the aldol intermediate if it does not dehydrate during the reaction with base.

The resulting chalcones(C) were converted into ketones (D) by reduction.

The reduction was generally accomplished by hydrogenation using palladium on barium sulfate at room temperature in tetrahydrofuran. On occasion overreduction to the alcohol was observed. The isolated alcohol or the crude mixture can be oxidized to the ketone with Jones reagent.

The reduction of the enone to the corresponding ketone can be carried out via a number of alternative methods including but not limited to: metals in ammonia as described in Org. Reactions, 1976, Vol 23, 1–253; ethylene glycol and RuCl$_2$[P(Ph)$_3$]$_3$ as described in Synthesis, 1973, 359; and copper hydride reagents as described in J. Amer. Chem. Soc., 1974, 96, 3686.

See Scheme 2

Preparation of the ketone G can be accomplished from an appropriate acid(E) and appropriate nucleophile using the Weinreb methodology described in Tetrahedron Letters, 1987, 1857. The appropriate acid can be converted to the acid chloride by treatment with neat thionyl chloride or by treatment with oxalyl chloride in methylene chloride with a catalytic amount of DMF. Treatment of the acid chloride with N,O-dimethylhydroxylamine with bases such as pyridine or triethylamine in inert solvents such as methylene chloride from 0° C. to reflux will give intermediate F. Intermediate F can then be converted to G by treatment with the appropriate nucleophile, such as Grignard reagents, at 0° C. to reflux in solvents such as tetrahydrofuran or diethyl ether. An alternative method of converting the acid E to ketone G is by treatment with alkyl lithiums at −78° C. to reflux as described in J. Med. Chem., 1996, 39, 2659 and J. Am. Chem. Soc., 1970, 92, 2590. Another route is treatment of the acid chloride with nucleophiles (organomagnesium, copper, cadmium, manganese or zinc reagents) as reviewed in Org. React., 1954, 8, 28; Tetrahedron Letters, 1992, 33, 31, 4439; and Tetrahedron Lett., 1970, 4647.

See Scheme 3

An alternative preparation of ketone D can be accomplished by reaction of an allylic alcohol(I) with an appropriate halide(H) using palladium acetate as described in Tetrahedron, 1979, 35, 329, and Tetrahedron Letters, 1991, 32, 2121. There are number of catalysts and conditions which will effect this transformation such as: Pd(OAc)$_2$, NaHCO$_3$, DMF, tetrabutylammonium chloride at RT to reflux; Pd(OAc)$_2$, triethylamine, acetonitrile at RT to reflux.

See Scheme 4

An alternative preparation of ketone G can be accomplished by reaction of aldehyde A with an appropriate nucleophile such as an organo lithium or Grignard reagents from −78° C. to room temperature in inert solvents to afford the alcohol. The desired ketone G can by formed by oxidation of the resulting alcohol with Jones reagent or other oxidizing conditions such as the Swern oxidation which are well known to one skilled in the art.

See Scheme 5

Friedyl Crafts acylation of the appropriately substituted aromatic can be accomplished by reaction with an acid chloride and aluminum chloride to give ketone K as described by A. I. Vogel, Practical Organic Chemistry, 1962, 729–732. The acid chloride, aluminum trichloride, and aromatic substrate, which may also be used as the solvent, are reacted in solvents such as benzene, nitrobenzene, or hexane at 0° C. to reflux to afford ketone K. The acid chloride can be reacted with unsubstituted aromatics as well as with substituted aromatics. If an unprotected alcohol is present, additional equivalents of acid chloride can be used to convert the alcohol to the ester, so that the final product would contain an acyl group on the aromatic ring and an ester.

See Scheme 6

Acid E can be converted to desired ketone(M) utilizing a four step route indicated in Scheme 6. The appropriate acid(E) can be converted into the corresponding β-ketoester (L) utilizing conditions described in Tetrahedron Letters, 1992, 1945 and Angew. Chem. Int. Ed., 1979, 72. The resulting β-ketoester L can be treated with a base, such as NaH or lithium diisopropylamide(LDA), then with an appropriate alkylating agent, R'X at 0° C. to room temperature to give the alkylated β-ketoester. The β-ketoester can be decarboxylated with acid in tetrahydrofuran at reflux. Alternatively the β-ketoester can be hydrolyzed with base to the acid, then heated with or without acid to give the desired ketone(M).

Scheme 7 displays a general method useful for preparation of phenols or amines as they pertain to the compounds of the invention. These phenols and amines are used for various substituents at the 3 and 6 position of the dihydropyrone products.

See Scheme 7

Chain extension of phenols and amines(N) to the corresponding ethylene hydroxylated compounds(O) can be accomplished by heating with ethylene carbonate and tetrabutyl ammonium iodide. Alternative methods are alkylation of compound N with iodoethanol or TosO(CH$_2$)$_2$OH (J. Med. Chem., 1995, 1608) with base such as cesium carbonate in solvents such as dioxane, acetone and methylene chloride. In some instances the use of a catalytic amount of sodium iodide can be used to enhance reactivity. Alternatively, the phenol can be reacted with a bromoacetate and the resulting ester can be reduced with a hydride such as LiAlH4 in inert solvents to give compound O. The alcohol, on intermediate O, can be protected with standard protecting groups such as tertbutyldimethylsilyl or methoxyethoxymethyl and carried through additional steps before deprotecting. Alternatively, the alcohol can be converted to the mesylate, or activated to a leaving group, and then displaced with nucleophiles such as morpholine, piperazine, or azide to afford P. This representative scheme can be used to modify phenols at a variety of positions on different aromatic rings.

The Ketones D, G, K, M and those prepared from Scheme 7 are cyclized to the dihydropyrone ring following the routes shown in Schemes 8 and 9. Scheme 9 also describes methods for obtaining optically pure forms of the dihydropyrone ring which is a recognized and important aspect of the current invention. The same methods can be used to produce racemic compounds if the resolution step is removed.

See Scheme 8

The dihydropyrone ring system can be prepared as described in Can. J. Chem., 1974, 52, 2157–2164 and Synthetic Communications, 1988, 18(9), 949–963. Reaction of the dianion of acetoacetate(Q) with the appropriate ketone (D, G, K or M) in inert solvents such as tetrahydrofuran at 0° C. to room temperature gave aldol intermediate R. Water can be added directly to the reaction to effect closure. Alternatively the reaction can be worked up by addition of acetic acid or ammonium chloride and the aldol product isolated and characterized or taken on crude. The aldol product(R) can be closed by treating with dilute sodium hydroxide with or without tetrahydrofuran present. The tetrahydrofuran may be necessary to assist in solubilizing the aldol intermediate(R). Protecting groups on intermediate R can be removed before closure to assist in solubilizing the intermediate in base.

Other routes are available to form the dihydropyrone ring such as those described in: J. C. S. Chem. Comm., 1979, 578; J. Am. Chem. Soc., 1984, 106, 4294; and J. Org. Chem., 1975, 40, 1610.

See Scheme 9

The dihydropyrone ring system can also be prepared optically enriched as shown in Scheme 9. The appropriate ketone(D, G, K or M) can be reacted with the appropriate Reformatsky reagent, the equivalent lanthanide species (Tetrahedron 1981, 37, (Supp. 1), 175; J. Org. Chem., 1984, 49, 3904) or the anion of t-butyl acetate in inert solvents such as tetrahydrofuran at −78° C. to reflux to afford the aldol intermediate. The two antipodes can be separated by a chiral HPLC column such as Chiralcel OD(90% hexane/ 0.1% TFA/10% isopropyl alcohol) or selective enzymatic hydrolysis with enzymes such as Candida antarctica "B" lipase in phosphate buffer with cosolvents such as isopropyl alcohol at room temperature. The resolved ester can be hydrolyzed to the acid(T*) using base under standard conditions.

Intermediate T* can also be prepared in a chiral form by reaction of ketone G with a chiral ester(U) to give an intermediate which is a mixture of diasteromers (J. Org. Chem., 1982, 47, 1; Tetrahedron, 1980, 36, 227). The aldol mixture can be separated by recrystallization or by chromatography to give each enantiomer. Hydrolysis of the ester using base affords acid T*.

Intermediate T can be prepared in racemic form and then resolved by classical means such as cocrystallization with a chiral amine such as 1-(1-naphthyl)ethylamine in solvents such as water and isopropyl alcohol. Analysis of the chiral salt by x-ray may allow the determination of the absolute stereochemistry of intermediate T*.

The intermediate T* can be converted to R* by activation of the acid and treatment with the magnesium salt of a half acid ester which is also described in Scheme 6.

Schemes 10 to 14 describe the synthesis of a number of the tosyl reagents (AA, EE, LL) which are used to introduce the 3-thiol moiety to the dihydropyrones of the invention.

See Scheme 10

Phenol V can be reacted with electrophiles, such as Br$_2$ in inert solvents at 0° C. to room temperature, to give the para substituted phenol. The phenol can be protected with groups such as methoxyethoxymethyl or tertbutyldimethylsilyl which are known to one skilled in the art. The bromine in derivative W can be converted to an anion at low temperature to room temperature by treatment with an alkyl lithium and reacted with electrophiles such as carbon dioxide. The derivatized phenol can be converted to the corresponding thiol using a variety of methods (Tetrahedron Letters, 1996, 4523, Chem. Let, 1985, 1307, and Tetrahedron Lett, 1993, 393). The Newman-Kwart rearrangement is also useful for the conversion of phenol to thiophenol as described in J. Org. Chem., 1966, 3980; Synth, 1975, 43; and J. Chem. Eng. Data., 1975, 20, 443. Phenol X can be treated with bases such as sodium hydride and dimethylthiocarbamoyl chloride in solvents such as DMF or tetrahydrofuran at 0° C. to reflux to give Y. Vigorous heating of Y at temperatures in the 200° C. to 330° C. range affords intermediate Z. The free thiol can be prepared by reduction of derivatives such as Z with diisobutylaluminum hydride(DIBAL—H) or lithium aluminum hydride in inert solvents such as toluene or tetrahydrofuran from −78° C. to room temperature or by hydrolysis in base. The desired thiotosylate AA can be prepared by reaction of the thiol with tosyl bromide and base such as triethylamine or pyridine in inert solvents such as carbon tetrachloride or toluene at 0° C. to room temperature.

See Scheme 11

Another route into desired thiotosyl reagents is indicated in Scheme 11. Aniline BB can be converted to the corresponding phenol using a variety of conditions(J. Org. Chem., 1951, 16, 586; Org. Synth., 1955, Coll. Vol. 3, 130). The phenol can be treated with sodiumthiocyanate, sodium bromide, and bromine in methanol at 0° C. to 50° C. to incorporate the thiocyanate to give CC (Synth., 1992, 656). The phenol can be modified or protected using conditions which are understood by one skilled in the art. The thiocyanate can be converted to the thiol(DD) by treatment with dithiothreitol(DTT) in phosphate buffer in ethanol at room temperature to reflux or by treatment with lithium aluminum hydride(LAH) in inert solvents such as tetrahydrofuran at 0° C. to room temperature. The desired thiotosylate EE can be prepared by reaction of the thiol with tosyl bromide and base as described in Scheme 10.

See Scheme 12

Thiol DD can be converted to the disulfide(FF) by treatment with iodine and triethylamine in ethyl acetate. The disulfide can act as a protecting group for the sulfur. Various reactions can then be carried out on FF and the disulfide convert back to the thiol by treatment with dithiothreitol (DTT) using similar conditions as described in Scheme 11. Reaction of the free thiophenol with tosyl bromide as previously described affords the desired tosyl reagent(EE).

See Scheme 13

Thiocyanate CC can be converted to the thiol and then to thiotosylate GG using conditions which have been described in previous schemes. Thiotosylate GG can be derivitized or a protecting group attached using conditions known to one skilled in the art to give EE.

See Scheme 14

The nitro aromatic HH (J. Org. Chem., 1951, 586) can be reduced to the corresponding aniline by hydrogenation over Raney Nickel at room temperature. The thiocyanate can be introduced para to the amine in a similar manner as described in Scheme 11. Aniline II can be converted to LL by modification of the amine, conversion to thiol(JJ), and tosylation as previously described. Alternatively aniline II can be protected, converted to the thiol, and reacted with tosyl bromide to give KK. Aniline KK can be deprotected and then modified to give LL. The reactions in this scheme have been previously described or are known to one skilled in the art.

Scheme 15 shows the convergent preparation of the desired compounds of the invention. The dihydropyrones (S) described in Schemes 8 and 9 are reacted with the tosyl reagents (AA, EE, LL) described in Schemes 10 to 14 to produce the target compounds.

See Scheme 15

The desired dihydropyrone(MM) can be prepared by reaction with the appropriate dihydropyrone(S), thiotosylate (AA, EE, LL), and potassium carbonate in dimethylformamide(DMF) at room temperature. Other bases and solvents will also effect this reaction such as triethylamine in ethanol or sodium hydride in tetrahydrofuran at 0° C. to reflux. Alternatively the intermediate S can be brominated with NBS in tert-butanol and then displaced with the thiols such as DD and JJ.

Scheme 16 describes alternative methods for effecting the separation of enantiomers into optically pure forms after formation of the dihydropyrone ring.

See Scheme 16

It has been shown that tetrahydropyrones can be resolved as described in the ICI patent WO 93/06235. The 4-hydroxydihydropyrone can be converted to a ester and the ester hydrolyzed with an enzyme to afford chiral material. This or other similar enzymatic processes may be applicable to the dihydropyrones as indicated in Scheme 16. The 4-hydroxydihydropyrone may also be resolved by classical means by conversion into a salt with chiral amines such as 1-(1-naphthyl)ethylamine. The salt may be recrystallized and then freed to afford the desired chiral material OO*.

GENERAL METHOD 1

The chalcones were prepared according to the method of Kohler and Chadwell, Org. Synth. Coll. Vol. I 78, 1941.

Example A 1,5-Bis-(4-benzyloxy-phenyl)-penta-1,4-dien-3-one

The title compound was prepared as described in General Method 1 using 42.4 g (0.2 mol) 4-benzyloxybenzaldehyde, 700 mL absolute ethanol (EtOH), 5.8 g (0.1 mol) acetone and 10 mL 10% NaOH. The reaction was refluxed for 2 hours. After cooling the reaction was filtered, and the resultant solid dried. It was used without further purification in the next reaction. $^1$H NMR (CDCl$_3$) δ 5.11 (s, 4 H), 6.91–7.01 (m, 6 H), 7.34–7.45 (m, 10 H), 7.57 (m, 4 H), 7.69 (d, 2H).

GENERAL METHOD 2

The desired chalcones were prepared by reaction of the appropriate methylketones and aldehydes by the method described in Synthesis 1983, 502–504; An. Quim, Ser. C, 1981, 77(2), 222–224; and Pol. J. Chem., 1982, 56(10–112): 1435. To a reaction flask was added aldehyde (1–2 eq.), ketone (1–2 eq.), 95% ethanol (EtOH), and anhydrous Ba(OH)$_2$ (23 mg per mmol). The reaction was stirred at room temperature or heated at reflux for up to 2 days. The reaction was cooled to room temperature. The ethanol was evaporated and the crude reaction partitioned between ethyl acetate (EtOAc) and 1N HCl. The aqueous layer was extracted with EtOAc. The combined organic extracts were dried (MgSO$_4$) and concentrated. The crude product was purified by flash chromatography or recrystallization.

Example B 1-(4-Benzyloxy-phenyl)-4-methyl-pent-1-ene-3-one

The title compound was prepared as described in the General Method 2 using 81.1 g (942 mmol) of 3-methyl-butan-2-one, 100 g (474 mmol) of 4-benzyloxybenzaldehyde, 10 g of anhydrous barium hydroxide and 500 mL of EtOH.

Example C 3-(4-Benzyloxy-phenyl)-1-cyclohexyl-prop-2-en-1-one

The title compound was prepared as described in General Method 2 using 17.40 g (138 mmol) of cyclohexyl methyl ketone, 29.26 g (138 mmol) of 4-benzyloxybenzaldehyde, 3.17 g of barium hydroxide (anhydrous), and 300 mL of 95% EtOH. The reaction was heated at reflux for eight hours. The crude product was recrystallized from EtOAc. The 25.85 g of product, contaminated with some 4-benzyloxybenzaldehyde, was taken on without further purification.

Example D 1,5-Bis-(4-benzyloxy-3-methoxy-phenyl)-penta-1,4-dien-3-one

The title compound was prepared as described in General Method 2 using 24.2 g (100 mmol) of 4-benzyloxy-3-methoxybenzaldehyde, 500 mL of EtOH, 2.95 g (55 mmol) of acetone, and 10 mL of 0.3N Ba(OH)$_2$ (solution in H$_2$O). The mixture was heated at 60° C. for 6 hours, cooled to room temperature, and filtered to give the title compound. $^1$H NMR (DMSO-d$_6$) δ 3.86 (s, 6 H), 5.16 (s, 4 H), 7.12 (d, 2 H), 7.21–7.47 (m, 16 H), 7.69 (d, 2 H).

Example E 1,5-Bis-(3-benzyloxy-phenyl)-penta-1,4-dien-3-one

The title compound was prepared as described in General Method 2 using 5.03 g (23.7 mmol) of 3-benzyloxy-benzaldehyde, 150 mL of EtOH, 0.65 mL (11.2 mmol) of acetone, and 0.31 g of Ba(OH)$_2$.(H$_2$O)$_8$. The mixture was heated at room temperature overnight and filtered to give the title compound. $^1$H NMR (CDCl$_3$) δ 5.08 (s, 4 H), 7.03–7.07 (m, 4 H), 7.22–7.47 (m, 16 H), 7.69 (d, 2 H).

GENERAL METHOD 3

The substituted phenylpropiophenones were prepared by hydrogenation of the corresponding chalcones at room temperature at 50 psi in tetrahydrofuran (THF) with 5% palladium (Pd) on barium sulfate (BaSO$_4$) as catalyst. The catalyst was filtered off and the resulting ketone recrystallized or purified by flash chromatography.

Example F 1-(4-Benzyloxy-phenyl)-4-methyl-pentan-3-one

Hydrogenation of 50 g (190 mmol) of 1-(4-benzyloxy-phenyl)-4-methyl-pent-1-en-3-one prepared in Example B was effected as described in General Method 3 using 1.08 g 5% Pd over BaSO$_4$ and 1000 mL of THF under hydrogen atmosphere.

Example G 3-(4-Benzyloxy-phenyl)-1-cyclohexyl-propan-1-one

The title compound was prepared by hydrogenation of 3-(4-benzyloxy-phenyl)-1-cyclohexyl-prop-2-en-1-one (25.85 g, 84 mmol; prepared in Example C) as described in General Method 3 using 1.0 g of 5% Pd on BaSO$_4$ in 600 mL of THF at room temperature. The crude product was flash chromatographed using CH$_2$Cl$_2$:MeOH (99:1 to 98:2) to afford a gummy solid. $^1$H NMR (CDCl$_3$) δ 1.1–1.9 (m, 10 H), 2.2–2.4 (m, 1 H), 2.68–2.74 (m, 2 H), 2.79–2.85 (m, 2 H), 5.04 (s, 2 H), 6.8–6.9 (d, 2 H), 7.1–7.2 (d, 2 H), 7.3–7.5 (m, 5H).

Example H 1,5-Bis (4-benzyloxy-phenyl)-pentan-3-one Hydrogenation of 24.4 g (54.7 mmol) of 1,5-bis-(4-benzyloxy-phenyl)-penta-1,4-dien-3-one prepared in Example A was effected as described in General Method 3 using 1.0 g 5% Pd over BaSO$_4$ and 1000 mL of THF under hydrogen atmosphere. The product contained both ketone and alcohol. Therefore, the mixture was dissolved in acetone (approximately 500 mL), treated with 10 mL of 8.0N Jones reagent, and stirred overnight at room temperature. Isopropanol was added, and the mixture was filtered through Celite. The filtrate was concentrated to afford the title ketone. $^1$H NMR (CDCl$_3$) δ 2.67 (m, 4 H), 2.82 (m, 4 H), 5.03 (s, 4 H), 6.88 (d, 4 H), 7.05 (d, 4 H), 7.30–7.43 (m, 10 H).

Example I 1,5-Bis-(4-benzyloxy-3-methoxy-phenyl)-pentan-3-one

Hydrogenation of 21.5 g (42.6 mmol) of 1,5-bis-(4-benzyloxy-3-methoxy-phenyl)-penta-1,4-dien-3-one prepared in Example D was effected as described in General Method 3 using 1.0 g 5% Pd over BaSO$_4$ and 600 mL of THF under hydrogen atmosphere. The product contained both ketone and alcohol. Therefore, the mixture was dissolved in acetone (approximately 500 mL), treated with 20 mL of 8.0N Jones reagent, and stirred overnight at room temperature. Isopropanol was added, and the mixture was filtered through Celite. The filtrate was concentrated, and the residue was triturated with 1:1 hexane:EtOAc to give the title compound. $^1$H NMR (DMSO-d$_6$) δ 2.71 (m, 8 H), 3.74 (s, 6 H), 5.02 (s, 4 H), 6.66 (m, 2 H), 6.82 (br s, 2 H), 6.87 (m, 2 H), 7.29–7.43 (m, 10 H).

Example J 1,5-Bis-(3-benzyloxy-phenyl)-pentan-3-one

Hydrogenation of 5.20 g (42.6 mmol) of 1,5-bis-(3-benzyloxy-phenyl)-penta-1,4-dien-3-one prepared in Example E was effected as described in General Method 3 using 0.5 g 5% Pd over BaSO$_4$ and 150 mL of THF under hydrogen atmosphere. The product contained both ketone and alcohol, so the mixture was dissolved in acetone (approximately 200 mL) and treated with 5 mL of 8.0N Jones reagent. The mixture was stirred for 2 hours at room temperature, treated with isopropanol, and filtered through Celite. The filtrate was concentrated, and the residue was triturated with 1:1 hexane:EtOAc to give the title compound. $^1$H NMR (CDCl$_3$) δ 2.69 (m, 4 H), 2.85 (m, 4 H), 5.03 (s, 4 H), 6.58–6.81 (m, 6 H), 7.18 (m, 2 H), 7.28–7.41 (m, 10 H).

Example K 1-(4-Hydroxy-phenyl)-3-phenyl-propan-1-one

The title compound was prepared as described in General Method 3 from 1-(4-hydroxy-phenyl)-3-phenyl-prop-2-en-1-one (16.5 g, 74.0 mmol), 5% Pd on BaSO$_4$ (1.0 g), and THF (400 mL). The product was recrystallized from 50% EtOH to give the title compound, m.p. 102–105° C. $^1$H NMR (CDCl$_3$) δ 3.02 (t, 2 H), 3.22 (t, 2 H), 5.83 (s, 1 H), 6.84 (d, 2 H), 7.15–7.28 (m, 5 H), 7.88 (d, 2 H).

Example L 3-(4-Hydroxy-phenyl)-1-phenyl-propan-1-one

The title compound was prepared as described in General Method 3 from 3-(4-hydroxy-phenyl)-1-phenyl-prop-2-en-1-one (25.5 g, 113.6 mmol), 5% Pd on BaSO$_4$ (1.0 g), and THF (400 mL). The catalyst was filtered, and the filtrate was concentrated. The residue was recrystallized from 50% EtOH, to give the title compound, m.p. 118–119° C.

Example M 3-(3-Hydroxy-phenyl)-1-phenyl-propan-1-one

The title compound was prepared as described in General Method 3 from 3-(3-hydroxy-phenyl)-1-phenyl-prop-2-en-1-one (8.0 g, 35.7 mmol), 5% Pd on BaSO$_4$ (0.4 g), and THF (100 mL) at a reaction time of 2 hours. The crude product was purified by silica gel chromatography, eluting with EtOAc:hexane (10:90 to 25:75) to give the title compound, m.p. 81–83° C.

GENERAL METHOD 4

Benzyl protecting groups were removed by hydrogenation (approximately 50 psi) at room temperature using 20% Pd on C in THF. The catalyst was filtered off and the resulting phenol was used crude or purified by flash chromatography.

GENERAL METHOD 5

The appropriate alcohol (1 equivalent), and imidazole (1.2 equivalents) were added to a reaction vessel followed by CH$_2$Cl$_2$ or THF (7–10 mL per mmol of alcohol). t-Butyldimethylsilyl chloride (1.1 equivalents) was added and the reaction stirred at room temperature (3 hours to 4 days). The reaction was filtered, washed with H$_2$O and brine, dried (MgSO$_4$), and concentrated. The product was either flashed chromatographed or carried on crude.

Example N

1-[4-(2-Hydroxy-ethoxy)-phenyl]-3-phenyl-propan-1-one

A mixture of 1-(4-hydroxy-phenyl)-3-phenyl-propan-1-one from Example K (6.9 g, 30.5 mmol), and cesium carbonate (19.9 g, 61 mmol) was dissolved in dioxane (300 mL). This mixture was heated to reflux for 1 hour then treated with iodoethanol (2.85 mL, 36.5 mmol) and refluxed overnight; the reaction mixture was cooled and concentrated. The product was partitioned between EtOAc and 1N HCl. The organic layer was dried (MgSO$_4$) and concentrated to dryness. Purification by silica gel chromatography, eluting with EtOAc:hexane (30:70 to 50:50) gave the title compound, m.p. 41–43° C. $^1$H NMR (CDCl$_3$) δ 1.96 (t, 1 H), 3.02 (t, 2 H), 3.22 (t, 2 H), 3.95 (m, 2 H), 4.10 (m, 2 H), 6.92 (d, 2 H), 7.15–7.28 (m, 5 H), 7.90 (d, 2 H).

Example O

1-{4-[2-(tert-Butyl-dimethyl-silanyloxy)-ethoxy]-phenyl}-3-phenyl-propan-1-one

The title compound was prepared as described in General Method 5 using 1-[4-(2-hydroxy-ethoxy)-phenyl]-3-phenyl-propan-1-one from Example N (2.21 g, 8.2 mmol), imidazole (0.67 g, 9.8 mmol), t-butyldimethylsilyl chloride (1.36 g, 9.0 mmol) and CH$_2$Cl$_2$ (70 mL). The product was carried on crude to the next step (see Example SS.)

Example P

3-[4-(tert-Butyl-dimethyl-silanyloxy)-phenyl]-1-phenyl-propan-1-one

The title compound was prepared as described in General Method 5 using 4.53 g (20 mmol) of 3-(4-hydroxy-phenyl)-1-phenyl-propan-1-one from Example L, 1.64 g (24 mmol) of imidazole, 3.62 g (24 mmol) of t-butyldimethylsilyl chloride and 80 mL of CH$_2$Cl$_2$. The product was carried on crude to the next step (see Example TT).

Example Q

3-[3-(tert-Butyl-dimethyl-silanyloxy)-phenyl]-1-phenyl-propan-1-one

The title compound was prepared as described in General Method 5 using 4.11 g (18.2 mmol) of 3-(3-hydroxy-phenyl)-1-phenyl-propan-1-one from Example M, 1.5 g (22 mmol) of imidazole, 3.0 g (20 mmol) of t-butyldimethylsilyl chloride and 75 mL of CH$_2$Cl$_2$. The product was carried on crude to the next step (see Example UU).

Example R 4-(4-tert-Butyldimethylsilyloxy-phenyl)-2-butanone

The title compound was prepared as described in General Method 5 using 10 g (60.9 mmol) of 4-(4-hydroxyphenyl)-2-butanone, 10.1 g (67 mmol) of tert-butyldimethyl silyl chloride, 4.56 g (67 mmol) of imidazole and 150 mL of DMF. The crude product was carried on "as is" to the next step (see Example KK).

Example S 3-(4-Benzyloxyphenyl)-propanoic acid 3-(4-Hydroxyphenyl) propionic acid (15 g, 90.3 mmol) was taken in 300 mL of acetone. To it 33.8 g (197 mmol) of benzyl bromide, followed by 25 g of anhydrous K$_2$CO$_3$ were added. The reaction was kept under reflux overnight. The solvents were evaporated and poured into H$_2$O. The product was extracted into EtOAc. The organic layer was washed with brine, dried (MgSO$_4$), and concentrated.

The crude product was taken up in 100 mL of THF. To it lithium hydroxide monohydrate (7.66 g, 182 mmol) and 50 mL of MeOH were added. The reaction mixture was stirred at room temperature for 2–4 hours and then concentrated. The residue was acidified with dilute HCl, and extracted into EtOAc and CH$_2$Cl$_2$. The organic layer was dried (MgSO$_4$). Solvents were evaporated to obtain the title compound. $^1$H NMR (DMSO-d$_6$) δ 2.42 (t, 2 H), 2.67 (t, 2 H), 4.99 (s, 2 H), 6.86 (d, 2 H), 7.07 (d, 2 H), 7.27 (m, 1 H), 7.31–7.39 (m, 4H).

Example T 3-(4-Benzyloxy-phenyl)-N-methoxy-N-methyl-propionamide 3-(4-Benzyloxyphenyl) propionic acid prepared in Example S (30 g, 117 mmol) was taken up in 300 mL of thionyl chloride. The reaction was kept under reflux for 5 hours, then cooled and concentrated. The residue was dissolved in 300 mL of CH$_2$Cl$_2$ and treated with N,O-dimethylhydroxyamine hydrochloride (14.1 g, 146 mmol) and 60 mL of pyridine at 0° C. The reaction was stirred overnight. The reaction was quenched with dilute HCl and extracted into EtOAc, and the organic layer was washed with sodium bicarbonate solution and dilute HCl and dried. The organic layer was dried (MgSO$_4$) and concentrated. The residue was used further as crude reaction mixture or purified by flash silica gel column chromatography, eluting with EtOAc:hexane (1:9, then switching to 2:3).

Example U

1-(4-Benzyloxyphenyl)-heptan-3-one

The title compound was prepared by treating 3-(4-benzyloxy-phenyl)-N-methoxy-N-methyl-propionamide prepared in Example T (8.5 g, 28 mmol) with n-butyl magnesium chloride (21.4 mL, 2.0 M, 42.8 mmol) in 100 mL of THF. The reaction mixture was stirred at room temperature for 1 hour and refluxed for 3 hours. The reaction mixture was cooled to 0° C., quenched with 1N HCl, and extracted with EtOAc. After evaporation of the solvents, the crude product was purified by flash silica gel column chromatography, eluting with EtOAc:hexane (5:95, then switching to 3:7). $^1$H NMR (CDCl$_3$) δ 0.86 (t, 3 H), 1.27 (m, 2 H), 1.34 (m, 2 H), 2.33 (t, 2 H), 2.64 (t, 2 H), 2.78 (t, 2 H), 5.0 (s, 2 H), 6.85 (d, 2 H), 7.06 (d, 2 H), 7.25 (t, 1 H), 7.31–7.42 (m, 4 H).

Example V

Methanesulfonic acid 2-[4-(3-phenyl-propionyl)-phenoxy]-ethyl ester

A solution of 1-[4-(2-hydroxy-ethoxy)-phenyl]-3-phenyl-propan-1-one (prepared in Example N; 6.0 g, 22.2 mmol) and triethylamine (NEt$_3$) (4.60 mL, 33.3 mmol) in CH$_2$Cl$_2$ (50 mL) was cooled to 0° C. under a nitrogen atmosphere and treated with mesyl chloride (2.1 mL, 26.6 mmol). The mixture allowed to stir for 45 minutes, and then diluted with additional CH$_2$Cl$_2$ and washed with H$_2$O. The organic layer was dried (MgSO$_4$) and the solvent removed in vacuo to provide the title compound which was used without further purification. $^1$H NMR (DMSO-d$_6$) δ 2.90 (t, 2 H), 3.20 (s, 3 H), 3.29 (t, 2 H), 4.32–4.34 (m, 2 H), 4.52–4.55 (m, 2 H), 7.05 (d, 2 H), 7.22–7.32 (m, 5 H), 7.95 (d, 2 H).

Example W

4-{2-[4-(3-Phenyl-propionyl)-phenoxy]-ethyl}-piperazine-1-carboxylic acid tert-butyl ester

In a 12 L reaction vessel a solution of methanesulfonic acid 2-[4-(3-phenyl-propionyl)-phenoxy]-ethyl ester prepared in Example V (648 g, 1860 mmol) in DMF (800 mL) was treated with potassium iodide (625 g, 3770 mmol), diisopropylethylamine (620 mL, 3580 mmol), and piperazine (700 g, 8130 mmol). During the first 30 minutes, an exotherm was observed. The thick mixture was heated at 86° C. for 30 minutes, then cooled to room temperature. Approximately 2 kg of ice and 4 L of EtOAc were added; the mixture was stirred and the layers separated. The aqueous layer was washed with an additional 4 L of EtOAc. This process was repeated twice, and each of the organic layers was dried (MgSO$_4$) and concentrated in vacuo. The crude product (508 g) was then dissolved in 1:1 dioxane:H$_2$O (2600 mL), cooled in an ice bath and treated with sodium hydroxide (60 g, 1500 mmol) and di-t-butyldicarbonate (370 g, 1700 mmol). The mixture was stirred for 2 hours, allowed to warm to room temperature, and stirred at that temperature for 96 hours. Cold H$_2$O (4 L) and EtOAc (6 L) were added; the organic layer was dried (MgSO$_4$), and concentrated in vacuo. The resulting oil was submitted to column chromatography (20% EtOAc in hexanes) to yield the title compound. $^1$H NMR (CDCl$_3$) δ 1.46 (s, 9 H), 2.47–2.54 (m, 4 H), 2.82 (t, 2 H), 3.05 (t, 2 H), 3.25 (t, 2 H), 3.44–3.47 (m, 4 H), 4.16 (t, 2 H), 6.91 (d, 2 H), 7.19–7.32 (m, 5 H), 7.93 (d, 2 H).

Example X

3-(4-Amino-phenyl)-1-phenyl-propan-1-one

A mixture of 3-(4-nitro-phenyl)-1-phenyl-prop-2-en-1-one (24.9 g, 98.3 mmol), Raney nickel (7.0 g), MeOH (100 mL), and THF (400 mL) was shaken in a hydrogen atmosphere of 51 psi at 20° C. for 18.5 hours. The catalyst was filtered, and the filtrate was concentrated. The residue was recrystallized from 95% EtOH, to give the title compound, m.p. 76–78° C. $^1$H NMR (CDCl$_3$) δ 2.98 (t, 2 H), 3.25 (t, 2 H), 3.62 (bs, 2 H), 6.65 (d, 2 H), 7.05 (d, 2 H), 7.40–7.61 (m, 3 H), 7.96 (d, 2 H).

Example Y

N-[4-(3-Oxo-3-phenyl-propyl)-phenyl]-acetamide

Acetic anhydride (2.45 mL, 26 mmol) was added to a solution of 3-(4-amino-phenyl)-1-phenyl-propan-1-one from Example X (4.5 g, 20 mmol), NEt$_3$ (3.1 mL, 22.2 mmol), and a crystal of DMAP in CH$_2$Cl$_2$ (50 mL). The reaction mixture was stirred overnight at room temperature, then poured onto 1N HCl. The product was partitioned between CH$_2$Cl$_2$ and H$_2$O, and the organic phase was dried (MgSO$_4$) and concentrated to give the title compound. $^1$H NMR (CDCl$_3$) δ 2.16 (s, 3 H), 3.03 (t, 2 H), 3.28 (t, 2 H), 7.20 (d, 2 H), 7.37–7.60 (m, 6 H), 7.94 (d, 2 H).

Example Z

**[1R-[1α(S*),2β,5α]]-3-Hydroxy-3,5-diphenyl-pentanoic acid 2-isopropyl-5-methyl-cyclohexyl ester**

Diisopropylamine (16.4 mL, 125 mmol) in THF (375 mL) was cooled to −10° C., and 1.6 M n-butyllithium (82 mL, 130 mmol) was added over 15 minutes. The solution was stirred for 40 minutes at −10° C. then cooled to −60° C. (−) [1R-(1α,2β,5α)]-Acetic acid 2-isopropyl-5-methyl-cyclohexyl ester (26.8 mL, 125 mmol) in THF (75 mL) was added over 1 hour and the reaction stirred for 1 hour at −60° C. to −40° C. 1,3-Diphenyl-propan-1-one (21.0 g, 100 mmol) in THF (50 mL) was added over 15 minutes, and then the reaction was warmed to room temperature and stirred overnight. The reaction was poured into 1N HCl over crushed ice. The product was partitioned between EtOAc and 1N HCl, dried (MgSO$_4$) and concentrated. The product was recrystallized 3 times from hexane to give the title compound, m.p. 94–96° C. $^1$H NMR (CDCl$_3$) δ 0.38 (d, 3 H), 0.71 (d, 3 H), 0.85 (d, 3 H), 0.77–0.94 (m, 3 H), 1.18–1.40 (m, 3 H), 1.55–1.64 (m, 2 H), 1.82 (m, 1 H), 2.12 (m, 2 H), 2.31 (m, 1 H), 2.72 (m, 1 H), 2.90 (dd, 2 H), 4.56 (m, 1 H), 4.76 (s, 1 H), 7.08–7.46 (m, 10 H).

Example AA

(S)-3-Hydroxy-3,5-diphenyl-pentanoic acid

The title compound was prepared by dissolving 9.71 g (23.8 mmol) of [1R-[1α(S*),2β,5α]]-3-hydroxy-3,5-diphenyl-pentanoic acid 2-isopropyl-5-methyl-cyclohexyl ester from Example Z in 95% EtOH (80 mL). Potassium hydroxide (1.85 g, 33.0 mmol) in H$_2$O (18 mL) was added, and the reaction was heated to reflux for 5 hours, cooled and pumped to dryness under vacuum. The product was partitioned between H$_2$O and ether (Et$_2$O). The aqueous layer was decanted, acidified with 1N HCL and extracted with Et$_2$O. The solution was dried (MgSO$_4$) and concentrated to give the title compound, m.p. 134–135° C.

Example BB

Bis [3-methoxy-3-oxopropanoato (1-)-O,O'] magnesate

Monomethyl malonate (2.39 g, 20 mmol) and magnesium ethoxide (16 g, 10 mmol) in THF (50 mL) was stirred for 3 hours at room temperature. The solution was concentrated under vacuum to give the title compound. The product was carried on crude to the next step.

Example CC (S)-5-Hydroxy-3-oxo-5,7-diphenyl-heptanoic acid methyl ester

The title compound was prepared using (S)-3-hydroxy-3, 5-diphenyl-pentanoic acid from Example AA (0.7 g, 2.59 mmol), THF (30 mL), and carbonyl diimidazole (0.5 g, 3.08 mmol). The reaction was stirred for 6 hours at room temperature; bis [3-methoxy-3-oxopropanoato (1-)-O,O'] magnesate from Example BB (0.8 g, 3.10 mmol) was added, and the reaction was stirred for 3 days at room temperature. The reaction was concentrated and the residue partitioned between EtOAc and 1N HCl. The organic layer was washed with aqueous $NaHCO_3$ and brine, dried ($MgSO_4$) and concentrated. Purification by silica gel chromatography, eluting with EtOAc:hexane (20:80) gave the title compound. $^1$H NMR ($CDCl_3$) δ 2.01 (m, 1 H), 2.11 (m, 1 H), 2.24 (m, 1 H), 2.64 (m, 1 H), 2.97 (d, 1 H), 3.28 (s, 2 H), 3.30 (d, 1 H), 3.64 (s, 3 H), 4.15 (s, 1 H), 7.03–7.42 (m, 10 H).

Example DD 3-(4-Nitrophenyl)propanoic acid

A suspension of 4-nitrocinnamic acid (13.5 g, 70 mmol) in $H_2O$ (100 mL) was treated with hydroxylamine sulfate (18.5 g, 113 mmol) and hydroxylamine-o-sulfonic acid (43.5 g, 385 mmol) at 0° C. The pH was adjusted to 7.6 with 50% NaOH, and additional base was added as needed over the next 6 hours to maintain a pH of 7.6. The mixture was then filtered, and the filtrate was acidified to pH 2 with 2N $H_2SO_4$. The solids that formed were filtered, washed with $H_2O$, and recrystallized from EtOH:$H_2O$ (30 mL:150 mL) to give the title compound. $^1$H NMR ($CDCl_3$) δ 2.71 (t, 2 H), 3.03 (t, 2 H), 7.34 (d, 2 H), 8.13 (d, 2 H).

Example EE 3-(4-Nitrophenyl)propanoyl chloride 3-(4-Nitrophenyl)propanoic acid prepared in Example DD (12.5 g, 64 mmol) was suspended in $CH_2Cl_2$ (300 mL) and treated with oxalyl chloride (7.4 mL, 85 mmol) and DMF (5 drops). The solution was stirred overnight at room temperature. The solution was concentrated, and the residue was dissolved in $CH_2Cl_2$ and re-concentrated. The crude product was used as is in the next step.

Example FF 5-(4-Nitro-phenyl)-3-oxo-pentanoic acid ethyl ester

A solution of malonic acid monoethyl ester (16.9 g, 128 mmol) in dry THF (200 mL) was cooled to −78° C. under nitrogen, treated dropwise with 130 mL of isopropyl magnesium chloride (2.0 M in THF; 260 mmol), and stirred at −78° C. for 45 minutes. A solution of 3-(4-nitrophenyl) propanoyl chloride prepared in Example EE (13.5 g, 64 mmol) in dry THF (100 mL) was added dropwise. When addition was complete, the reaction mixture was stirred at −78° C. for 1 hour and then allowed to warm to room temperature, where the solution was stirred for 3 more hours. A mixture of ice (50 mL) and 3N HCl (100 mL) was added. The solution was extracted with EtOAc, and the combined extracts were washed with brine and dried ($MgSO_4$). Concentration gave the title compound. $^1$H NMR ($CDCl_3$) δ 1.21 (t, 3 H), 2.88–3.00 (m, 4 H), 3.40 (s, 2 H), 4.13 (q, 2 H), 7.32 (d, 2 H), 8.09 (d, 2 H).

Example GG 2-(4-Nitro-benzyl)-5-(4-nitro-phenyl)-3-oxo-pentanoic acid ethyl ester To a solution of 5-(4-nitro-phenyl)-3-oxo-pentanoic acid ethyl ester prepared in Example FF (14.2 g, 54 mmol) in dry THF (150 mL) was added NaH (2.43 g of a 60% dispersion in oil, 57.5 mmol), and the mixture was stirred at room temperature for 45 minutes. 4-Nitrobenzyl bromide (13.9 g, 64.3 mmol) was added all at once, and the resulting suspension was stirred overnight at room temperature. Dilute HCl (2N, 100 mL) was added. The solution was extracted with EtOAc; the extracts were combined, washed with brine, and dried ($MgSO_4$). Concentration gave a residue which was chromatographed on silica gel, eluting with 5:1 hexane:EtOAc to 1:1 hexane:EtOAc, to yield the title compound. $^1$H NMR ($CDCl_3$) δ 1.11 (t, 3 H), 2.66 (m, 1 H), 2.95 (m, 3 H), 3.21 (m, 2 H), 3.75 (t, 1 H), 4.07 (m, 2 H), 7.23 (m, 4 H), 8.05 (d, 4 H).

Example HH 1,5-Bis-(4-nitro-phenyl)-pentan-3-one

A mixture of 2-(4-nitro-benzyl)-5-(4-nitro-phenyl)-3-oxo-pentanoic acid ethyl ester obtained in Example GG (18.2 g, 45.4 mmol), 6N HCl (250 mL), and THF (50 mL) was refluxed for 18 hours and cooled to room temperature. $H_2O$ was added, and the solution was extracted with EtOAc. The extracts were combined, washed with brine, dried ($MgSO_4$), and concentrated. The residue was triturated with $Et_2O$ and filtered to give the title compound. $^1$H NMR ($CDCl_3$) δ2.73 (t, 4 H), 2.96 (t, 4 H), 7.29 (d, 4 H), 8.09 (m, 4 H).

Example II 1,5-Bis (4-amino-phenyl)-pentan-3-one

A mixture of 1,5-bis-(4-nitro-phenyl)-pentan-3-one from Example HH (9.00 g, 27.4 mmol), 5% Pd on $BaSO_4$ (0.7 g), and THF (600 mL) was shaken in a hydrogen atmosphere of 52 psi at 26° C. for 17 hours. The catalyst was filtered, and the filtrate was concentrated. The residue was chromatographed on silica gel, eluting with 4% MeOH in $CH_2Cl_2$, to give the title compound. $^1$H NMR ($CDCl_3$) ε2.60 (m, 4 H), 2.74 (m, 4 H), 3.45 (bs, 4 H), 6.56 (m, 4 H), 6.91 (m, 4 H).

Example JJ

Bis (1,1-dimethylethyl) [(3-oxo-1,5-pentanediyl)di-4,1-phenylene] biscarbamate

To a solution of the ketone from Example II (3.1 g, 11 mmol) in THF (100 mL) was added a solution of di-t-butyl dicarbonate (6.3 g, 29 mmol) in THF (50 mL). The reaction mixture was stirred at 55° C. for 5 hours, then cooled to room temperature and concentrated. The residue was partitioned between EtOAc and $H_2O$, and the organic phase was dried ($MgSO_4$) and concentrated. The residue was chromatographed on silica gel, eluting with 2:1 hexane:EtOAc, to give the title compound. $^1$H NMR ($CDCl_3$) δ 1.46 (s, 18 H), 2.67 (s, 8 H), 7.04 (d, 4 H), 7.31 (d,4H),9.21 (bs,2 H).

GENERAL METHOD 6

Methyl acetoacetate was added drop wise to a slurry of hexane washed sodium hydride in anhydrous THF at 0° C. and the reaction stirred at 0° C. (15 minutes to 3 hours). n-Butyl lithium was then added at 0° C. and the reaction stirred at 0° C. (15 minutes to 24 hours). A solution of the requisite ketone in THF was added, and the reaction mixture was stirred at 0° C. to room temperature for 15 minutes to 24 hours. To the reaction mixture was added acetic acid [or dilute HCl or saturated ammonium chloride (NH$_4$Cl)] with stirring, and the THF was removed on a rotoevaporator. The viscous reaction mixture was partitioned between H$_2$O and EtOAc. After separation of the layers, the aqueous layer was again extracted with EtOAc. The combined organic extracts were dried (MgSO$_4$) and concentrated. The aldol intermediates were either flashed chromatographed or taken on crude.

GENERAL METHOD 7

The aldol intermediate was dissolved in THF (1 volume) and treated with 9–10 volumes of NaOH (0.1N to 1.0N). The reaction was stirred from 1 hour to 24 hours at room temperature. The base solution was extracted with Et$_2$O and then cooled to 0° C. The mixture was acidified to pH 4–5 using HCl (0.1N to 6N) or acetic acid. On occasion the product could be isolated by filtration. Alternatively the acidified extracts were extracted with EtOAc. The organic extracts were combined, dried (MgSO$_4$) and concentrated. Purification was accomplished by trituration from Et$_2$O or flash chromatography.

GENERAL METHOD 8

The appropriate silanyloxy compound (1 equivalent) was added to a reaction vessel followed by THF (3–5 mL per mmol of silanyloxy compound). This solution was treated with tetrabutylammonium fluoride (1.2–2.0 equivalents) and stirred at room temperature (1 hour to 1 day). The product was partitioned between EtOAc and 1N HCl. The organic layer was dried (MgSO$_4$) and concentrated. The product was either flashed chromatographed or carried on crude.

Example KK

4-Hydroxy-6-[2-(4-hydroxy-phenyl)-ethyl]-6-methyl-5,6-dihydro-pyran-2-one

The title compound was prepared as described in General Method 6 using 16.9 g (60.9 mmol) of 4-(4-tert-butyldimethylsilyloxyphenyl)-2-butanone (prepared in Example R), 7.32 g (183 mmol) of 60% NaH dispersion in mineral oil, 21.2 g (183 mmol) of methyl acetoacetate, 114 mL (1.64 M, 183 mmol) of n-butyllithium and 360 mL of THF. The reaction mixture was quenched with 0.1N HCl and the product was extracted into EtOAc. The organic layer was dried (MgSO$_4$) and the solvents were evaporated.

The above crude product was cyclized as described in General Method 7 using the crude aldol product, 137 mL of THF and 1370 mL of 0.2N NaOH. The product was purified by flash silica gel chromatography. $^1$H-NMR (DMSO-d$_6$) δ1.31 (s, 3 H), 1.8 (m, 2 H), 2.31 (d of ABX q, 1 H), 2.42–2.5 (m, 2 H), 2.54 (d of ABX q, 1 H), 4.92 (s, 1 H), 6.61 (d, 2 H), 6.92 (d, 2 H), 9.14 (br s, 1 H).

Example LL

4-Hydroxy-6-[2-(4-hydroxy-phenyl)-ethyl]-6-isopropyl-5,6-dihydro-pyran-2-one

The title compound was prepared as described in General Method 6 using 40 g (142 mmol) of 1-(4-benzyloxyphenyl)-4-methyl-pentan-3-one (prepared in Example F ), 41.2 g (355 mmol) of methyl acetoacetate, 14.2 g (355 mmol) of 60% NaH dispersion in mineral oil, 216 mL (1.64 M, 355 mmol) of n-butyllithium and 700 mL of THF. The reaction mixture was quenched with 0.1N HCl and the product was extracted into EtOAc. The organic layer was dried (MgSO$_4$), and the solvents were evaporated.

The above crude product was cyclized as described in General Method 7 using 319 mL of THF and 3191 mL of 0.2N NaOH. The product was obtained by acidification of the reaction mixture with 0.1N HCl. The precipitate thus obtained was filtered and crystallized from MeOH. $^1$H-NMR (DMSO-d$_6$) δ 0.83 (d, 3 H), 0.86 (d, 3 H), 1.81 (m, 2 H), 2.05 (m, 1 H), 2.25 (d of ABX q, 1 H), 2.39–2.5 (m, 2 H), 2.53 (d of ABX q, 1 H), 4.92 (s, 1 H), 5.0 (s, 2 H), 6.86 (d, 2 H), 7.03 (d, 2 H), 8.22–8.29 (m, 1 H), 8.3–8.39 (m, 4 H).

The title compound was prepared as described in General Method 4 using 30 g of 6-[2-(4-benzyloxy-phenyl)-ethyl]-4-hydroxy-6-isopropyl-5,6-dihydro-pyran-2-one (prepared in the paragraph above), 3 g of 20% Pd over charcoal and 600 mL of THF. The crude compound was purified by silica gel filtration. $^1$H NMR (DMSO-d$_6$) δ 0.83 (d, 3 H), 0.86 (d, 3 H), 1.78 (m, 2 H), 2.06 (m, 1 H), 2.25 (d of ABX q, 1 H), 2.39 (m, 2 H), 2.53 (d of ABX q, 1 H), 4.89 (s, 1 H), 6.6 (d, 2 H), 6.89 (d, 2 H), 9.1 (br s, 1 H).

Example MM

6-Butyl-4-hydroxy-6-[2-(4-hydroxy-phenyl)-ethyl]-5,6-dihydro-pyran-2-one

The title compound was prepared according the General Method 6 using 4.0 g (13 mmol) of 1-(4-benzyloxyphenyl)-heptan-3-one (prepared in Example U), 6.3 g (54 mmol) of methyl acetoacetate, 2.2 g (54 mmol) of 60% NaH dispersion in mineral oil, 33 mL (1.64 M, 54 mmol) of n-butyllithium and 110 mL of THF. The reaction mixture was quenched with 0.1 NH$_4$Cl, and the mixture was worked up in the normal fashion.

The above crude product was cyclized as described in General Method 7 using the crude aldol product, 30 mL of THF and 304 mL of 0.2N NaOH. The product was purified via flash silica gel chromatography, eluting with EtOAc:hexane (1:4, then switching to 3:7).

The title compound was prepared by debenzylation of 1.7 g (4.5 mmol) of 6-[2-(4-benzyloxy-phenyl)-ethyl]-6-butyl-4-hydroxy-5,6-dihydro-pyran-2-one (prepared in the paragraph above) using 0.15 g of 20% Pd on carbon and 75 mL of THF under hydrogen atmosphere as described in General Method 4. $^1$H NMR (DMSO-d$_6$) δ 0.80 (t, 3 H), 1.2 (m, 4 H), 1.61 (m, 4 H), 1.81 (m, 2 H), 2.38 (d of ABX q, 1 H), 2.49 (d of ABX q, partially obscured by DMSO, 1 H), 4.89 (s, 1 H), 6.6 (d, 2 H), 6.91 (d, 2 H), 9.08 (s, 1 H), 11.25 (s, 1 H).

Example NN

6-Cyclohexyl-4-hydroxy-6-[2-(4-hydroxy-phenyl)-ethyl]-5,6-dihydro-pyran-2-one

The title compound was prepared as described in General Method 6 using 11.6 g (99.9 mmol) of methyl acetoacetate, 4.19 g (105 mmol) of NaH (60% dispersion in oil), 64.0 mL (102 mmol) of 1.6 M n-butyl lithium in hexane, 16.1 g (49.9 mmol) of 3-(4-benzyloxy-phenyl)-1-cyclohexyl-propan-1-one (prepared in Example G) and 550 mL of THF. After addition of the ketone, the reaction was stirred for 120 minutes at 0° C., then 1 hour at room temperature. The reaction was quenched with acetic acid (12 mL) and worked up in the usual manner. The crude product was carried on without further purification.

The compound prepared above was hydrogenated as described in General Method 4 using 2.0 g of 20% Pd on carbon in 400 mL of tetrahydrofuran at room temperature. The crude product was carried on without purification.

Crude 5-cyclohexyl-5-hydroxy-7-(4-hydroxy-phenyl)-3-oxo-heptanoic acid methyl ester (prepared in the previous paragraph) was dissolved in tetrahydrofuran (100 mL) and treated with 0.2N NaOH (900 mL) as described in General Method 7. The reaction was stirred for 3 hours at room temperature and then worked up as usual. The organic extracts obtained were combined, dried (MgSO$_4$) and concentrated. Purification was accomplished by flash chromatography using CH$_2$Cl$_2$:MeOH (99:1 to 98:2) to give the desired product as a solid, m.p. 52–58° C. $^1$H NMR (CDCl$_3$) δ 1.0–1.9 (m, 12 H), 1.9–2.1 (m, 1 H), 2.5–2.7 (m, 3 H), 2.8 (d, 1 H), 3.4 (s, 2 H), 6.75 (d, 2 H), 7.05 (d, 2 H).

Example OO (1,1-Dimethylethyl)[(3,6-dihydro-4-hydroxy-6-oxo-2H-pyran-2,2-diyl)bis[2,1-ethanediyl-(4,1-phenylene)]] biscarbamate The title compound was prepared from bis (1,1-dimethylethyl) [(3-oxo-1,5-pentanediyl)di-4,1-phenylene] biscarbamate obtained in Example JJ (2.8 g, 6.0 mmol), methyl acetoacetate (3.5 g, 30 mmol), 60%NaH (1.45 g, 36 mmol), and n-butyllithium (27 mL of 1.35 M, 36 mmol) in THF as described in General Method 6. The product was carried on crude to the next step.

The residue obtained above (3.4 g, 6.0 mmol) was cyclized using 1N NaOH (750 mL) and THF (75 mL) as described in General Method 7. After acidification to pH 4.5, the solution was extracted with EtOAc. The extract was washed with brine, dried, concentrated, and chromatographed on silica gel, eluting with 1:1 hexane:EtOAc, to give the title compound. $^1$H NMR (DMSO-d$_6$) δ 1.40 (s, 18 H), 1.87 (m, 4 H), 2.44 (m, 4 H), 4.93 (s, 1 H), 7.01 (d, 4 H), 7.29 (d, 4 H), 9.18 (br s, 2 H).

Example PP

4-Hydroxy-6,6-bis-[2-(4-hydroxy-phenyl)-ethyl]-5,6-dihydro-pyran-2-one

The title compound was prepared as described in General Method 6 using 11.2 g (25 mmol) of 1,5-bis (4-benzyloxy-phenyl)-pentan-3-one (prepared in Example H), 1.0 g (25 mmol) of 60% NaH dispersion in mineral oil, 2.88 g (25 mmol) of methyl acetoacetate, 15.6 mL (1.6 M, 25 mmol) of n-butyllithium and 300 mL of THF. The reaction mixture was stirred for 12 hours at room temperature, quenched with aqueous NH$_4$Cl, and worked up in the usual manner.

The above crude product was cyclized as described in General Method 7 using 20 mL of THF and 200 mL of 0.1N NaOH. After 14 hours the reaction was partially concentrated, then extracted with Et$_2$O. The aqueous layer was chilled, treated with 50% aqueous acetic acid, and extracted with EtOAc. The organics were washed with brine and dried (Na$_2$SO$_4$). Concentration of the solution yielded a residue which was suspended in Et$_2$O, and the resultant solid filtered and dried to give the desired dihydropyrone. $^1$H NMR (DMSO-d$_6$) δ 1.88–2.00 (m, 4 H), 2.52–2.59 (m, 4 H), 2.69 (s, 2 H), 4.99 (s, 1 H), 5.05 (s, 4 H), 6.88–6.93 (m, 4 H), 7.07–7.13 (m, 4 H), 7.29–7.44 (m, 10 H).

The benzyl groups were removed as described in General Method 4, using 7.5 g (14 mmol) of the material obtained in the previous paragraph, 1.0 g of 20% Pd on carbon, 50 mL of THF, and 50 mL of MeOH. Concentration of the filtrate gave the title compound. $^1$H NMR (DMSO-d$_6$) δ 1.87 1.95 (m, 4 H), 2.53 (m, partially obscured by DMSO, 4 H), 2.65 (s, 2 H), 4.98 (s, 1 H), 6.65 (d, 4 H), 6.98 (d, 4 H), 9.15 (s, 2 H), 11.38 (s, 1 H).

Example QQ

4-Hydroxy-6,6-bis-[2-(4-hydroxy-3-methoxy-phenyl)-ethyl]-5,6-dihydro-pyran-2-one The title compound was prepared as described in General Method 6 using 3.72 g (7.3 mmol) of 1,5-bis-(4-benzyloxy-3-methoxy-phenyl)-pentan-3-one (prepared in Example I), 0.32 g (8.0 mmol) of 60% NaH dispersion in mineral oil, 0.85 g (7.3 mmol) of methyl acetoacetate, 5.0 mL (1.6 M, 8.0 mmol) of n-butyllithium and 100 mL of THF. The reaction mixture was stirred for 12 hours at room temperature and worked up in the usual manner.

The above crude product was cyclized as described in General Method 7 using 10 mL of THF and 100 mL of 0.1N NaOH. After 14 hours the reaction was partially concentrated, then extracted with Et$_2$O. The aqueous layer was chilled, acidified, and worked up as described in General Method 6. The residue which was obtained was chromatographed, eluting with (1:1 CH$_2$Cl$_2$:EtOAc plus 2% MeOH), to give 6,6-bis-[2-(4-benzyloxy-3-methoxy-phenyl)-ethyl]-5,6-dihydro-4-hydroxy-pyran-2-one. $^1$H NMR (DMSO-d$_6$) δ 1.93–2.00 (m, 4 H), 2.52–2.59 (m, 4 H), 2.73 (br s, 2 H), 3.76 (s, 6 H), 4.98 (s, 1 H), 5.02 (s, 4 H), 6.68 (m, 2 H), 6.83 (br s, 2 H), 6.91 (d, 2 H), 7.28–7.44 (m, 10 H), 11.40, (s, 1 H).

The benzyl groups were removed as described in General Method 4, using 0.90 g (1.5 mmol) of the material obtained in the previous paragraph, 0.10 g of 20% Pd on carbon, and 75 mL of THF. Concentration of the filtrate gave the title compound. $^1$H NMR (DMSO-d$_6$) δ 1.90–1.98 (m, 4 H), 2.50–2.57 (m, partially obscured by DMSO, 4 H), 3.74 (s, 6 H), 4.99 (s, 1 H), 6.58 (m, 2 H), 6.65 (d, 2 H), 6.75 (s, 2 H), 8.69 (s, 2 H), 11.38 (s, 1 H).

Example RR

N-{4-[2-(4-Hydroxy-6-oxo-2-phenyl-3,6-dihydro-2H-pyran-2-yl)-ethyl]-phenyl}-acetamide Methyl acetoacetate (4.5 mL, 41.7 mmol) was added dropwise to a slurry of 60% sodium hydride (1.75 g, 43.7 mmol) in THF (135 mL) at 0° C. After stirring 15 minutes, n-butyllithium (21 mL of 2.1 M, 44.1 mmol) was added and the reaction stirred an additional 15 minutes at 0° C. N-[4-(3-Oxo-3-phenyl-propyl)-phenyl]-acetamide, prepared in Example Y (5.3 g, 19.8 mmol) in THF (15 mL) was added in one portion and the reaction allowed to warm to room temperature over 4 hours. H$_2$O was added and the reaction allowed to stir overnight. The mixture was extracted with Et$_2$O and the aqueous layer acidified with 1N HCl. The precipitate was filtered, then washed with EtOAc to give the title compound, m.p. 155–160° C. $^1$H NMR (DMSO-d$_6$) δ 2.0 (s, 3 H), 2.17 (m, 2 H), 2.50 (m, 2 H), 3.02 (dd, 2 H), 4.88 (s, 1 H), 6.99 (d, 2 H), 7.25–7.50 (m, 7 H), 9.81 (s, 1 H), 11.50 (s, 1 H).

Example SS

6-{4-[2-(tert-Butyl-dimethyl-silanyloxy)-ethoxy]-phenyl}-4-hydroxy-6-phenethyl-5,6-dihydro-pyran-2-one The title compound was prepared as described in General Methods 6 and 7 using 2.5 mL (23.2 mmol) of methyl acetoacetate, 0.96 g (24 mmol) of 60% sodium hydride, 15 mL (24 mmol) of 1.6 M n-butyllithium, 4.5 g (11.7 mmol) of 1-{4-[2-(tert-butyl-dimethyl-silanyloxy)-ethoxy]-phenyl}-3-phenyl-propan-1-one from Example O and 100 mL of THF. Purification by silica gel chromatography, eluting with EtOAc:hexane (25:75 to 50:50) gave the title compound. $^1$H NMR (CDCl$_3$) δ 0.0 (s, 6 H), 0.81 (s, 9 H), 2.17 (m, 2 H), 2.42 (m, 1 H), 2.63 (m, 1 H), 2.85 (dd, 2 H), 3.22 (dd, 2 H), 3.86–3.96 (m, 4 H), 6.80–7.19 (m, 9 H).

Example TT

4-Hydroxy-6-[2-(4-hydroxy-phenyl)-ethyl]-6-phenyl-5,6-dihydro-pyran-2-one

The title compound was prepared as described in General Method 6 using 4.3 mL (40 mmol) of methyl acetoacetate, 1.64 g (41 mmol) of 60% sodium hydride, 25.6 mL (41 mmol) of 1.6 M n-butyllithium, 6.81 g (20 mmol) of 3-[4-(tert-butyl-dimethyl-silanyloxy)-phenyl]-1-phenyl-propan-1-one (from Example P) and 200 mL of THF. The product was carried on crude to the next step.

The title compound was prepared as described in General Method 7 and General Method 8 using 9.05 g (20 mmol) of 7-[4-(tert-butyl-dimethyl-silanyloxy)-phenyl]-5-hydroxy-3-oxo-5-phenyl-heptanoic acid methyl ester from the previous paragraph, 40 mL (40 mmol) of 1 M tetrabutylammonium fluoride and 20 mL of THF. The resultant crude material was combined with 800 mL of 0.1N NaOH:THF (9:1). After workup the product was purified by silica gel chromatography, eluting with MeOH:CH$_2$Cl$_2$ (5:95 to 10:90) gave the title compound. $^1$H NMR (CDCl$_3$) δ 2.24 (m, 2 H), 2.42 (m, 1H), 2.63 (m, 1 H), 2.96 (dd, 2 H), 3.33 (dd, 2 H), 5.17 (bs, 1 H), 6.73 (d, 2 H), 6.94 (d, 2 H), 7.33–7.45 (m, 5 H).

Example UU

4-Hydroxy-6-[2-(3-hydroxy-phenyl)-ethyl]-6-phenyl-5,6-dihydro-pyran-2-one

The title compound was prepared as described in General Methods 6 and 7 using 2.4 mL (22.2 mmol) of methyl acetoacetate, 1.02 g (25.5 mmol) of 60% sodium hydride, 16 mL (25.6 mmol) of 1.6 M n-butyllithium, 6.2 g (18.2 mmol) of 3-[3-(tert-butyl-dimethyl-silanyloxy)-phenyl]-1-phenyl-propan-1-one from Example Q and 180 mL of THF. After standard work-up, the crude aldol product was dissolved in THF (60 mL), treated with 0.2N NaOH (500 mL), and stirred at room temperature. The title compound was isolated via the normal procedure. $^1$H NMR (CDCl$_3$) δ 2.21 (m, 2 H), 2.38 (m, 1 H), 2.61 (m, 1 H), 2.93 (dd, 2 H), 3.28 (dd, 2 H), 6.54–6.65 (m, 3 H), 7.06 (m, 1 H), 7.28–7.40 (m, 6 H).

Example VV (S)-4-Hydroxy-6-phenethyl-6-phenyl-5,6-dihydro-pyran-2-one

The title compound was prepared as described in General Method 7 using 0.46 g (1.41 mmol) of (S)-5-hydroxy-3-oxo-5,7-diphenyl-heptanoic acid methyl ester from Example CC and 0.1N NaOH (450 mL). The reaction was stirred for 2 hours at room temperature then extracted with Et$_2$O. The aqueous layer was decanted and acidified with 1N HCL, extracted with EtOAc, dried (MgSO$_4$), and concentrated. Purification by silica gel chromatography, eluting with MeOH:CH$_2$Cl$_2$ (2:98) gave the title compound. $^1$H NMR (CDCl$_3$) δ 2.25 (m, 2 H), 2.45 (m, 1 H), 2.70 (m, 1 H), 2.92 (dd, 2 H), 3.30 (dd, 2 H), 7.04–7.41 (m, 10 H).

Example WW 4-(2-{[4-Hydroxy-6-oxo-2-phenethyl-3,6-dihydro-2H-pyran-2-yl]-phenoxy}ethyl)-piperazine-1-carboxylic acid tert-butyl ester The title compound was prepared as described in General Method 6 using 37.2 g (320 mmol) of methyl acetoacetate, 13.2 g (330 mmol) of sodium hydride (60% dispersion in oil), 200 mL of 1.6 M n-butyllithium (320 mmol), 70.2 g (160 mmol) of 4-{2-[4-(3-phenyl-propionyl)-phenoxy]-ethyl}-piperazine-1-carboxylic acid tert-butyl ester prepared in Example W, and 400 mL of THF. After addition of the ketone, the reaction mixture was stirred at 1 hour at 0° C. and then quenched with a 50:50 mixture of acetic acid:H$_2$O. Standard work-up gave the crude aldol product which was carried on without purification.

The cyclization was effected as described in General Method 7 using the product obtained from the previous paragraph (160 mmol), 200 mL of THF, and 1.0 L of 0.2N NaOH. The mixture was stirred at room temperature for 30 minutes and then worked up as usual. The residue obtained was chromatographed on silica gel, eluting with CHCl$_3$ (switching to 3% MeOH in CHCl$_3$) to yield the title compound. $^1$H NMR (CDCl$_3$) δ 1.45 (s, 9 H), 2.20–2.28 (m, 2 H), 2.53 (m, 6 H), 2.82 (m, 2 H), 2.88 (m, 2 H), 3.28 (m, 2 H), 3.45 (m, 4 H), 4.12 (m, 2 H), 6.90 (d, 2 H), 7.09 (d, 2 H), 7.16–7.28 (m, 5 H).

Example XX

4-Hydroxy-6,6-bis-[2-(3-hydroxy-phenyl)-ethyl]-5,6-dihydro-pyran-2-one

A solution of 3.3 mL of diisopropylamine (23.5 mmol) in dry THF (500 mL) was cooled to 0° C. under nitrogen, treated with 14.3 mL of 1.64 M n-butyllithium (22.8 mmol), and stirred at 0° C. for 25 minutes. To this solution was added 1.2 mL (11.1 mmol) of methyl acetoacetate, and the mixture was stirred for 30 minutes. The solution was then cooled to −78° C. A solution of 5.00 g (11.1 mmol) of 1,5-bis-(3-benzyloxy-phenyl)-pentan-3-one (prepared in Example J) dissolved in dry THF (100 mL) was added dropwise, and the mixture was stirred at low temperature for 3 hours. Dilute acetic acid (2 equivalents) was added, and the mixture was extracted with EtOAc. The extracts were dried (MgSO$_4$) and concentrated. The residue that was obtained was dissolved in THF (250 mL), treated with 0.1N NaOH (500 mL), and stirred overnight at room temperature. The mixture was cooled in an ice bath, quenched with 50% acetic acid, and extracted with EtOAc. The organic layer was dried (MgSO$_4$) and concentrated. The residue was chromatographed on silica gel, eluting with MeOH:CH$_2$Cl$_2$ (2:98), to give 6,6-bis-[2-(3-benzyloxy-phenyl)-ethyl]-5,6-dihydro-4-hydroxy-pyran-2-one. $^1$H NMR (DMSO-d$_6$) δ 1.93 (m, 4 H), 2.56 (m, 4 H), 3.35 (s, partially obscured by H$_2$O, 2 H), 4.99 (s, 1 H), 5.02 (s, 4 H), 6.72–6.78 (m, 4 H), 6.82 (br s, 2 H), 7.14 (t, 2 H), 7.26–7.39 (m, 10 H).

The benzyl groups were removed as described in General Method 4, using the 6,6-bis-[2-(3-benzyloxy-phenyl)-ethyl]-5,6-dihydro-4-hydroxy-pyran-2-one prepared in the previous paragraph, 1.0 g of 20% Pd on carbon, 50 mL of THF, and 50 mL of MeOH. Concentration of the filtrate gave the title compound. $^1$H NMR (DMSO-d$_6$) δ 1.91–2.00 (m, 4 H), 2.53 (m, partially obscured by DMSO, 4 H), 2.59 (s, 2 H), 5.00 (s, 1 H), 6.56–6.63 (m,6 H), 7.06 (t, 2 H), 9.27 (s, 2 H), 11.42 (br s, 1 H).

Example YY

4-Bromo-2-t-butyl-5-methylphenol

To a solution of 2-t-butyl-5-methylphenol (24.6 g, 150 mmol) in CCl$_4$ (100 mL) at 0° C. was added a solution of bromine (7.7 mL, 150 mmol) in CCl$_4$ (100 mL) over a 4 hour period. The mixture was stirred at room temperature for 30 minutes and then diluted with H$_2$O. The organic phase was separated, washed with saturated sodium bisulfite and brine, and dried (MgSO$_4$). Concentration gave a residue which was chromatographed on silica gel, eluting with 6:1 hexanes:EtOAc, to give the title compound. $^1$H NMR (CDCl$_3$) δ 1.34 (s, 9 H), 2.24 (s, 3 H), 5.20 (s, 1 H), 6.54 (s, 1 H), 7.32 (s, 1 H).

Example ZZ

1-Bromo-5-tert-butyl-4-(2-methoxy-ethoxymethoxy)-2-methyl-benzene

A solution of 4-bromo-2-t-butyl-5-methylphenol from Example YY (32.8 g, 135 mmol) in THF (150 mL) was treated portionwise with NaH (6.5 g of a 60% dispersion in oil, 162 mmol), and the mixture was stirred at room temperature for 1 hour. To the suspension was added 2-methoxyethoxymethyl chloride (18 mL, 158 mmol) all at once, and the resulting mixture was stirred at room temperature overnight. $H_2O$ (200 mL) was added slowly, followed by EtOAc (200 mL). The organic layer was separated, washed with $H_2O$, and dried ($MgSO_4$). Concentration gave the title compound. $^1$H NMR ($CDCl_3$) δ 1.31 (s, 9 H), 2.29 (s, 3 H), 3.36 (s, 3 H), 3.55 (m, 2 H), 3.78 (m, 2 H), 5.25 (s, 2 H), 7.02 (s, 1 H), 7.33 (s, 1 H).

Example AAA 5-tert-Butyl-4-(2-methoxy-ethoxymethoxy)-2-methyl benzoic acid

A solution of 1-bromo-5-tert-butyl-4-(2-methoxy-ethoxymethoxy)-2-methyl-benzene from Example ZZ (44.7 g, 135 mmol) in dry THF was cooled to −78° C. under nitrogen and treated with 1.6 M n-butyllithium (93 mL, 149 mmol). The solution was stirred at −78° C. for 45 minutes and then poured over crushed dry ice. The mixture was allowed to warm to room temperature. $Et_2O$ (100 mL) and 2N NaOH (200 mL) were added; the organic layer was separated and re-extracted with 2N NaOH. The aqueous layers were combined, acidified to pH 2 with 6N HCl, and extracted with EtOAc. The combined organic extracts were washed with brine, dried ($MgSO_4$), and concentrated to give the title compound. $^1$H NMR ($CDCl_3$) δ 1.35 (s, 9 H), 2.57 (s, 3 H), 3.37 (s, 3 H), 3.57 (m, 2 H), 3.81 (m, 2 H), 5.35 (s, 2 H), 6.98 (s, 1 H), 8.01 (s, 1 H).

Example BBB 5-tert-Butyl-4-hydroxy-2-methylbenzoic acid methyl ester

A solution of 5-tert-butyl-4-(2-methoxy-ethoxymethoxy)-2-methyl benzoic acid from Example AAA (20.9 g, 70.5 mmol), MeOH (150 mL), and $H_2SO_4$ (10 mL) was refluxed for 5 hours and stirred overnight at room temperature. The mixture was concentrated by half, diluted with $H_2O$, and extracted with EtOAc. The combined extracts were washed with brine, dried ($MgSO_4$), and concentrated to give the title compound. $^1$H NMR ($CDCl_3$) δ 1.36 (s, 9 H), 2.48 (s, 3 H), 3.82 (s, 3 H), 6.48 (s, 1 H), 7.87 (s, 1 H).

Example CCC 5-tert-Butyl4-dimethylthiocarbamoyloxy-2-methyl-benzoic acid methyl ester To a solution of 5-tert-butyl-4-hydroxy-2-methylbenzoic acid methyl ester from Example BBB (15.1 g, 68 mmol) in DMF (150 mL) was added NaH (3.3 g of a 60% dispersion, 82 mmol), and the mixture was stirred at room temperature for 1 hour. N,N-Dimethylthiocarbamoyl chloride (10.1 g, 82 mmol) was added all at once; the reaction mixture was stirred at 55° C. for 36 hours and then cooled to room temperature. $H_2O$ (200 mL) was added, and the solution was extracted with EtOAc. The combined extracts were washed with 1N NaOH, 1N HCl, and brine. The organic phase was dried ($MgSO_4$) and concentrated. The residue was chromatographed on silica gel, eluting with 6:1 hexane:EtOAc, to give the title compound. $^1$H NMR ($CDCl_3$) δ 1.37 (s, 9 H), 2.55 (s, 3 H), 3.39 (s, 3 H), 3.49 (s, 3 H), 3.89 (s, 3 H), 6.90 (s, 1 H), 8.01 (s, 1 H).

Example DDD 5-tert-Butyl-4-dimethylcarbamoylsulfanyl-2-methyl-benzoic acid methyl ester 5-tert-Butyl-4-dimethylthiocarbamoyloxy-2-methyl-benzoic acid methyl ester from Example CCC (13.4 g, 43.3 mmol) was heated neat to 280° C. for 2 hours and cooled to room temperature. The residue was triturated with $Et_2O$:hexane to give the title compound. $^1$H NMR ($CDCl_3$) δ 1.43 (s, 9 H), 2.49 (s, 3 H), 3.05 (br d, 6 H), 3.85 (s, 3 H), 7.32 (s, 1 H), 7.97 (s, 1 H).

Example EEE (5-tert-Butyl-4-mercapto-5-methyl-phenyl)-methanol

To a stirred solution of 12.2 g (39.4 mmol) of 5-tert-butyl-4-dimethylcarbamoylsulfanyl-2-methyl-benzoic acid methyl ester (prepared in Example DDD) in toluene (140 mL) cooled to −78° C. under nitrogen was added 1.0 M $DIBAL/CH_2Cl_2$ (236.6 mL), dropwise over a 2.5 hour period. The reaction mixture was stirred an additional 30 minutes at −78° C. following addition, then at 0° C. for 1 hour. Saturated aqueous citric acid solution (approximately 600 mL) was added very slowly and carefully. The mixture was then extracted twice with EtOAc; the organic phases were combined, washed with brine, dried ($MgSO_4$), filtered and concentrated to give the title compound. $^1$H NMR ($CDCl_3$) δ 1.47 (s, 9 H), 2.27 (s, 3 H), 3.57 (s, 1 H), 4.63 (s, 2 H), 7.06 (s, 1 H), 7.32 (s, 1 H).

Example FFF

Toluene-4-thiosulfonic acid S-(2-tert-butyl-4-hydroxymethyl-5-methyl-phenyl) ester To a solution of p-toluenesulfonyl bromide (12.0 g, 50.9 mmol), $NEt_3$ (5.15 g, 50.9 mmol), and $CCl_4$ (325 mL) at 0° C. was added a solution of the product from Example EEE (8.93 g, 42.4 mmol) in $CCl^4$ (510 mL) in a very slow, dropwise fashion. Addition was complete in 11 hours. The reaction was allowed to warm to room temperature overnight. $H_2O$ and $CHCl_3$ were added; the organic layer was separated, washed with saturated aqueous $NH_4Cl$ and brine, and dried ($MgSO_4$). Concentration gave a residue which was chromatographed on silica gel, eluting with hexane:EtOAc (4:1 then 1:1), to give the title compound. $^1$H NMR ($CDCl_3$) δ 1.22 (s, 9 H), 2.18 (s, 3 H), 2.38 (s, 3 H), 4.67 (s, 2 H), 7.20 (m, 3 H), 7.43 (s, 1 H), 7.48 (d, 2 H).

Example GGG 5-tert-Butyl-2-methyl-4-thiocyanato-phenol

In a 5 L flask were placed 350 g (2.13 mol) of 5-tert-butyl-2-methyl-phenol, sodium thiocyanide (555 g, 6.85 mol) and MeOH (1400 mL), and the resulting mixture cooled to 7° C. A solution of sodium bromide (214 g, 2.08 mol), bromine (126 mL, 2.38 mol), and MeOH (1800 mL) was added slowly and the temperature raised to 40° C. over a period of 30 minutes. The precipitants were filtered and the filtrate concentrated by half. Saturated sodium carbonate (3.5 L) and $H_2O$ (4.5 L) were added. The mixture was extracted with EtOAc (3 L), and the organic layers were combined and concentrated. To this residue were added t-butylmethyl ether (500 mL) and hexanes (500 mL), and the mixture was allowed to stand for 17 hours at −5° C. The precipitants were filtered to give the title compound, m.p. 99–102° C. $^1$H NMR ($CDCl_3$) δ 1.46 (s, 9 H), 2.22 (s, 3 H), 5.01 (s, 1 H), 6.89 (s, 1 H), 7.49 (s, 1 H).

Example HHH tert-Butyl-(5-tert-butyl-2-methyl-4-thiocyanato-phenoxy)-dimethyl-silane A solution of 2.0 g (9.0 mmol) of 5-tert-butyl-2-methyl-4-thiocyanato-phenol (prepared in Example GGG), imidazole (0.800 g, 11.8 mmol) and DMF (10 mL) was treated with t-butyldimethylsilylchloride (1.64 g, 10.9 mmol) and stirred overnight. The mixture was diluted with saturated sodium bicarbonate and the mixture extracted with hexanes. The hexane layers were combined, dried ($Na_2SO_4$), and the solvent removed in vacuo to yield the title compound. $^1$H NMR ($CDCl_3$) δ 0.23 (s, 6 H), 1.01 (s, 9 H), 1.45 (s, 9 H), 2.16 (s, 3 H), 6.87 (s, 1 H), 7.49 (s, 1 H).

Example III 2-tert-Butyl-4-(tert-butyl-dimethyl-silanyloxy)-5-methyl-benzenethiol A solution of 3.02 g (9.00 mmol) oftert-butyl-(5-tert-butyl-2-methyl-4-thiocyanato-phenoxy)-dimethyl-silane (prepared in Example HHH), 2.3 g (12 mmol) of dithiothreitol, EtOH (20 mL), and 0.02 M potassium dibasic phosphate buffer (10 mL) was heated to 50° C. overnight. The mixture was cooled to room temperature, diluted with hexanes and washed with $H_2O$. The organic layer was then dried ($Na_2SO_4$) and the solvent removed in vacuo to yield the title compound. $^1$H NMR ($CDCl_3$) δ 0.20 (s, 6 H), 1.00 (s, 9 H), 1.44 (s, 9 H), 2.10 (s, 3 H), 3.42 (s, 1 H), 6.80 (s, 1 H), 7.04 (s, 1 H).

Example JJJ

Toluene-4-thiosulfonic acid S-[2-tert-butyl-4-(tert-butyl-dimethyl-silanyloxy)-5-methyl-phenyl] ester A mixture of tosyl bromide (1.82 g, 7.76 mmol), $Et_3N$ (1.08 mL, 7.76 mmol), and $CCl_4$ (15 mL) was cooled to 0° C. and treated with a solution of 2-tert-butyl-4-(tert-butyl-dimethyl-silanyloxy)-5-methyl-benzenethiol (prepared in Example III; 1.94 mmol) in $CCl_4$ (15 mL) via addition funnel over a period of 45 minutes. The mixture was then allowed to warm to room temperature where it was stirred for 4 days. The mixture was diluted with $CH_2Cl_2$ and quenched with saturated $NH_4Cl$. The layers were separated, the organic layer dried ($Na_2SO_4$) and the solvent removed in vacuo. The residue was submitted to column chromatography (3:1 hexanes:$CH_2Cl_2$ to 1:1 hexanes:$CH_2Cl_2$) to provide the title compound. $^1$H NMR ($CDCl_3$) δ 0.0 (s, 6 H), 0.78 (s, 9 H), 0.97 (s, 9 H), 1.84 (s, 3 H), 2.18 (s, 3 H), 6.60 (s, 1 H), 6.94–7.02 (m, 4 H), 7.25 (s, 1 H).

Example KKK (5-tert-Butyl-2-methyl-4-thiocyanato-phenoxy) acetic acid methyl ester To a round bottom flask (500 mL) equipped with a magnetic stirrer and condenser were added 2.0 g (9.0 mmol) of 5-tert-butyl-2-methyl-4-thiocyanato-phenol (prepared in Example GGG), cesium carbonate (5.88 g, 18.0 mmol), sodium iodide (4.8 g, 32.0 mmol), and acetonitrile (100 mL). This suspension was heated to reflux for 30 minutes and bromomethyl acetate (1.76 mL, 18.0 mmol) was added via syringe. The reaction was refluxed overnight, cooled to room temperature, quenched with $H_2O$ and extracted with EtOAc. The organic layers were combined and dried (MgSO4). The solvent was evaporated and the residue dried under high vacuum to give the title compound. $^1$H NMR ($CDCl_3$) δ 1.46 (s, 9 H), 2.26 (s, 3 H), 3.82 (s, 3 H), 4.68 (s, 2 H), 6.69 (s, 1 H), 7.52 (s, 1 H).

Example LLL 2-(5-tert-Butyl-4-mercapto-2-methyl-phenoxy)-ethanol

To a round bottom flask equipped with a magnetic stirrer and addition funnel were added 1.50 g (39.5 mmol) of lithium aluminum hydride and freshly distilled THF (40 mL). This slurry was cooled to 0° C. and treated dropwise with a solution of (5-tert-butyl-2-methyl-4-thiocyanato-phenoxy) acetic acid methyl ester (prepared in Example KKK; 4.48 g, 15.3 mmol) dissolved in freshly distilled THF (40 mL). The reaction was worked up by diluting the slurry with EtOAc and slowly adding $H_2O$ until hydrogen gas evolution had ceased. The solution was neutralized with 1N HCl and extracted with EtOAc. The organic layers were combined, dried ($MgSO_4$) and concentrated. The residue was dried under high vacuum and carried on crude to the next step (see Example MMM).

Example MMM

2-{5-tert-butyl-4-[2-tert-butyl-4-(2-hydroxy-ethoxy)-5-methyl-phenyldisulfanyl]-2-methyl-phenoxy}ethanol To a round bottom flask equipped with a magnetic stirrer were added 3.60 g (15.0 mmol) of 2-(5-tert-butyl-4-mercapto-2-methyl-phenoxy)-ethanol prepared in Example LLL, iodine (2.24 g, 8.8 mmol), EtOAc (50 mL), and $NEt_3$ (10 mL, 71.8 mmol), respectively. This mixture was stirred overnight at room temperature. The reaction was then diluted with EtOAc and washed with a 10% $NaSSO_4$ solution followed by 2N NaOH, 1N HCl, and brine. The organic layer was dried ($MgSO_4$) and the solvent evaporated. The residue was dried under high vacuum to give the title compound. $^1$H NMR ($CDCl_3$) δ 1.37 (s, 18 H), 2.04 (s, 6 H), 3.92 (t, 4 H), 4.03 (t, 4 H), 6.74 (s, 2 H), 7.26 (s, 2 H).

Example NNN

[Dithiobis[[2-(1,1-dimethylethyl)-5-methyl-4,1-phenylene]oxy-2,1-ethanediyloxy]]bis[(dimethylethyl)dimethyl]-silane To a round bottom flask equipped with magnetic stirrer were added 2-{5-tert-butyl-4-[2-tert-butyl-4-(2-hydroxy-ethoxy)-5-methyl-phenyldisulfanyl]-2-methyl-phenoxy}ethanol (prepared in Example MMM; 3.6 g, 7.53 mmol), t-butyldimethylsilyl chloride (2.57 g, 17.0 mmol), imidazole (1.156 g, 17.0 mmol) and DMF (80 mL), respectively. This solution was stirred for 3 hours at room temperature, quenched with $H_2O$ (500 mL), and extracted with EtOAc (500 mL). The organic layer was then washed with again with $H_2O$ (500 mL) and brine (500 mL). The organic layer was dried ($MgSO_4$) and the solvent evaporated. The residue was dried under high vacuum to give the title compound. $^1$H NMR ($CDCl_3$) δ 0.03 (s, 12 H), 0.84 (s, 18 H), 1.36 (s, 18 H), 2.02 (s, 6 H), 3.90 (t, 4H), 3.98 (t, 4 H), 6.76 (s, 2 H), 7.22 (s, 2 H).

Example OOO 2-tert-Butyl-4-[2-(tert-butyl-dimethyl-silanyloxy)-ethoxy]-5-methyl-benzenethiol To a round bottom flask equipped with magnetic stirrer and condenser were added [dithiobis[[2-(1,1-dimethylethyl)-5-methyl-4,1-phenylene]oxy-2,1-ethanediyloxy]]bis[(dimethylethyl)dimethyl]-silane (prepared in Example NNN; 4.76 g, 6.74 mmol), dithiothreitol (6.0 g, 38.9 mmol), 0.02 M $KH_2PO_4$ buffer (20 mL) and EtOH (150 mL), respectively. The contents of the flask were brought to reflux and stirred overnight. The EtOH was evaporated, and the residue was quenched with $H_2O$ (500 mL) and extracted with EtOAc. The organics were combined and the solvent evaporated. The residue was taken up in hexanes (500 mL) and washed with $H_2O$ (500 mL) and brine (500 mL). The organic layer was dried ($MgSO_4$) and the solvent evaporated; the residue was dried under high vacuum to give the title compound. $^1H$ NMR ($CDCl_3$) δ 0.03 (s, 6 H), 0.84 (s, 9 H), 1.39 (s, 9 H), 2.06 (s, 3 H), 3.35 (s, 1 H), 3.89 (t, 2 H), 3.93 (t, 2 H), 6.80 (s, 1 H), 6.97 (s, 1 H).

Example PPP

Toluene-4-thiosulfonic acid S-{2-tert-butyl-4-[2-(tert-butyl-dimethyl-silanyloxy)-ethoxy]-5-methyl-phenyl} ester To a round bottom flask equipped with a magnetic stirrer and an addition funnel were added tosyl bromide (6.07 g, 26.0 mmol), $CCl_4$ (70 mL) and $NEt_3$ (3.59 mL, 26.0 mmol), and this solution was cooled to 0° C. The 2-tert-butyl-4-[2-(tert-butyl-dimethyl-silanyloxy)-ethoxy]-5-methyl-benzenethiol material prepared in Example OOO (4.6 g, 13.0 mmol) was dissolved in $CCl_4$ (70 mL) and added dropwise to the tosyl bromide solution. The addition was complete in 3.5 hours, at which time the ice bath was removed and the reaction stirred at room temperature overnight. The mixture was diluted with $CH_2Cl_2$ and washed with saturated $NH_4Cl$ and dried ($MgSO_4$). The solvent was then evaporated and the residue was submitted to flash chromatography (1:1 $CH_2Cl_2$:hexane) to yield the title compound. $^1H$ NMR ($CDCl_3$) δ 0.04 (s, 6 H), 0.85 (s, 9 H), 1.20 (s, 9 H), 2.01 (s, 3 H), 2.37 (s, 3 H), 3.93 (t, 2 H), 3.99 (t, 2 H), 6.82 (s, 1 H), 7.03 (s, 1 H), 7.19 (d, 2 H), 7.44 (d, 2 H).

Example QQQ 5-tert-Butyl-4-mercapto-2-methyl-phenol

To a round bottom flask equipped with a magnetic stirrer and condenser were added 35 g (158 mmol) of 5-tert-butyl-2-methyl-4-thiocyanato-phenol prepared in Example GGG, dithiothreitol (25.61 g, 166 mmol), EtOH (250 mL), and 0.02 M $KH_2PO_4$ buffer solution (25 mL), respectively. The reaction was heated to reflux; after 2 hours, additional dithiothreitol (5.0 g, 32.4 mmol) and 0.02 M $KH_2PO_4$ buffer solution (25 mL) were added. After 2 hours at reflux, the solution was cooled to room temperature and concentrated. The reaction was quenched with brine and extracted with 1:1 $Et_2O$:hexanes. The organic layer was washed with brine, dried ($MgSO_4$), and concentrated. The residue was submitted to column chromatography (100% $CHCl_3$, silica gel) to yield the title compound. $^1H$ NMR ($CDCl_3$) δ 1.45 (s, 9 H), 2.15 (s, 3 H), 3.43 (s, 1 H), 4.56 (br s, 1 H), 6.82 (s, 1 H), 7.05 (s, 1 H).

Example RRR

Toluene-4-thiosulfonic acid S-(2-tert-butyl-4-hydroxy-5-methyl-phenyl) ester

To a round bottom flask equipped with a magnetic stirrer and addition funnel were added tosyl bromide (30.6 g, 130 mmol), $CCl_4$ (150 mL), and pyridine (10.51 mL, 130 mmol), respectively. This slurry was cooled to 0° C. and treated dropwise a solution of 24.3 g (124 mmol) of 5-tert-butyl-4-mercapto-2-methyl-phenol (prepared in Example QQQ) in $CCl_4$ (150 mL). The mixture was diluted with $CHCl_3$, washed with brine, and dried ($MgSO_4$). The solvent was evaporated to give a solid which was washed and filtered with hexanes:$Et_2O$ (4:1) to give the title compound. $^1H$ NMR ($CDCl_3$) δ 1.22 (s, 9 H), 2.11 (s, 3 H), 2.42 (s, 3 H), 6.87 (s, 1 H), 7.16 (s, 1 H) 7.26 (d, 2 H), 7.49 (d, 2 H).

Example SSS

Dimethyl-sulfamic acid 5-tert-butyl-2-methyl-4-thiocyanato-phenyl ester

To a round bottom flask equipped with a condenser and magnetic stirrer were added 5-tert-butyl-2-methyl-4-thiocyanato-phenol prepared in Example GGG (1.5 g, 6.8 mmol), cesium carbonate (2.44 g, 7.49 mmol), and acetonitrile (30 mL). This slurry was brought to reflux for 15 minutes. Dimethyl sulfamoyl chloride (0.80 mL, 7.49 mmol) was added to the slurry via syringe. The reaction was quenched with brine and extracted with EtOAc; the organic layer was dried ($MgSO_4$) and concentrated. The residue was submitted to column chromatography (7:3 hexane:EtOAc) to give the title compound. $^1H$ NMR ($CDCl_3$) δ 1.46 (s, 9 H), 2.22 (s, 3 H), 3.03 (s, 6 H), 7.30 (s, 1 H), 7.47 (s, 1 H).

Example TTT

Dimethyl-sulfamic acid 5-tert-butyl-4-mercapto-2-methyl-phenyl ester

To a round bottom flask equipped with a magnetic stirrer and condenser were added 1.1 g (3.3 mmol) of dimethyl-sulfamic acid 5-tert-butyl-2-methyl-4-thiocyanato-phenyl ester (prepared in Example SSS), dithiothreitol (1.29 g, 8.35 mmol), EtOH (40 mL), and 0.02 M $KH_2PO_4$ buffer solution (5 mL), respectively. The reaction was refluxed overnight. The mixture was then quenched with $H_2O$ (250 mL) and extracted with a 1:1 mixture of hexanes:$Et_2O$. The organic layer was again washed with $H_2O$ and brine, dried ($MgSO_4$) and concentrated. The residue was dried under high vacuum to yield the title compound. $^1H$ NMR ($CDCl_3$) δ 1.45 (s, 9 H), 2.25 (s, 3 H), 3.02 (s, 6 H), 3.57 (s, 1 H), 7.01 (s, 1 H), 7.28 (s, 1 H).

Example UUU

Toluene-4-thiosulfonic acid S-(2-tert-butyl-4-dimethylsulfamoyloxy-5-methyl-phenyl) ester To a round bottom flask equipped with a magnetic stirrer and addition funnel were added tosyl bromide (1.64 g, 7.0 mmol), $CCl_4$ (25 mL), and $NEt_3$ (0.98 mL, 7.0 mmol). The ensuing slurry was then cooled to 0° C. A solution of 1.07 g (3.5 mmol) of dimethyl-sulfamic acid 5-tert-butyl-4-mercapto-2-methyl-phenyl ester (prepared in Example TTT) in $CCl_4$ (25 mL) was added dropwise to the slurry. Addition was complete in 1.0 hour. After addition was complete, the ice bath was removed and the reaction was stirred at room temperature overnight. The mixture was diluted with $CH_2Cl_2$, washed with brine, dried ($MgSO_4$), and concentrated. The residue was taken up in a small amount of EtOAc and triturated with hexane. The product was filtered and dried under high vacuum to yield the title compound. $^1H$ NMR ($CDCl_3$) δ 1.15 (s, 9 H), 2.23 (s, 3 H), 2.37 (s, 3 H), 3.02 (s, 6 H), 7.19 (d, 2 H), 7.22 (s, 1 H), 7.33 (s, 1 H), 7.40 (d, 2 H).

Example VVV

Toluene-4-thiosulfonic acid S-(2-tert-butyl-4-ethylsulfamoyloxy-5-methyl-phenyl) ester To a round bottom flask equipped with a magnetic stirrer and nitrogen were added toluene-4-thiosulfonic acid S-(2-tert-butyl-4-hydroxy-5-methyl-phenyl) ester (prepared in Example RRR; 6.86 g, 19.6 mmol), $Et_2O$ (100 mL), and $NEt_3$ (3.25 mL, 23.4 mmol), respectively. The solution was cooled to 0° C. and treated rapidly with a solution of (ethyl amino)sulfonyl chloride (3.37 g, 23.4 mmol) in $Et_2O$ (10 mL). The reaction was stirred for 30 minutes and then filtered. The solids were washed with $Et_2O$, and the filtrate was concentrated. The resulting residue was dried in a high vacuum oven at 40° C. overnight to yield the title compound. $^1$H NMR (CDCl$_3$) δ 1.15 (s, 9 H), 1.23 (t, 3 H) 2.19 (s, 3 H), 2.35 (s, 3 H), 3.30 (m, 2 H), 4.75 (br t, 1 H), 7.16 (s, 1 H), 7.19 (s, 1 H), 7.32 (d, 2 H), 7.39 (d, 2 H).

Example WWW

4-Methyl-piperazine-1-sulfonic acid, 5-tert-butyl-2-methyl-4-(toluene-4-sulfonylsufanyl)-phenyl ester To a round bottom flask equipped with a magnetic stirrer was added 2.0 g (5.6 mmol) of toluene-4-thiosulfonic acid S-(2-tert-butyl-4-hydroxy-5-methyl-phenyl) ester (prepared in Example RRR), 4-methyl-piperazine-1-sulfonyl chloride monohydrochloride (5.26 g, 22.4 mmol), THF (50 mL), pyridine (50 mL), a catalytic amount of DMAP, and NEt$_3$ (6.24 mL, 44.8 mmol). The reaction was stirred overnight at room temperature, quenched with 1N HCl and brine, and extracted with EtOAc. The organics were washed with brine and dried (MgSO$_4$). The solvent was evaporated and the residue submitted to column chromatography (7:3 hexane:EtOAc) to yield the title compound. $^1$H NMR (CDCl$_3$) δ 1.19 (s, 9 H), 2.34 (s, 3 H), 2.36 (s, 3 H), 2.41 (s, 3 H), 2.57 (br m, 6 H), 3.36 (br m, 2 H), 7.24 (d, 2 H), 7.39 (s, 1 H), 7.43 (d, 2 H), 7.46 (s, 1 H).

Example XXX

1-Methyl-1H-imidazole-4-sulfonic acid, 5-tert-butyl-2-methyl-4-(toluene-4-sulfonylsufanyl)-phenyl ester To a round bottom flask equipped with a magnetic stirrer were added 0.78 g (2.21 mmol) of toluene-4-thiosulfonic acid S-(2-tert-butyl-4-hydroxy-5-methyl-phenyl) ester (prepared in Example RRR), 1-methyl-1H-imidazole-4-sulfonyl chloride (0.50 g, 2.70 mmol), CH$_2$Cl$_2$ (20 mL), and NEt$_3$ (0.38 mL, 2.70 mmol). The reaction was stirred overnight at room temperature. The solution was concentrated, and the residue was dissolved in EtOAc, washed with 1N HCl and brine, and dried (MgSO$_4$). The solvent was evaporated; the resulting solid was taken up in a small amount of EtOAc, filtered, and dried under high vacuum to yield the title compound. $^1$H NMR (DMSO-d$_6$) δ 1.05 (s, 9 H), 2.06 (s, 3 H), 2.38 (s, 3 H), 3.69 (s, 3 H), 6.90 (s, 1 H), 7.18 (s, 1 H), 7.41 (s, 4 H), 8.02 (s, 1 H), 8.08 (s, 1 H).

Example YYY

Toluene-4-thiosulfonic acid S-(2-tert-butyl-4-tert-butylsulfamoyloxy-5-methyl-phenyl) ester To a round bottom flask equipped with a magnetic stirrer were added 1.10 g (3.20 mmol) of toluene-4-thiosulfonic acid S-(2-tert-butyl-4-hydroxy-5-methyl-phenyl) ester (prepared in Example RRR), Et$_2$O (50 mL), and 0.90 mL (6.40 mmol) of NEt$_3$, in that order. The solution was cooled to 0° C. To this solution was rapidly added a solution of 1.10 g (6.40 mmol) of (tert-butyl amino)sulfonyl chloride (Matler, W. L., Comer, W. T., and Deitchman, D., Journal of Medicinal Chemistry, 1972,15 (5), 538–541) in Et$_2$O (10 mL). A precipitate ensued and the reaction was allowed to stir for 30 minutes. Another two equivalents of (tert-butyl amino)sulfonyl chloride (1.10 g, 6.40 mmol) in Et$_2$O (10 mL) and NEt$_3$ (0.90 mL, 6.40 mmol) were added, and the reaction mixture was stirred for another 30 minutes. The reaction was quenched with brine and the organics extracted with Et$_2$O. The organics were dried (MgSO$_4$) and concentrated. The residue was submitted to flash chromatography (EtOAc:CHCl$_3$ 1:9) to yield the title compound. $^1$H NMR (CDCl$_3$) δ 1.23 (s, 9 H), 1.46 (s, 9 H), 2.25 (s, 3 H), 2.42 (s, 3 H), 4.63 (br s, 1 H), 7.23 (s, 1 H), 7.26 (s, obscured by CDCl$_3$, 1 H), 7.42 (d, 2 H), 7.46 (d, 2 H).

Example ZZZ

Bis[2-(1,1-dimethylethyl)-4-[2-(methoxymethoxy)ethoxy]-5-methylphenyl]disulfide

The title compound was prepared using 7.0 g (29 mmol) of 2-{5-tert-butyl-4-[2-tert-butyl-4-(2-hydroxy-ethoxy)-5-methyl-phenyldisulfanyl]-2-methyl-phenoxy}ethanol (prepared in Example MMM), 200 mL of CH$_2$Cl$_2$, 15.2 g (118 mmol) of diisopropylethylamine and 9.45 g (118 mmol) of chloromethyl methyl ether. The reagents were mixed at 0° C. and stirred at that temperature for 1 hour. The reaction mixture was warmed to room temperature and stirred for 15 hours, then diluted with EtOAc and quenched with 1N HCl. The organic layer was washed with sodium bicarbonate solution and brine and dried (MgSO$_4$). The solvents were removed, and the residue was subjected to flash silica gel chromatography, eluting with EtOAc:hexane (5:95, then switching to 1:4).

Example AAAA 2-tert-Butyl-4-(2-methoxymethoxy-ethoxy)-5-methyl-benzenethiol

Bis [2-(1,1-dimethylethyl)-4-[2-(methoxymethoxy)ethoxy]-5-methylphenyl]disulfide prepared in Example ZZZ (7.0 g, 12 mmol) was taken in 100 mL of EtOH. To it 21 g (136 mmol) of dithiothreitol and 10 mL of dibasic phosphate buffer (pH:4.5) was added. The reaction was kept at 80–90° C. overnight, then cooled to 0° C. and poured into H$_2$O; the product was extracted with hexanes:EtOAc (8:2) solvent system. The organic layer was washed with H$_2$O and dried (Na$_2$SO$_4$). The product was used as such without any purification.

Example BBBB

Toluene 4-thiosulfonic acid S-[2-tert-butyl-4-(2-methoxymethoxy-ethoxy)-5-methyl-phenyl] ester A solution of tosyl bromide (21.0 g; 89.32 mmol), 50 mL of trichloroethane and 20 mL of NEt$_3$ was cooled to 0° C. To this solution was added slowly a solution of 12.4 mmol of 2-tert-butyl-4-(2-methoxymethoxy-ethoxy)-5-methyl-benzenethiol (prepared in Example AAAA) in 100 mL of trichloroethane. After 13 hours, the reaction mixture was diluted with EtOAc and washed with brine. The product was purified by flash silica gel chromatography, eluting with EtOAc:hexane (5:95, then switching to 3:7).

Example CCCC 5-tert-Butyl-2-methyl-phenylamine

A solution of (239 g, 1.2 mol) 4-tert-butyl-1-methyl-2-nitro-benzene (M. S. Carpenter, W. M. Easter, T. F. Wood, J. Org. Chem. (1951), 586) in MeOH (1.0 L) was treated with Raney nickel (25 g) in a Parr shaker. The apparatus was sealed under hydrogen pressure to 52 psi, heated to 35° C. for 15 hours, and cooled to room temperature. The apparatus was vented and the contents filtered. The filtrate was concentrated in vacuo and distilled, collecting the major fraction (75–85° C., 1.0 torr). $^1$H NMR (CDCl$_3$) δ 1.26 (s, 9 H), 2.11 (s, 3 H), 3.54 (bs, 2 H), 6.69 (d, 1 H), 6.72 (dd, 1 H), 6.96 (d, 1 H).

Example DDDD 5-tert-Butyl-2-methyl-4-thiocyanato-phenylamine

A solution of 1.0 g (6.1 mmol) of 5-tert-butyl-2-methyl-phenylamine prepared in Example CCCC, sodium thiocyanide (1.62 g, 20.0 mmol) and MeOH (4.0 mL) was cooled to 0° C. and treated via addition funnel with a solution of bromine (0.35 mL, 6.7 mmol), sodium bromide (0.63 g, 6.13 mmol), and MeOH (5.0 mL). The mixture was stirred for 30 minutes and then carefully diluted with saturated sodium bicarbonate. The mixture was extracted with $CH_2Cl_2$ and the organic layers combined, dried ($Na_2SO_4$), and the solvent evaporated. The residue was then submitted to column chromatography (4:1 $CH_2Cl_2$:hexanes to 19:1 $CH_2Cl_2$:hexanes +1% MeOH) to provide the title compound. $^1$H NMR ($CDCl_3$) δ 1.42 (s, 9 H), 2.09 (s, 3 H), 3.80 (bs, 2 H), 6.69 (s, 1 H), 7.35 (s, 1 H).

Example EEEE

[4-(Cyanothio)-5-(1,1-dimethylethyl)-2-methylphenyl]-imidodicarbonic acid bis(1,1-dimethylethyl) ester A solution of 5-tert-butyl-2-methyl-4-thiocyanato-phenylamine (8.0 g, 36.36 mmol) (prepared in Example DDDD) and di-tert-butyl dicarbonate (31.7 g, 145.3 mmol) in THF (80 mL) was stirred at 60° C. under $N_2$ overnight. Solvent was then removed in vacuo and $Et_2O$ added; the solution was washed with saturated $NaHCO_3$ solution and brine, dried ($Na_2SO_4$), filtered and concentrated. The material was purified by flash chromatography on silica gel, eluting with 4:1 hexanes:EtOAc to 1:1 hexanes:EtOAc to afford the title compound. $^1$H NMR ($CDCl_3$) δ 1.41 (s, 9 H), 1.43 (s, 3 H), 1.52 (s, 18 H), 7.14 (s, 1 H), 7.58 (s, 1 H).

Example FFFF

[5-(1,1-Dimethylethyl)-4-mercapto-2-methylphenyl]-imidodicarbonic acid bis(1,1-dimethylethyl) ester To a solution of [4-(cyanothio)-5-(1,1-dimethylethyl)-2-methylphenyl]-imidodicarbonic acid bis(1,1-dimethylethyl) ester obtained in Example EEEE (11.65 g, 27.7 mmol) in denatured EtOH (160 mL) was added dithiothreitol (16.8 g, 109.1 mmol), and 0.2 M $KH_2PO_4$ solution (40 mL). The mixture was stirred overnight at 50° C. The solvent was evaporated, and $H_2O$ and $CHCl_3$ were added; the organic layer was washed with brine, dried ($Na_2SO_4$) filtered and concentrated. The resulting residue was flash chromatographed on silica gel, eluting with 1:1 $CHCl_3$:hexanes switching to 19:1 $CHCl_3$:EtOAc, to afford the title compound. $^1$H NMR ($CDCl_3$) δ 1.40–1.46 (m, 27 H), 2.07 (s, 3 H), 7.00 (s, 1 H), 7.05 (s, 1 H).

Example GGGG

[5-(1,1-Dimethylethyl)-2-methyl-4[[(4-methylphenyl)sulfonyl]thio]phenyl]-imidodicarbonic acid bis(1,1-dimethylethyl) ester A solution of tosyl bromide (17.1 g, 72.73 mmol) and $NEt_3$ (7.36 g, 72.73 mmol) in $CCl_4$ (250 mL) was cooled to 0° C. To this solution was added [5-(1,1-dimethylethyl)-4-mercapto-2-methylphenyl]-imidodicarbonic acid bis(1,1-dimethylethyl) ester obtained from Example FFFF in $CCl_4$ (250 mL) dropwise over an 8 hour period. The mixture was then allowed to warm to room temperature overnight. Chloroform was added, and the solution was washed with $H_2O$ and brine, dried ($Na_2SO_4$), filtered and concentrated. The resulting material was flash chromatographed on silica gel, eluting with 4:1 $CHCl_3$:hexanes to afford the title compound. $^1$H NMR ($CDCl_3$) δ 1.16 (s, 9 H), 1.40 (s, 18 H), 2.10 (s, 3 H), 2.40 (s, 3 H), 7.07 (s, 1 H), 7.19 (d, 2 H), 7.40 (s, 1 H), 7.44 (d, 2 H).

Example HHHH

Toluene-4-thiosulfonic acid S-(4-amino-2-tert-butyl-5-methyl-phenyl) ester

The product from example GGGG (10.95 g, 19.92 mmol) was dissolved in $CH_2Cl_2$ (200 mL) and HCl gas bubbled in while stirring at room temperature for 40 minutes. The solvent was evaporated, and the isolated residue was triturated with $Et_2O$ to afford the hydrochloride salt. The resulting solid was dissolved in MeOH, and pH 7.5 $K_2HPO_4$/$KH_2PO_4$ buffer was added until a precipitate formed. The resulting precipitate was filtered off and washed with $H_2O$ and then hexanes to afford the title compound. $^1$H NMR (DMSO-$d_6$) δ 1.16 (s, 9 H), 1.96 (s, 3 H), 2.38 (s, 3 H), 5.88 (br s, 3 H), 6.83 (s, 1 H), 6.95 (s, 1 H), 7.39 (d, 2 H), 7.45 (d, 2 H).

Example IIII

4-Methyl-benzenesulfonothioic acid[4-[[(dimethylamino)sulfonyl]amino]-2-(1,1-dimethylethyl)-5-methylphenyl] ester A solution of 0.40 g (1.14 mmol) of toluene-4-thiosulfonic acid S-(4-amino-2-tert-butyl-5-methyl-phenyl) ester from example HHHH and N,N-dimethylsulfamoyl chloride (0.31 g, 2.18 mmol) in pyridine (10 mL) was stirred at room temperature under nitrogen overnight. Dichloromethane was then added, and the organic mixture was washed with saturated $CuSO_4$:$H_2O$ solution, then with 1N HCl and brine, dried ($Na_2SO_4$), filtered and concentrated. The resulting residue was flash chromatographed on silica gel, eluting with $CHCl_3$ to afford the title compound. $^1$H NMR ($CDCl_3$) δ 1.21 (s, 9 H), 2.18 (s, 3 H), 2.42 (s, 3 H), 2.88 (s, 6 H), 6.20 (s, 1 H), 7.23 (d, 2 H), 7.34 (s, 1 H), 7.49 (d, 2 H), 7.56 (s, 1 H).

Example JJJJ

Toluene-4-thiosulfonic acid S-[2-tert-butyl-4-(4-cyano-benzenesulfonylamino)-5-methyl-phenyl] ester A solution of toluene-4-thiosulfonic acid S-(4-amino-2-tert-butyl-5-methyl-phenyl) ester obtained from Example HHHH (0.20 g, 0.57 mmol), 4-cyanobenzenesulfonyl chloride (0.15 g, 0.74. mmol), pyridine (7 mL) and $CH_2Cl_2$ (1 mL) was stirred at room temperature under nitrogen overnight. 1N HCl was then added and the mixture was extracted with EtOAc. The organic phase was washed with 1N HCl and brine, dried ($Na_2SO_4$), filtered and concentrated. The resulting residue was flash chromatographed on silica gel, eluting with 19:1 $CHCl_3$:EtOAc to afford the title compound. $^1$H NMR ($CDCl_3$) δ 1.16 (s, 9 H), 1.98 (s, 3 H), 2.43 (s, 3 H), 6.49 (s, 1 H), 7.23 (s, 1 H), 7.27 (d, partially obscured by $CDCl_3$, 2 H), 7.48 (d, 2 H), 7.78 (d, 2 H), 7.87 (d, 2 H).

Example KKKK 2-tert-Butyl-5-methyl-benzene thiol

A solution of 32.8 g (200 mmol) of 2-t-butyl-5-methylphenol in 150 mL of DMF was treated portionwise with 9.6 g (240 mmol) of 60% NaH. The mixture was stirred at room temperature for 1 hour and then treated with 32.3 g (260 mmol) of N,N-dimethylthiocarbamoyl chloride all at once. The reaction mixture was stirred at 50° C. for 16 hours. Water and EtOAc were added; the organic layer was separated and washed with 1N NaOH, 1N HCl, and brine. The solution was dried and concentrated. The residue was chromatographed on silica gel, eluting with 6:1 hexane:EtOAc. $^1$H NMR ($CDCl_3$) δ 1.31 (s, 9 H), 2.27 (s, 3 H), 3.35 (s, 3 H), 3.45 (s, 3 H), 6.80 (bs, 1 H), 6.95 (d, 1 H), 7.23 (d, 1 H).

The intermediate prepared above was heated neat to 310° C. for 2 hours and then cooled to room temperature. The product was chromatographed on silica gel, eluting with a gradient of 6:1 hexane:EtOAc to 2:1 hexane:EtOAc. $^1$H NMR (CDCl$_3$) δ 1.42 (s, 9 H), 2.27 (s, 3 H), 3.05 (br d, 6 H), 7.09 (d, 1 H), 7.25 (br s, 1 H), 7.32 (d, 1 H).

To a suspension of 8.5 g (220 mmol) of lithium aluminum hydride in 200 mL of Et$_2$O at 5° C. was added a solution of 31.1 g (124 mmol) of the product isolated in the previous paragraph in Et$_2$O (100 mL). Addition was complete in 45 minutes. The ice bath was removed, and the mixture was stirred at room temperature for 15 hours. The suspension was treated cautiously with EtOAc (100 mL), H$_2$O (100 mL), and 1N HCl:5% citric acid. The mixture was filtered, and the filtrate was transferred to a separator funnel. The organic phase was separated, washed with brine, and dried. Concentration gave the title compound which was used without purification in the next step.

Example LLLL 2-tert-Butyl-5-methylphenyl-p-toluenethiosulfonate

To a solution of 15.8 g (67 mmol) of tosyl bromide, 9.4 mL (67 mmol) of NEt$_3$, and 250 mL of CCl$_4$ was added a solution of 11.0 g (61 mmol) of 2-tert-butyl-5-methyl-benzene thiol (prepared in Example KKKK) in 100 mL of CCl$_4$ at such a rate that the addition was complete in 3 hours. When addition was complete, the solution was washed with 3N HCl, saturated aq. NaHCO$_3$, and brine and was dried (MgSO$_4$). Concentration gave a residue which was chromatographed over silica gel, eluting with 5:1 hexane:EtOAc, to yield the title compound. $^1$H NMR (CDCl$_3$) δ 1.19 (s, 9 H), 2.21 (s, 3 H), 2.38 (s, 3 H), 7.08–7.20 (m, 3 H), 7.26 (m, 2 H), 7.44 (d, 2 H).

Example MMMM (5-tert-Butyl-4-mercapto-2-methyl-phenoxy)acetic acid methyl ester 1.00 g (3.4 mmol) of (5-tert-butyl-2-methyl-4-thiocyanato-phenoxy)acetic acid methyl ester prepared in Example KKK was combined with 3.16 g (20 mmol) dithiothreitol (DTT) in a solution of 10 mL 0.02 M K$_2$PO$_4$ buffer and 40 mL of EtOH. The reaction was refluxed overnight, then cooled and partially concentrated. After dilution with water, the mixture was extracted with EtOAc, and the organic layer washed with saturated aqueous brine, dried (Na$_2$SO$_4$) and concentrated. The residue was chromatographed on silica gel eluting with 3:1 hexanes:EtOAc, to give the title compound. $^1$H NMR (CDCl$_3$) δ 1.44 (s, 9 H), 2.19 (s, 3 H), 3.46 (s, 1 H), 3.80 (s, 3 H), 4.62 (s, 2 H), 6.76 (s, 1 H), 7.06 (s, 1 H).

Example NNNN

[5-tert-Butyl-2-methyl-4-(toluene-4-sulfonylsulfanyl)-phenoxy]-acetic acid 1.86 g (7.9 mmol, 2 equivalents) tosyl bromide and 1.05 mL (7.9 mmol) NEt$_3$ were combined in 200 mL CCl$_4$ and the mixture chilled in an ice bath under nitrogen. To this mixture was added a solution of 1.06 g (3.95 mmol) of (5-tert-butyl-4-mercapto-2-methyl-phenoxy)acetic acid methyl ester (prepared in Example MMMM) in 125 mL of CCl$_4$ over 3 hours, and the reaction was allowed to come to ambient temperature overnight. The mixture was then diluted with CH$_2$Cl$_2$, washed with aqueous ammonium chloride and aqueous sodium chloride, and dried (Na$_2$SO$_4$). Concentration gave a residue which was chromatographed on silica gel eluting with 3:1 hexanes:EtOAc to yield the title compound. $^1$H NMR (CDCl$_3$) δ 1.25 (s, 9 H), 2.14 (s, 3 H), 2.43 (s, 3 H), 3.82 (s, 3 H), 4.68 (s, 2 H), 6.75 (s, 1 H), 7.14 (s, 1 H), 7.25 (d, 2 H), 7.50 (d, 2 H).

Example OOOO

4-Hydroxy-6,6-diphenethyl-5,6-dihydro-pyran-2-one

Freshly distilled THF (25 mL) was cooled in an ice bath under a nitrogen atmosphere, then charged with 660 mg (16.5 mmol) sodium hydride (60% dispersion). This suspension was treated with 1.89 g (16.3 mmol) methyl acetoacetate dropwise, and the reaction was stirred for 10 minutes. n-Butyllithium (10.3 mL of 1.6 M in hexanes; 16.5 mmol) was dripped in and the reaction was stirred 30 minutes. At this time 3.10 g (13 mmol) of 1,5-diphenyl-3-pentanone (Ram and Spicer, *Tetrahedrom Lett.*, 1988, 29 (31), 3741) in 20 mL THF was added dropwise over 15 minutes. After 4 hours 100 mL H$_2$O was added and the reaction stirred overnight. The reaction was extracted with diethyl ether, and the organics set aside. The aqueous layer was chilled, treated with 50% HOAc until a precipitate formed, and then extracted with EtOAc. These organics were washed with saturated brine, dried (Na$_2$SO$_4$), and concentrated. $^1$H NMR (DMSO-d$_6$) δ 2.0 (d of d, 4 H), 2.65 (m, 6 H), 5.0 (s, 1 H), 7.15–7.35 (m, 10 H), 11.4 (bs, 1 H).

Example PPPP

4-Hydroxy-6-(3-methyl-butyl)-6-phenethyl-5,6-dihydro-pyran-2-one

The title compound was prepared as described in General Method 5 using 2.56 g (22 mmol) of methyl acetoacetate, 0.97 g (24.2 mmol) of NaH 60% dispersion in oil, 14.4 mL (23.1 mmol) of 1.6 M n-butyl lithium in hexane, 4.5 g (22.0 mmol) of 6-methyl-1-phenyl-heptan-3-one (A. Katritzky, et al., *J. Org. Chem.*, 1995, 60 (23), 7605) and 60 mL of THF. After addition of the ketone, the reaction was stirred for 90 minutes at 0° C. and then for 30 minutes at room temperature. Water (400 mL) was slowly added with vigorous stirring, and the reaction was allowed to stir overnight. The reaction was worked up as in General Method 6. The product was triturated from ether to afford a solid, m.p. 99–100.5° C. $^1$H NMR (CDCl$_3$) δ 0.89–0.92 (d,d, 6 H), 1.24–1.32 (m, 2 H), 1.48–1.57 (m, 1 H), 1.64–1.83 (m, 2 H), 1.94–2.03 (m, 2 H), 2.68–2.77 (m, s, 4 H), 3.42 (s, 2 H), 7.16–7.32 (m, 5 H).

GENERAL METHOD 9

The appropriate dihydropyrone intermediate (1 eq) was added to a reaction flask followed by DMF (1–12 mL per mmol of dihydropyrone). Potassium carbonate (K$_2$CO$_3$) (4–8 eq) was added followed by the appropriate thiotosylate reagent (1.1–1.5 eq). The reaction was stirred at room temperature (2.5 hours to overnight). The reaction was worked up by pouring into a mixture of EtOAc and either 1N HCl or saturated aqueous NH$_4$Cl. The layers were separated and the aqueous layer extracted again with EtOAc. The combined organic extracts were washed with brine, dried (MgSO$_4$), and concentrated.

Example QQQQ

3-[2-(4-Benzyloxy-phenyl)-ethyl]-3-hydroxy-4-methyl-pentanoic acid tert-butyl ester Diisopropylamine (44.8 mL, 320 mmol) in THF (125 mL) was cooled to −15° C. n-Butyllithium (1.6 M, 200 mL, 320 mmol) was added over 20 minutes. The solution was cooled to −40° C. and stirred for 20 minutes. Tert-butyl acetate (43 mL, 320 mmol) in THF (90 mL) was added over 30 minutes and the reaction stirred for 30 minutes at −40° C. 1-(4-Benzyloxy-phenyl)-4-methyl-pentan-3-one (21.0 g, 100 mmol) from Example F in THF (125 mL) was added over 10 minutes and the reaction was stirred at −40° C. for 5 minutes. Acetic acid (40 mL, 700 mmol) was added and the reaction warmed to room temperature. The reaction was stripped to dryness and the product was partitioned between ethyl acetate and saturated NH$_4$Cl. The organic layer was washed with water, 5% NaHCO$_3$ and brine. It was dried (MgSO$_4$) and concentrated to give the title compound.

Example RRRR

3-[2-(4-Benzyloxy-phenyl)-ethyl-3-hydroxy-4-methyl-pentanoic acid

The title compound was prepared by dissolving 3-[2-(4-benzyloxy-phenyl)ethyl]-3-hydroxy-4-methyl-pentanoic acid tert-butyl ester (28 g, 70.3 mmol) from Example QQQQ in MeOH (150 mL). Lithium hydroxide (5.9 g, 140.6 mmol) in water (50 mL) was added and the reaction heated to reflux for 5 hours, cooled and pumped to dryness under vacuum. The product was partitioned between water and Et$_2$O. The aqueous layer was decanted, acidified with 1N HCL, and the precipitate was filtered and dried under vacuum to give the title compound (mp 97–98° C.).

Example SSSS

3-[2-(4-Benzyloxy-phenyl)-ethyl]-3-hydroxy-4-methyl-pentanoic acid methyl ester

A solution of 3-[2-(4-benzyloxy-phenyl)-ethyl]-3-hydroxy-4-methyl-pentanoic acid from Example RRRR (10.1 g, 29.5 mmol), MeOH (300 mL), and H$_2$SO$_4$ (0.2 mL) was refluxed for 3 days. The reaction was stripped to dryness and the product was partitioned between ethyl acetate and 5% NaHCO$_3$. The solution was dried (MgSO$_4$), and concentrated to give the title compound.

Example TTTT (S)-3-Hydroxy-3-[2-(4-hydroxy-phenyl)-ethyl]-4-methyl-pentanoic acid methyl ester The title compound was prepared as described in General Method 4 using 3-[2-(4-benzyloxy-phenyl)-ethyl]-3-hydroxy-4-methyl-pentanoic acid methyl ester (8.6 g, 24.2 mmol) from Example SSSS. Three grams of 20% Pd over charcoal and THF:MeOH 1:1 (100 mL). The crude compound was recrystallized from hexanes-ethyl acetate to give racemic title compound (m.p. 89–91° C.). The title compound was obtained by resolution on a semi-preparative Chiralcel OD column eluting with 90% hexanes, 10% iso-propanol and 0.1% trifluoroacetic acid. $^1$H-NMR (CDCl$_3$) δ 0.93 (d, 3H), 0.95 (d, 3H), 1.68–1.85 (m, 2H), 1.93 (m, 1H), 2.53 (dd, 2H), 2.62 (m, 2H), 3.63 (br s, 1H), 3.71 (s, 3H), 4.97 (br s, 1H), 6.73 (d, 2H), 7.03 (d, 2H).

Example UUUU (S)-3-Hydroxy-3-[2-(4-hydroxy-phenyl)-ethyl]-4-methyl-pentanoic acid The title compound was prepared by dissolving (S)-3-hydroxy-3-[2-(4-hydroxy-phenyl)-ethyl]-4-methyl-pentanoic acid methyl ester (0.57 g, 2.15 mmol) from Example TTTT in MeOH (30 mL). Lithium hydroxide (0.18 g, 4.29 mmol) in water (10 mL) was added and the reaction heated to reflux for 1 hour, cooled and pumped to dryness under vacuum. The product was partitioned between water and Et$_2$O. The aqueous layer was decanted, acidified with 1N HCl and extracted with Et$_2$O. The solution was dried (MgSO$_4$) and concentrated to give the title compound (m.p. 137–140° C.).

Example VVVV

Bis[3-ethoxy-3-oxopropanoato(1-)-O,O']-magnesate

Monoethyl malonate (0.7 g, 5.25 mmol) in THF (10 mL) was cooled to −78° C. and dibutyl magnesium (1.5 mL, 1.5 mmol) was added and the reaction stirred for 10 minutes at −78° C. then warmed to room temperature over 1 hour.

The solution was concentrated under vacuum to give the title compound.

Example WWWW (S)-4-Hydroxy-6-[2-(4-hydroxy-phenyl)-ethyl]-6-isopropyl-5,6-dihydro-pyran-2-one The title compound was prepared using (S)-3-hydroxy-3-[2-(4-hydroxy-phenyl)-ethyl]4-methyl-pentanoic acid (0.45 g, 1.78 mmol) from Example UUUU, THF (10 mL), and CDI (0.58 g, 3.58 mmol). The reaction was stirred 15 overnight at room temperature then added to bis[3-ethoxy-3-oxopropanoato(1-)-O,O']-magnesate (1.5 g, 5.2 mmol) from Example VVVV and the reaction stirred for 3 days at room temperature. The reaction was concentrated and the residue partitioned between ethyl acetate and 1N HCl. The organic layer was washed with aqueous NaHCO$_3$ and brine, dried (MgSO$_4$) and concentrated. 20 The crude product was cyclized as described in General Method 7 using 10 mL of THF and 150 mL of 0.1N NaOH. Purification by silica gel chromatography, eluting with CH$_2$Cl$_2$:MeOH (98:2) gave the title compound. $^1$H-NMR (DMSO-d$_6$) δ 0.83 (d, 3 H), 0.86 (d, 3 H), 1.78 (m, 2 H), 2.06 (m, 1 H), 2.25 (d of ABX q, 1 H), 2.39 (m, 2 H), 2.53 (d of ABX q, 1 H), 4.89 (s, 1 H), 6.6 (d, 2 H), 6.89 (d, 2 H), 9.1 (br s, 1 H).

Example XXXX 3-(3-Benzyloxy-phenyl)-propanoic acid 3-(3-Hydroxy-phenyl)-propionic acid (100 g, 0.601 mmol) and anhydrous K$_2$CO$_3$ were taken up in 1000 mL of acetone. To this slurry was added, dropwise, benzyl bromide (150.1 mL, 1.262 mol). After the addition was complete, the slurry was heated to reflux overnight. The reaction was monitored by TLC and shown to be incomplete in the morning. Another portion of benzyl bromide (20 mL, 0.168 mol) was added and the reaction allowed to reflux for an additional 2 hours. The reaction was then shown to be complete (2–4 hrs). The slurry was allowed to cool to room temperature and filtered through a sintered glass funnel. The filter cake was washed with acetone and the mother liquor was stripped to dryness in vacuo leaving a viscous oil.

The crude product was taken up in THF (300 mL) and MeOH (150 mL). To this solution was added lithium hydroxide monohydrate (62.94 g. 1.5 mol) and the solution stirred at room temperature until complete by TLC. The slurry was filtered through a sintered glass funnel; collecting the lithium salt of the product. The cake was washed with THF, air dried, and then slurried in 1HCl until acidic. The acid was then filtered and dried overnight. The product was then dissolved in EtOAc and dried with MgSO$_4$. The solvent stripped under vacuum and hexane added and stripped until product became solid. The solid was then slurried in hexane, collected on a sintered glass funnel, and dried overnight to yield the title compound. $^1$H NMR (CDCl$_3$) δ 2.70 (t, 2 H), 2.96 (t, 2 H), 5.07 (s, 2 H), 6.87 (br m, 3 H), 7.25 (br m, 1 H), 7.42 (br m, 5 H).

Example YYYY 3-(3-Benzyloxy-phenyl)-1-cyclopentyl-propan-1-one 3-(3-Benzyloxy-phenyl)-propanoic acid (5 g, 19.5 mmol) from Example XXXX was taken up in thionyl chloride (20 mL) and refluxed for 2 hours. The excess thionyl chloride was removed under reduced pressure and carbon tetrachloride added and removed several times under reduced pressure to remove any excess thionyl chloride. The resulting oil was taken up in freshly distilled THF (50 mL), MnCl$_2$ (0.49 g, 3.9 mmol) and LiCl (0.331 g, 7.8 mmol) were added. This was allowed to stir under nitrogen at room temperature until homogenous. The solution was then cooled to 0° C. with an ice bath and 2.0 M cyclopentyl magnesium chloride (11.0 mL, 22 mmol) in Et$_2$O was added dropwise to the solution over 0.5 hour. The reaction was allowed to stir for 10 minutes after addition was complete and was then quenched with 1N HCl and brine until acidic. The organics were extracted into EtOAc and then washed with brine and dried with MgSO$_4$. The solvent was removed under reduced pressure and the residue submitted to flash chromatography (3:7 EtOAc:hexane, silica gel) to yield the title compound as a viscous oil. $^1$H NMR (CDCl$_3$) δ 1.54–1.80 (br m, 8 H), 2.76 (m, 2 H), 2.80 (m, obscured, 1 H), 2.86 (m, 2 H), 5.05 (s, 2 H), 6.81 (br m, 3 H), 7.21 (br m, 1 H), 7.43 (br m, 5 H).

Example ZZZZ

6-[2-(3-Benzyloxy-phenyl)-ethyl]-6-cyclopentyl-4-hydroxy-5,6-dihydro-pyran-2-one The title compound was prepared as described in General Method 6 using 3-(3-benzyloxy-phenyl)-1-cyclopentyl-propan-1-one (3.3 g, 11.3 mmol) from Example YYYY, 2.45 mL (22.7 mmol) of methyl acetoacetate, 0.93 g (23.2 mmol) of 60% NaH dispersion in mineral oil, 14.5 mL (1.6 M, 23.2 mmol) of n-butyllithium and 40 mL of THF. The reaction mixture was quenched with 5 mL HOAc and the mixture was worked up in the normal manner.

The above crude product was cyclized as described in General Method 7 using the crude aldol product, 85 mL of THF and 600 mL of 0.1N NaOH. The product was purified by column chromatography using silica gel and eluting with a mixture of EtOAc:hexane:CH$_2$Cl$_2$ (1:1: 1) to give the product as an oil in 85% yield. $^1$H-NMR (DMSO-d$_6$) δ 1.3–1.7 (m, 8 H), 1.85–1.95 (m, 2 H), 2.3 (t, 1 H), 2.4–2.6 (m, 2 H, partially obscured by DMSO), 3.2–3.4 (q, 2 H, partially obscured by water), 4.95 (s, 1 H), 5.1 (s, 2 H), 6.75–6.85 (m, 3 H), 7.15 (t, 1 H), 7.3–7.45 (m, 5 H).

Example AAAAA

6-Cyclopentyl-4-hydroxy-6-[2-(3-hydroxy-phenyl)-ethyl]-5,6-dihydro-pyran-2-one

The dihydropyrone 6-[2-(3-benzyloxy-phenyl)-ethyl]-6-cyclopentyl-4-hydroxy-5,6-dihydro-pyran-2-one (prepared in Example ZZZZ, 2.92 g, 7.4 mmol) was hydrogenated according to General Method 4 to remove the benzyl protecting group, affording the product in quantitative yield. $^1$H-NMR (DMSO-d$_6$) δ 1.3–1.7 (m, 8 H), 1.85–1.95 (m, 2 H), 2.35 (t, 1 H), 2.4–2.6 (m, 4 H), 4.95 (s, 1 H), 6.55–6.6 (m, 3 H), 7.05 (t, 1 H), 9.25 (s, 1 H), 11.35 (s, 1 H).

Example BBBBB 5-(3-Benzyloxy-phenyl)-3-cyclopentyl-3-hydroxy-pentanoic acid tert-butyl ester Diisopropyl amine (9.56 mL, 68.2 mmol) was dissolved in freshly distilled THF (30 mL) and cooled to –15° C. with a dry ice/acetone bath. 1.6 M n-BuLi (42.7 mL, 68.2 mmol) in hexanes was then added dropwise over 20 minutes. The solution was then cooled to -40° C. and allowed to stir for 20 minutes. tert-Butyl acetate (9.2 mL, 68.2 mmol) was then dissolved in freshly distilled THF (20 mL) and added dropwise over 30 minutes to the –40° C. solution. This was allowed to stir for an additional 30 minutes at 40° C. after addition was complete. 3-(3-Benzyloxy-phenyl)-1-cyclopentyl-propan-1 -one (10.51 g, 34.1 mmol) from Example YYYY was dissolved in freshly distilled THF (35 mL) and added rapidly to the –40° C. solution, such that the temperature did not exceed –40° C. Monitored reaction with TLC and shown to be complete in 5 minutes. Added glacial acetic acid dropwise (20 mL) to neutralize solution and allowed to warm to room temperature. The majority of THF was removed under reduced pressure and took up remaining organics in EtOAc. The organics were washed with brine, saturated sodium bicarbonate, and again with brine. The organics were dried over MgSO$_4$ and the solvent removed under reduced pressure. The residue was flash chromatographed (15% EtOAc/85% hexane, silica gel) to yield the title compound as a viscous oil. $^1$H NMR (CDCl$_3$) δ 1.47 (s, 9 H), 1.47–1.69 (br m, 8 H), 1.83 (m, 2 H), 2.08 (m, 1 H), 2.46 (d of ABX q, 1 H), 2.49 (d of ABX q, 1 H), 2.63 (m, 2 H), 3.78 (br s, 1 H), 5.05 (s, 2 H), 6.82 (br m, 3 H), 7.26 (t, 1 H), 7.32–7.46 (br m, 5 H).

Example CCCCC (S) 5-(3-Benzyloxy-phenyl)-3-cyclopentyl-3-hydroxy-pentanoic acid tert-butyl ester The enantiomers of Example BBBBB were resolved on a Chiracel OD column eluting with 95% iso-octane/5% iso-propanol with 0.5% total trifluoroacetic acid at a flow rate of 1 mL/min. Under these conditions the two enantiomers were detected (214 nm) at retention times of 7.75 minutes and 9.60 minutes.

Example DDDDD (S) 5-(3-Benzyloxy-phenyl)-3-cyclopentyl-3-hydroxy-pentanoic acid

The title compound was prepared by dissolving (S) 5-(3-benzyloxy-phenyl)-3-cyclopentyl-3-hydroxy-pentanoic acid tert-butyl ester (1.6 g, 3.8 mmol) from Example CCCCC in methanol (20 mL). Lithium hydroxide (0.32 g, 7.6 mmol) in H$_2$O (5 mL) was added and the reaction heated to reflux overnight, cooled and pumped to dryness under vacuum. The product was partitioned between H$_2$O and Et$_2$O. The aqueous layer was decanted, acidified with 1N HCl and extracted with EtOAc. The organic phase was dried (MgSO$_4$), and concentrated to give the title compound. $^1$H-NMR (CDCl$_3$) δ 1.3–1.7 (m, 8 H), 1.85–1.95 (m, 2 H), 2.3 (t, 1 H), 2.45–2.7 (m, 4 H), 5.1 (s, 2 H), 6.75–6.85 (m, 3 H), 7.15 (t, 1 H), 7.3–7.45 (m, 5 H).

Example EEEEE (S) 6-[2-(3-Benzyloxy-phenyl)-ethyl]-6-cyclopentyl-4-hydroxy-5,6-dihydro-pyran-2-one The title compound was prepared using (S)-5-(3-benzyloxy-phenyl)-3-cyclopentyl-3-hydroxy-pentanoic acid (0.92 g, 2.51 mmol) from Example DDDDD, THF (30 mL), and CDI (0.49 g, 3.02 mmol). The reaction was stirred overnight at room temperature then added to bis[3-ethoxy-3-oxopropanoato(1-)-O,O']-magnesate (2.15 g, 7.5 mmol) from Example VVVV and the reaction stirred overnight at room temperature. The reaction was concentrated and the residue partitioned between EtOAc and IN HCl. The organic layer was washed with aqueous NaHCO$_3$ and brine, dried (MgSO$_4$) and concentrated.

The crude product was cyclized as described in General Method 7 using 10 mL of THE and 150 mL of 0.1N NaOH. Purification by silica gel chromatography, eluting with CH₂Cl₂:MeOH (98:2) gave the title compound. ¹H-NMR (CDCl₃) δ 1.4–1.8 (m, 8 H), 1.85–1.95 (m, 2 H), 2.15 (t, 1 H), 2.6 (m, 2 H), 2.8 (q, 2 H), 3.4 (q, 2 H), 5.1 (s, 2 H), 6.75–6.85 (m, 3 H), 7.15 (t, 1H), 7.3–7.45 (m, 5 H).

Example FFFFF (S)-6-Cyclopentyl-4-hydroxy-6-[2-(3-hydroxy-phenyl)-ethyl]-5,6-dihydro-pyran-2-one The title compound was prepared as described in General Method 4 using (S)-6-[2-(3-benzyloxy-phenyl)-ethyl]-6-cyclopentyl-4-hydroxy-5,6-dihydro-pyran-2-one (0.64 g, 1.63 mmol) from Example EEEEE, 0.1 g of 20% Pd over charcoal and THF (16 mL). Purification by silica gel chromatography, eluting with CH₂Cl₂:MeOH (97.5:2.5) gave the title compound. ¹H-NMR (DMSO-d₆) δ 1.3–1.7 (m, 8 H), 1.85–1.95 (m, 2 H), 2.35 (t, 1 H), 2.4–2.6 (m, 4 H), 4.95 (s, 1 H), 6.55–6.6 (m, 3 H), 7.05 (t, 1 H), 9.25 (s, 1 H), 11.35 (s, 1 H).

Example GGGGG 5-(4-Amino-phenyl)-2-methyl-pentan-3-one

A mixture of 13.6 g (62 mmol) of 2-methyl-5-(4-nitro-phenyl)-pentan-3-one (Y. Huang, L. Shi, S. Li, *Synthesis*, 1988, 975–977), 400 mL of THF, and 2.6 g of Raney Nickel was shaken in a hydrogen atmosphere (24 p.s.i.) at 25° C. for 56 hours. The catalyst was filtered, and the filtrate was concentrated to give the title compound. ¹H NMR (CDCl₃) δ 1.01 (d, 6 H), 2.46–2.55 (m, 1 H), 2.65–2.83 (m, 4 H), 3.55 (br s, 2 H), 6.56 (d, 2 H), 6.92 (d, 2 H).

Example HHHHH

[4-(4-Methyl-3-oxo-pentyl)-phenyl]-carbamic acid benzyl ester

A solution of 11.9 g (62 mmol) of crude 5-(4-amino-phenyl)-2-methyl-pentan-3-one (prepared in Example GGGGG) in 100 mL of acetonitrile was treated with 24.3 g (75 mmol) of cesium carbonate, and the mixture was stirred at 50° C. for 15 minutes. Benzyl chloroformate (10.7 mL, 75 mmol) was added all at once, and the mixture was stirred at room temperature for 90 minutes. The solvent was evaporated. The residue was partitioned between EtOAc and H₂O; the organic layer was separated, washed with brine, dried (MgSO₄), and concentrated. The product was chromatographed on silica gel, eluting with EtOAc:hexane (30:70), to give the title compound. ¹H NMR (CDCl₃) δ 1.01 (d, 6 H), 2.48–2.55 (m, 1 H), 2.67–2.82 (m,4 H), 5.15 (s, 2 H), 6.58 (br s, 1 H), 7.08 (d, 2 H), 7.25–7.38 (m, 7 H).

Example IIIII

3-[2-(4-Benzyloxycarbonylamino-phenyl)-ethyl]-3-hydroxy-4-methyl-pentanoic acid benzyl ester A solution of 21.9 mL (156 mmol) of diisopropylamine in dry THF (100 mL) was cooled to −40° C. under nitrogen, treated dropwise with 125 mL of 1.2 M n-BuLi (150 mmol), and stirred for 30 minutes. To this solution was added a solution of 22.5 g (150 mmol) of benzyl acetate in dry THF (70 mL). The mixture was stirred at −40° C. for 45 minutes and then treated with a solution of 16.2 g (50 mmol) of [4-(4-methyl-3-oxo-pentyl)-phenyl]-carbamic acid benzyl ester (prepared in Example HHHHH) at a rapid, dropwise rate. When addition was complete, the reaction mixture was stirred at −40° C. for 30 minutes. Acetic acid (50 mL) was added, and the mixture was warmed to room temperature. EtOAc and H₂O were added. The organic layer was separated, washed with brine, and dried (MgSO₄). Concentration gave a residue which was chromatographed on silica gel, eluting with EtOAc:hexane (40:60), to give the title compound. ¹H NMR (CDCl₃) δ 0.88–0.91 (t, 6 H), 1.65–1.75 (m, 2 H), 1.85–1.89 (m, 1 H), 2.46–2.61 (m, 4 H), 3.52 (s, 1 H), 5.11 (s, 2 H), 5.16 (s, 2 H), 6.55 (br s, 1 H), 7.02 (d, 2 H), 7.24–7.38 (m, 12 H).

Example JJJJJ (S)-(3-[2-(4-Benzyloxycarbonylamino-phenyl)-ethyl]-3-hydroxy-4-methyl-pentanoic acid benzyl ester (+/−)-3-[2-(4-Benzyloxycarbonylamino-phenyl)-ethyl]-3-hydroxy-4-methyl-pentanoic acid benzyl ester (13.5 g, 28 mmol) from Example IIIII was separated into its enantiomers by a chiral chromatographic HPLC method. The column utilized was a Chiracel AD prep-column (2 cm×25 cm, 10 micron particle size). The mobil phase consisted of 36% IPA and 64% Heptane. The flow rate was 9–11 mL/min. The wavelength was monitored at 275 nm. The injection size was 10 mL of mobil phase which contained 200 mg (0.4 mmol) of the racemic material. The S enantiomer (peak 1) began eluting at 26 minutes and was collected for 10 minutes consisting of two 50 mL fractions. A recycle peak was collected between 36 and 38 minutes which contained the tail of the first peak and the front of the second peak. The R enantiomer (peak #2) was collected for 15 minutes (38–53 minutes) and consisted of three 50 mL fractions. This process was repeated several times and the fractions for peak #1 combined and stripped of its solvent in vacuo. The crystalline solid that was obtained was slurried in Et₂O and triturated with hexane. The solid was filtered and dried to yield the title compound, a white crystalline solid. ¹H NMR (CDCl₃) δ 0.89 (t, 6 H), 1.62–1.76 (m, 2 H), 1.78–1.91 (m, 1 H) 2.49 (d of abq, 1 H), 2.52–2.59 (m, 2 H), 2.57 (d of abq, 1 H) 3.51 (s, 1 H), 5.11 (s, 2 H), 5.16 (s, 2 H), 6.55 (br s, 1 H), 7.03 (d, 2 H), 7.24 (d partially obscured by CDCl₃, 2 H), 7.27–7.39 (m, 10 H).

Example KKKKK (S)-(3-[2-(4-Amino-phenyl)-ethyl]-3-hydroxy-4-methyl-pentanoic acid To a Parr shaker was charged (S)-(3-[2-(4-benzyloxycarbonylamino-phenyl)-ethyl]-3-hydroxy-4-methyl-pentanoic acid benzyl ester (4.11 g, 8.6 mmol) from Example JJJJJ, 20% Pd/C (0.5 g) and THF (100 mL) respectively. The reactor was then charged with hydrogen gas (50 psi) and allowed to shake for 3 hours. The reaction was filtered through a sintered glass funnel and stripped of its solvent in vacuo and dried under reduced pressure to yield the title compound. ¹H NMR (CDCl₃) δ 0.64 (t, 6 H), 1.41–1.48 (m, 2 H), 1.52–1.57 (m, 1 H), 2.13 (d of abq, 1 H), 2.19 (d of abq, 1 H), 2.21–2.27 (m, 2 H), 6.28 (d, 2 H), 6.62 (d, 2 H).

Example LLLLL (S)-(3-[2-(4-tert-Butoxycarbonylamino-phenyl)-ethyl]-3-hydroxy-4-methyl-pentanoic acid To a round bottom flask was charged (S)-(3-[2-(4-amino-phenyl)-ethyl]-3-hydroxy-4-methyl-pentanoic acid (2.2 g, 8.7 mmol) from Example KKKKK and anhydrous THF (50 mL). To the resulting solution was charged di-tert -butyl dicarbonate (2.0 g, 9.15 mmol) and the resulting solution allowed to reflux overnight. The reaction was then cooled to room temperature and stripped of its solvent in vacuo. The resulting residue was taken up in a small amount of Et₂O and triturated with hexane. The solid was filtered and dried to yield the title compound. ¹H NMR (CDCl₃) δ 0.90 (t, 6 H), 1.46 (s, 9 H), 1.67–1.78 (m, 2 H), 1.85–1.95 (m, 1 H), 2.41

(d of abq, 1 H), 2.48 (d of abq, 1 H), 2.55–2.61 (m, 2 H), 6.80 (s, 1 H), 7.06 (d, 2 H), 7.21 (d, 2 H).

Example MMMMM (S)-(5-[2-(4-tert-Butoxycarbonylamino-phenyl)-ethyl]-5-hydroxy-6-methyl-3-oxo-heptanoic acid ethyl ester To a round bottom flask was charged (S)-(3-[2-(4-tert-butoxycarbonylaminophenyl)-ethyl]-3-hydroxy-4-methyl-pentanoic acid (1.1 g, 3.12 mmol) from Example LLLLL and anhydrous THF (25 mL). To this solution was added CDI (1.0 g, 6.24 mmol). The solution was allowed to stir at room temperature for 4.5 hours. Bis[3-ethoxy-3-oxopropanoato(1-)-O,O']-magnesate (1.78 g, 6.24 mmol) from Example VVVV was then added and the reaction allowed to stir overnight at room temperature. The reaction was then quenched with 1N HCl and brine, and then extracted with EtOAc (3×). The organics were combined, washed with brine, dried with MgSO$_4$, and stripped of solvent in vacuo. The residue was submitted to flash chromatography (silica gel, 60% hexanes/40% EtOAc) to yield the title compound. $^1$H NMR (CDCl$_3$) δ 0.93 (t, 6 H), 1.25 (t, 3 H), 1.50 (s, 9 H), 1.74–1.80 (m, 2 H), 1.92–2.00 (m, 1 H), 2.57–2.63 (m, 2 H), 2.67 (d of abq, 1 H), 2.72 (d of abq, 1 H), 3.47 (s, 2 H), 3.60 (s, 1 H), 4.16–4.23 (m, 2 H), 6.80 (s, 1 H), 7.06 (d, 2 H), 7.21 (d, 2 H).

Example NNNNN (S)-((4-[2-(4-Hydroxy-2-isopropyl-6-oxo-3,6-dihydro-2H-pyran-2-yl)-ethyl]-phenyl)-carbamic acid tert-butyl ester To a round bottom flask was charged (S)-(5-[2-(4-tert-butoxycarbonylamino-phenyl)-ethyl]-5-hydroxy-6-methyl-3-oxo-heptanoic acid ethyl ester (2.9 g, 6.90 mmol) from Example MMMMM and THF (25 mL). To this solution was rapidly added 0.1N NaOH (250 mL, 25 mmol) and the reaction allowed to stir overnight. The next day the aqueous solution was washed with Et$_2$O and then acidified to pH 6.5 with saturated ammonium chloride solution. The resulting precipitate was extracted with EtOAc (3×). The organics were combined, washed with brine, and dried with MgSO$_4$. The solvent was removed under reduced pressure to yield the title compound. $^1$H NMR (CDCl$_3$) δ (dd, 6 H), 1.51 (s, 9 H), 1.74–1.83 (m, 1 H), 1.95–2.03 (m, 1 H), 2.04–2.13 (m, 1 H), 2.61–2.70 (m, 2 H), 2.69 (d of abq, 1 H), 2.76 (d of abq, 1 H), 3.41 (s, 2 H), 6.43 (br s, 1 H), 7.05 (d, 2 H), 7.26 (d, 2 H).

Example OOOOO (S)-((4-{2-[5-(2-tert-Butyl-4-hydroxymethyl-5-methyl-phenylsulfanyl)-4-hydroxy-2-isopropyl-6-oxo-3,6-dihydro-2H-pyran-2-yl]-ethyl}-phenyl)-carbamic acid tert-butyl ester To a round bottom flask was charged (S)-({4-[2-(4-hydroxy-2-isopropyl-6-oxo-3,6-dihydro-2H-pyran-2-yl)-ethyl]-phenyl}-carbamic acid tert-butyl ester (1.20 g, 3.2 mmol) from Example NNNNN, toluene-4-thiosulfonic acid S-(2-tert-butyl-4-hydroxymethyl-5-methyl-phenyl) ester prepared in Example FFF (1.22 g, 3.35 mmol), K$_2$CO$_3$ (1.76 g, 12.80 mmol), and DMF (5.0 mL). The reaction was allowed to stir at room temperature for 5 hours under a blanket of nitrogen. The reaction was then quenched with H$_2$O (20 mL) then 1.0N NaOH (20 mL). The aqueous base was washed with Et$_2$O and then acidified to pH 7.0 with saturated NH$_4$HPO$_4$. The resulting precipitate was partitioned into EtOAc (3×). The organics were combined, washed with brine (2×), and dried with MgSO$_4$. The solvent was removed under reduced pressure and dried on high vacuum line to yield the title compound. $^1$H NMR (DMSO-d$_6$) δ (dd, 6 H), 1.45 (s, 9 H), 1.47 (s, 9 H), 1.88 (s, 3 H), 1.92–1.97 (m, 2 H), 1.98–2.20 (m, 1 H), 2.52–2.57 (m, 2 H), 2.78 (d of abq, 1 H), 2.93 (d of abq, 1 H), 4.13 (s, 2 H), 6.67 (s, 1 H), 7.05 (d, 2 H), 7.26 (s, 1 H), 7.30 (d, 2 H), 9.22 (br s, 1 H).

Example PPPPP

[4-(4-Methyl-3-oxo-pentyl)-phenyl]-carbamic acid 1,1-dimethylethyl ester

A solution of 1.5 g (7.8 mmol) of 5-(4-amino-phenyl)-2-methyl-pentan-3-one (prepared in Example GGGGG), di-t-butyl dicarbonate (1.9 g, 8.7 mmol) and THF (30 mL) was heated to 50° C. overnight. The mixture was cooled to room temperature and concentrated; the residue was partitioned between EtOAc and H$_2$O. The organic layer was washed with brine, dried (MgSO$_4$), and concentrated. Purification via silica gel chromatography, eluting with hexane:EtOAc (4:1), gave the title compound. $^1$H NMR (CDCl$_3$) δ 1.01 (d, 6 H), 1.46 (s, 9 H), 2.50 (m, 1 H), 2.68 (m, 2 H), 2.75 (m, 2 H), 6.46 (br s, 1 H), 7.05 (d, 2 H), 7.22 (m, 2 H).

Example QQQQQ

{4-[2-(4-Hydroxy-2-isopropyl-6-oxo-3,6-dihydro-2H-pyran-2-yl)-ethyl]-phenyl)-carbamic acid 1,1-dimethylethyl ester The title compound was prepared from [4-(4-methyl-3-oxo-pentyl)-phenyl]-carbamic acid 1, I -dimethylethyl ester obtained in Example PPPPP (2.1 g, 7.2 mmol), methyl acetoacetate (2.1 g, 18.1 mmol), 60% NaH (0.80 g, 20 mmol), and n-butyllithium (14 mL of 1.5 M, 21 mmol) in THF as described in General Method 6. The product was carried on crude to the next step.

The residue obtained above (2.9 g, 7.2 mmol) was cyclized using 1N NaOH (500 mL) and THF (50 mL) as described in General Method 7. After acidification to pH 5.5, the solution was extracted with EtOAc. The extract was washed with brine, dried (MgSO$_4$), and concentrated. The title compound was obtained after column chromatography on silica gel, eluting with 2% MeOH in CH$_2$Cl$_2$. $^1$H NMR (DMSO-d$_6$) δ 0.84 (m, 6 H), 1.40 (s, 9 H), 1.83 (m, 2 H), 2.05 (m, 1 H), 2.25 (d of ABX q, 1 H), 2.47 (m, partially obscured by DMSO, 2 H), 2.54 (d of ABX q, 1 H), 4.91 (s, 1 H), 7.00 (d, 2 H), 7.27 (d, 2 H), 9.17 (br s, 1 H), 11.3 (br s, 1 H).

Reference Agent A 3-(2-tert-Butyl-5-methyl-phenylsulfanyl)-4-hydroxy-6,6-diphenethyl-5,6-dihydro-pyran-2-one The title compound was prepared as described in General Method 9 from 233 mg (0.7 mmol) of 4-hydroxy-6,6-diphenethyl-5,6-dihydro-pyran-2-one (prepared in Example OOOO), 290 mg (0.84 mmol, 1.2 equivalents) of 2-tert-butyl-5-methylphenyl-p-toluenethiosulfonate (prepared in Example LLLL), 400 mg (2.8 mmol, 4 equivalents) potassium carbonate, and 8 mL of DMF. The reaction was stirred overnight under a nitrogen atmosphere and then worked up in the usual manner. The residue was chromatographed on silica gel eluting with 1:1 EtOAc:CH$_2$Cl$_2$+2% methanol, to give the title compound.

Reference Agent B 3-(2-tert-Butyl-5-methyl-phenylsulfanyl)-4-hydroxy-6-phenethyl-6-phenyl-5,6-dihydro-pyran-2-one, (+/−)

A solution of 0.40 g (1.35 mmol) of 4-hydroxy-6-phenethyl-6-phenyl-5,6-dihydro-pyran-2-one (U.S. patent application Ser. No. 08/319,820), 0.50 g (1.50 mmol) of 2-tert-butyl-5-methylphenyl-p-toluenethiosulfonate (prepared in Example LLLL), 0.20 mL (1.4 mmol) of NEt₃, 1.13 g (13 mmol) of NaHCO₃, and 25 mL of EtOH was stirred at room temperature overnight. The solution was concentrated, and the residue was partitioned between CHCl₃ and saturated NH₄Cl. The organic layer was washed with brine, dried (MgSO₄), and concentrated. The residue was chromatographed on silica gel, eluting with 4:1 hexane:EtOAc, to give the title compound, m.p. 71–74° C.

Reference Agent C 3-(2-tert-Butyl-5-methyl-phenylsulfanyl)-4-hydroxy-6-(3-methyl-butyl)-6-phenethyl-5,6-dihydro-pyran-2-one To a 25 mL reaction flask was added 42 mg (1.04 mmol) of NaH 60% dispersion in oil which was washed (2×20 mL) with hexane. THF (15 mL) was added and the reaction cooled to 0° C. The 4-hydroxy-6-(3-methyl-butyl)-6-phenethyl-5,6-dihydro-pyran-2-one (prepared in Example PPPP; 150 mg, 0.52 mmol) was added and the reaction stirred for 30 minutes at 0° C. 2-tert-Butyl-5-methylphenyl-p-toluenethiosulfonate (prepared in Example LLLL; 174 mg, 0.52 mmol) was added and the reaction stirred at room temperature for 5 days. The reaction was worked up by pouring into EtOAc and 2N HCl. The layers were separated and the aqueous layer extracted again with EtOAc. The combined organic extracts were dried (MgSO₄) and concentrated. The crude product was flash chromatographed using CH₂Cl₂:MeOH (99:1 to 98:2) to give the title compound, m.p. 46–50° C.

Example 1

3-[2-tert-Butyl-4.(2-hydroxy-ethoxy)-5-methyl-phenylsulfanyl]-4-hydroxy-6-[2-(4-hydroxy-phenyl)-ethyl]-6-methyl-5,6-dihydro-pyran-2-one, (+/−)

The title compound was prepared as described in General Method 9 using 4-hydroxy-6-[2-(4-hydroxy-phenyl)-ethyl]-6-methyl-5,6-dihydro-pyran-2-one (prepared in Example KK; 0.5 g, 2.03 mmol), toluene 4-thiosulfonic acid S-[2-tert-butyl-4-(2-methoxymethoxy-ethoxy)-5-methyl-phenyl] ester(prepared in Example BBBB; 0.91 g, 2.03 mmol), anhydrous K₂CO₃ (1.0 g) and 5 mL of DMF. The crude compound was purified by flash silica gel column chromatography, eluting with EtOAc:hexane (1:4, then switching to 1:1), m.p. 88–90° C. ¹H-NMR (DMSO-d₆) δ 1.29 (s, 3 H), 1.35 (s, 9 H), 1.83–2.0 (m, 2 H), 1.92 (s, 3 H), 2.45–2.61 (m, 2 H), 2.78 (d of ABX q, 1 H), 2.97 (d of ABX q, 1 H), 3.28 (s, 3 H), 3.76 (t, 2 H), 4.1 (t, 2 H), 4.63 (s, 2 H), 6.67 (d, 2 H), 6.75 (s, 1 H), 6.83 (s, 1 H), 6.97 (d, 2 H), 9.14 (s, 1 H), 11.86 (br s, 1 H).

The protecting group was removed using 0.125 g (0.24 mmol) of 3-[2-tert-butyl-4-(2-methoxymethoxy-ethoxy)-5-methyl-phenylsulfanyl]-4-hydroxy-6-[2-(4-hydroxy-phenyl)-ethyl]-6-methyl-5,6-dihydro-pyran-2-one (prepared in the previous paragraph), 2 mL of THF, 2 mL of MeOH and 2 mL of concentrated HCl. The reaction mixture was stirred overnight, and the solvents were evaporated. The residue was triturated from EtOAc and Et₂O to afford the title compound, m.p. 203–205° C. ¹H-NMR (DMSO-d₆) δ 1.42 (s, 3 H), 1.49 (s, 9 H), 1.86–2.0 (m, 2 H), 1.92 (s, 3 H), 2.47–2.58 (m, 2 H), 2.75 (d of ABX q, 1 H), 2.94 (d of ABX q, 1 H), 3.69 (br s, 2 H), 3.95 (t, 2 H), 4.81 (br s, 1 H), 6.67 (d, 2 H), 6.75 (s, 1 H), 6.8 (s, 1 H), 6.97 (d, 2 H), 9.17 (s, 1 H).

Example 2

3-[2-tert-Butyl-4-hydroxymethyl-5-methyl-phenylsulfanyl]-4-hydroxy-6-[2-(4-hydroxy-phenyl)-ethyl]-6-isopropyl-5,6-dihydro-pyran-2-one, (+/−)

The title compound was prepared as described in General Method 9 using 0.15 g (0.41 mmol) of 4-hydroxy-6-[2-(4-hydroxy-phenyl)-ethyl]-6-isopropyl-5,6-dihydro-pyran-2-one (prepared in Example LL), 0.16 g (0.45 mmol) of toluene-4-thiosulfonic acid S-(2-tert-butyl-4-hydroxymethyl-5-methyl-phenyl) ester (prepared in Example FFF), 0.5 g of anhydrous K₂CO₃ and 3 mL of DMF. The crude material was purified by flash silica gel chromatography, eluting with EtOAc:hexane (1:4, then switching to 4:1), to give the title compound, m.p. 116–118° C. ¹H-NMR (DMSO-d₆) δ 0.92 (d, 3 H), 0.96 (d, 3 H), 1.49 (s, 9 H), 1.89 (s, 3 H), 1.92–2.0 (t, 2 H), 2.2 (m, 1 H), 2.35–2.6 (m, 2 H), 2.75 (d of ABX q, 1 H), 2.97 (d, ABX q, 1 H), 4.36 (s, 2 H), 4.94 (br s, 1 H), 6.65 (d, 2 H), 6.69 (s, 1 H), 6.96 (d, 2 H), 7.28 (s, 1 H), 9.15 (s, 1 H), 11.97 (br s, 1 H).

Example 3

Ethyl-sulfamic acid 5-tert-Butyl-4-(4-hydroxy-6-[2-(4-hydroxy-phenyl)-ethyl]-6-methyl-2-oxo-5,6-dihydro-2H-pyran-3-ylsulfanyl}-phenyl ester, (+/−)

The title compound was prepared as described in General Method 9 using 0.075 g (0.27 mmol) of 4-hydroxy-6-[2-(4-hydroxy-phenyl)-ethyl]-6-methyl-5,6-dihydro-pyran-2-one (prepared in Example KK), 0.12 g (0.27 mmol) of toluene-4-thiosulfonic acid S-(2-tert-butyl-4-ethylsulfamoyloxy-5-methyl-phenyl) ester (prepared in Example VVV), 0.15 g of anhydrous K₂CO₃ and 2 mL of DMF. The crude material was purified by flash silica gel chromatography, eluting with EtOAc:hexane (1:4, then switching to 4:1), to give the title compound m.p. 102–104° C. ¹H-NMR (DMSO-d₆) δ 1.14 (t, 3 H), 1.44 (s, 3 H), 1.49 (s, 9 H), 1.97 (m, 2 H), 2.06 (s, 3 H), 2.56 (t, 2 H), 2.82 (d of ABX q, 1 H), 3.01 (d of ABX q, 1 H), 3.14 (m, 2 H), 6.67 (d, 2 H), 6.83 (s, 1 H), 7.0 (d, 2 H), 7.13 (s, 1 H), 8.38 (t, 1 H), 9.17 (s, 1 H).

Example 4

Dimethyl-sulfamic acid 5-tert-Butyl-4-{4-hydroxy-6-[2-(4-hydroxy-phenyl)-ethyl]-6-methyl-2-oxo-5,6-dihydro-2H-pyran-3-ylsulfanyl]-phenyl ester, (+/−)

The title compound was prepared as described in General Method 9 using 0.15 g (0.62 mmol) 4-hydroxy-6-[2-(4-hydroxy-phenyl)-ethyl]-6-methyl-5,6-dihydro-pyran-2-one (prepared in Example KK), 0.29 g (0.62 mmol) of toluene-4-thiosulfonic acid S-(2-tert-butyl-4-dimethylsulfamoyloxy-5-methyl-phenyl) ester (prepared in Example UUU), 0.25 g of anhydrous K₂CO₃ and 3 mL of DMF. The crude material was purified by flash silica gel chromatography, eluting with EtOAc:hexane (1:4, then switching to 4: 1), to give the title compound, m.p. 181–183° C. ¹H-NMR (DMSO-d₆) δ 1.44 (s, 3 H), 1.47 (s, 9 H), 1.96 (m, 2 H), 2.06 (s, 3 H), 2.56 (t, 2 H), 2.81 (d of ABX q, 1 H), 2.94 (s, 6 H), 3.04 (d of ABX q, 1 H), 6.67 (d, 2 H), 6.83 (s, 1 H), 6.97 (d, 2 H), 7.15 (s, 1 H), 9.17 (s, 1 H).

Example 5

3-[2-tert-Butyl-4-(2-hydroxy-ethoxy)-5-methyl-phenylsulfanyl] -4-hydroxy-6-[2-(4-hydroxy-phenyl)-ethyl]-6-isopropyl-5,6-dihydro-pyran-2-one, (+/−)

The title compound was prepared as described in General Method 9 using 0.15 g (0.41 mmol) 4-hydroxy-6-[2-(4-hydroxy-phenyl)-ethyl]-6-isopropyl-5,6-dihydro-pyran-2- one (prepared in Example LL), 0.28 g (0.62 mmol) of toluene 4-thiosulfonic acid S-[2-tert-butyl-4-(2-methoxymethoxy-ethoxy)-5-methyl-phenyl] ester (prepared in Example BBBB), 0.5 g of anhydrous $K_2CO_3$ and 2 mL of DMF. The crude compound was purified by flash silica gel column chromatography, eluting with EtOAc:hexane (1:4, then switching to 1:1).

The protecting group was removed using 0.12 g (0.22 moles) 3-[2-tert-butyl-4-(2-methoxymethoxy-ethoxy)-5-methyl-phenylsulfanyl]4-hydroxy-6-[2-(4-hydroxy-phenyl)-ethyl]-6-isopropyl-5,6-dihydro-pyran-2-one prepared above, 2 mL of THF, 2 mL of MeOH, and 2 mL of concentrated HCl. The reaction mixture was stirred overnight, and the solvents were evaporated. The residue was triturated from EtOAc and $Et_2O$ to afford the title compound, m.p. 90–92° C. $^1$H-NMR (DMSO-$d_6$) δ 8 0.92 (d, 3 H), 0.96 (m, 4 H), 1.47 (s, 9 H), 1.81 (s, 3 H), 1.93 (t, 2 H), 2.43–2.56 (m, 2 H), 2.72 (d of ABX q, 1 H), 2.81 (d of ABX q, 1 H), 3.67 (br s, 2 H), 3.94 (t, 2 H), 4.81 (br s, 1 H), 6.64 (d, 2 H), 6.72 (s, 1 H), 6.81 (s, 1 H), 6.94 (d, 2H), 9.14 (s, 1 H), 11.86 (br s, 1 H).

Example 6 tert-Butyl-sulfamic acid 5-tert-Butyl-4-{4-hydroxy-6-[2-(4-hydroxy-phenyl)-ethyl]-6-methyl-2-oxo-5,6-dihydro-2H-pyran-3-ylsulfanyl}-2-methyl-phenyl ester, (+/−)

The title compound was prepared as described in General Method 9 using 0.15 g (0.62 mmol) 4-hydroxy-6-[2-(4-hydroxy-phenyl)-ethyl]-6-methyl-5,6-dihydro-pyran-2-one (prepared in Example KK), 0.3 g (0.62 mmol) of toluene-4-thiosulfonic acid S-(2-tert-butyl-4-tert-butylsulfamoyloxy-5-methyl-phenyl) ester (prepared in Example YYY), 0.25 g of anhydrous $K_2CO_3$ and 2 mL of DMF. The residue was purified by flash silica gel chromatography, eluting with EtOAc:hexane (1:4, then switching to 95:5), to give the title compound, m.p. 108–110° C. $^1$H-NMR (DMSO-$d_6$) δ 0.33 (s, 9 H), 1.44 (s, 3 H), 1.5 (s, 9 H), 1.94 (m, 2 H), 2.04 (s, 3 H), 2.56 (t, 2 H), 2.81 (d of ABX q, 1 H), 3.01 (d of ABX q, 1 H), 6.67 (d, 2 H), 6.85 (s, 1 H), 7.0 (d, 2 H), 7.22 (s, 1 H), 8.19 (s, 1 H), 9.17 (s, 1 H).

Example 7

6-Butyl-3-[2-tert-butyl-4-hydroxymethyl-5-methyl-phenylsulfanyl]-4-hydroxy-6-[2-(4-hydroxy-phenyl)-ethyl]-5,6-dihydro-pyran-2-one, (+/−)

The title compound was prepared as described in General Method 9 using 0.2 g (0.69 mmol) of 6-butyl-4-hydroxy-6-[2-(4-hydroxy-phenyl)-ethyl]-5,6-dihydro-pyran-2-one (prepared in Example MM), 0.28 g (0.76 mmol) of toluene-4-thiosulfonic acid S-(2-tert-butyl-4-hydroxymethyl-5-methyl-phenyl) ester (prepared in Example FFF), 0.25 g of anhydrous $K_2CO_3$ and 3 mL of DMF. The crude compound was purified by flash silica gel chromatography, eluting with EtOAc:hexane (3:7, then switching to 4:1) m.p. 128–130° C. $^1$H-NMR (DMSO-$d_6$) δ 0.89 (t, 3 H), 1.31 (m, 4 H), 1.5 (s, 9 H), 1.64 (m, 2 H), 1.89–2.03 (m, 2 H), 1.97 (s, 3 H), 2.44–2.56 (m, 2 H), 2.83 (d of ABX q, 1 H), 2.94 (d of ABX q, 1 H), 4.24 (s, 2 H), 4.97 (br s, 1 H), 6.67 (d, 2 H), 6.72 (s, 1 H), 6.97 (d, 2 H), 7.28 (s, 1 H), 9.17 (s, 1 H), 12.0 (br s, 1 H).

Example 8

Ethyl-sulfamic acid 5-tert-butyl-4-(6-cyclohexyl-4-hydroxy-6-[2-(4-hydroxy-phenyl)-ethyl]-2-oxo-5,6-dihydro-2H-pyran-3-ylsulfanyl}-2-methyl-phenyl ester The title compound was prepared as described in General Method 9 from 6-cyclohexyl-4-hydroxy-6-[2-(4-hydroxy-phenyl)-ethyl]-5,6-dihydro-pyran-2-one (156 mg, 0.499 mmol; prepared in Example NN), toluene-4-thiosulfonic acid S-(2-tert-butyl-4-ethylsulfamoyloxy-5-methyl-phenyl) ester (prepared in Example VVV; 250 mg, 0.546 mmol), $K_2CO_3$ (303 mg, 2.195 mmol), and DMF (4 mL). The reaction was stirred at room temperature for 2.5 hours and then worked up in the usual manner. The crude product was flash chromatographed using $CH_2Cl_2$:MeOH (98:2 to 97:3) to give the desired product as a amorphous solid. $^1$H NMR (CDCl$_3$) δ 1.0–2.1 (m, 16 H), 1.55 (s, 9 H), 2.00 (s, 3 H), 2.6–2.7 (m, 3 H), 3.10 (d, 1 H), 3.3–3.4 (m,2 H), 4.96 (t, 1 H), 6.70–6.78 (d, s, 3 H), 6.93 (d, 2 H), 7.29 (s, 1 H).

Example 9

3-(2-tert-Butyl-4-hydroxymethyl-5-methyl-phenylsulfanyl)-6-cyclohexyl-4-hydroxy-6-[2-(4-hydroxy-phenyl)-ethyl]-5,6-dihydro-pyran-2-one The title compound was prepared as described in General Method 9 from 6-cyclohexyl-4-hydroxy-6-[2-(4-hydroxy-phenyl)-ethyl]-5,6-dihydro-pyran-2-one (prepared in Example NN; 156 mg, 0.499 mmol), toluene-4-thiosulfonic acid S-(2-tert-butyl-4-hydroxymethyl-5-methyl-phenyl) ester (prepared in Example FFF; 250 mg, 0.546 mmol), $K_2CO_3$ (303 mg, 2.195 mmol), and DMF (4 mL). The reaction was stirred at room temperature for 2.5 hours and then worked up in the usual manner. The crude product was flash chromatographed using $CH_2Cl_2$: MeOH (98:2) to give the desired product as a solid, m.p. 138–139° C. (dec.). $^1$H NMR (CDCl$_3$) δ 1.0–2.1 (m, 13 H), 1.58 (s, 9 H), 2.03 (s, 3 H), 2.6–2.7 (m, 3 H), 3.05 (d, 1 H), 4.6 (s, 2 H), 6.69–6.74 (d, s, 3 H), 6.98 (d, 2 H), 7.34 (s, 1 H), 7.74 (s, 1 H).

Example 10

3-(2-tert-Butyl-4-hydroxy-5-methyl-phenylsulfanyl)-6-cyclohexyl-4-hydroxy-6-[2-(4-hydroxy-phenyl)-ethyl]-5,6-dihydro-pyran-2-one The title compound was prepared as described in General Method 9 from 6-cyclohexyl-4-hydroxy-6-[2-(4-hydroxy-phenyl)-ethyl]-5,6-dihydro-pyran-2-one (prepared in Example NN; 210 mg, 0.664 mmol), toluene-4-thiosulfonic acid S-(2-tert-butyl-4-hydroxy-5-methyl-phenyl) ester (prepared in Example RRR; 256 mg, 0.730 mmol), $K_2CO_3$ (367 mg, 2.655 mmol), and DMF (4 mL). The reaction was stirred at room temperature overnight and then worked up in the usual fashion. The crude product was flash chromatographed using $CH_2Cl_2$:MeOH (98:2) to give the desired product as a solid, m.p. 100–103° C. $^1$H NMR (DMSO-$_6$) δ 1.0–2.1 (m, 13 H), 1.45 (s, 9 H), 1.80 (s, 3 H), 2.5–2.6 (2 H +DMSO), 2.7 (d, 1 H), 2.9 (d, 1 H), 6.6–6.7 (d, s, 3 H), 6.77 (s, 1 H), 6.9 (d, 2 H), 9.01 (s, 1 H), 9.13 (s, 1 H).

Example 11

3-(4-Amino-2-tert-butyl-5-methyl-phenylsulfanyl)-4-hydroxy-6-[2-(4-hydroxy-phenyl)-ethyl]-6-methyl-5,6-dihydro-pyran-2-one monohydrochloride The title compound was prepared as described in General Method 9 from 4-hydroxy-6-[2-(4-hydroxy-phenyl)-ethyl]-6-methyl-5,6-dihydro-pyran-2-one (prepared in Example KK; 0.25 g, 1.0 mmol), DMF (12 mL), $K_2CO_3$ (0.31 g, 2.2 mmol), and [5-(1,1-dimethylethyl)-2-methyl-4-[[(4- methylphenyl)sulfonyl]-thio]phenyl]-imidodicarbonic acid bis(1,1-dimethylethyl) ester (prepared in Example GGGG; 0.55 g, 1.0 mmol). The mixture was stirred at room temperature overnight. Following standard work-up, the residue obtained was flash chromatographed on silica gel, eluting with 19:1 CHCl$_3$:MeOH. The isolated solid was dissolved in CH$_2$Cl$_2$ (50 mL) and HCl (gas) was bubbled in while stirring at room temperature for 30 minutes. Solvent was then removed in vacuo; the residue was triturated with Et$_2$O, filtered and washed with EtOAc to give the title compound, m.p. 158–168° C. (dec.). $^1$H NMR (DMSO-d$_6$) δ 1.46 (s, 3 H), 1.48 (s, 9 H), 1.96 (m, 2 H), 2.07 (s, 3 H), 2.56 (m, 2 H), 2.85 (d of ABX q, 1 H), 3.04 (d of ABX q, 1 H), 6.68 (d, 2 H), 6.80 (s, 1 H), 7.00 (d, 2 H), 7.29 (s, 1 H), 9.19 (br s, 1 H), 10.14 (br s, 3 H).

Example 12

N-[4-[[5,6-Dihydro-4-hydroxy-6,6-bis[2-(4-hydroxyphenyl)ethyl]-2-oxo-2H-pyran-3- yl]thio]-5-(1,1-dimethylethyl)-2-methylphenyl]-N',N'-dimethyl-sulfamide The title compound was prepared as described in General Method 9 from 4-hydroxy-6,6-bis-[2-(4-hydroxy-phenyl)-ethyl]-5,6-dihydro-pyran-2-one (prepared in Example PP; 0.16 g, 0.46 mmol), DMF (6 mL), K$_2$CO$_3$ (0.14 g, 1.01 mmol), and (4-methyl-benzenesulfonothioic acid[4-[[(dimethylamino)-sulfonyl]amino]-2-(1,1-dimethylethyl)-5-methylphenyl] ester) (prepared in Example IIII; 0.21 g, 0.46 mmol). The mixture was stirred at room temperature overnight. After the standard work-up, the resulting residue was flash chromatographed on silica gel, eluting with 19:1 CHCl$_3$:MeOH, then triturated with EtOAc:Et$_2$O:hexanes to afford the title compound. $^1$H NMR (DMSO-d$_6$) δ 1.43 (s, 9 H), 1.88 (s, 3 H), 1.97 (m, 4 H), 2.51 (m, partially obscured by DMSO, 4 H), 2.66 (s, 6 H), 2.91 (br s, 2 H), 6.64 (d, 4 H), 6.68 (s, 1 H), 6.97 (d, 4 H), 7.21 (s, 1 H), 8.83 (s, 1 H), 9.15 (s, 2 H).

Example 13

N-(5-tert-Butyl-4-{4-hydroxy-6-[2-(4-hydroxy-phenyl)-ethyl]-6-methyl-2-oxo-5,6-dihydro-2H-pyran-3-ylsulfanyl}-2-methyl-phenyl)-4-cyano-benzenesulfonamide The title compound was prepared as described in General Method 9 from 4-hydroxy-6-[2-(4-hydroxy-phenyl)-ethyl]-6-methyl-5,6-dihydro-pyran-2-one (prepared in Example KK; 0.09 g, 0.37 mmol), DMF (6 mL), K$_2$CO$_3$ (0.11 g, 0.81 mmol), and toluene-4-thiosulfonic acid S-[2-tert-butyl-4-(4-cyano-benzenesulfonylamino)-5-methyl-phenyl] ester (prepared in Example JJJJ; 0.19 g, 0.37 mmol). The mixture was stirred at room temperature overnight. After the standard work-up, the resulting residue was flash chromatographed on silica gel, eluting with 2% EtOH:EtOAc, then triturated with EtOAc:CH$_2$Cl$_2$:hexanes to afford the title compound. $^1$H NMR (DMSO-d$_6$) δ 1.24 (s, 9 H), 1.42 (s, 3 H), 1.87 (s, 3 H), 1.92 (m, 2 H), 2.52 (m, partially obscured by DMSO, 2 H), 2.75 (d of ABX q, 1 H), 2.95 (d of ABX q, 1 H), 6.46 (s, 1 H), 6.64 (d, 2 H), 6.70 (s, 1 H), 6.96 (d, 2 H), 7.77 (d, 2 H), 8.06 (d, 2 H), 9.15 (s, 1 H), 9.68 (s, 1 H).

Example 14

3-(2-tert-Butyl-4-hydroxymethyl-5-methyl-phenylsulfanyl)-4-hydroxy-6,6-bis-[2-(4-hydroxyphenyl) ethyl]-5,6-dihydro-pyran-2-one The title compound was prepared as described in General Method 9 using 0.14 g (0.39 mmol) of 4-hydroxy-6,6-bis [2-(4-hydroxyphenyl)ethyl]-5,6-dihydro-pyran-2-one (prepared in Example PP), 0.19 g (0.52 mmol) of toluene-4-thiosulfonic acid S-(2-tert-butyl-4-hydroxymethyl-5-methyl-phenyl) ester (prepared in Example FFF), 0.22 g (1.6 mmol) of K$_2$CO$_3$, and 3 mL of DMF. The solution was stirred overnight at room temperature. Purification by silica gel chromatography, eluting with CH$_2$Cl$_2$:MeOH (100:0 to 90:10), gave the title compound, m.p. 192–194° C. $^1$H NMR (DMSO-d$_6$) δ 1.48 (s, 9 H), 1.83 (s, 3 H), 2.02 (m, 4 H), 2.54 (m, 4 H), 2.96 (br s, 2 H), 4.35 (br s, 2 H), 4.94 (br a, 1 H), 6.68 (m, 5 H), 6.99 (dd, 4 H), 7.26 (s, 1 H), 9.16 (s, 2 H).

Example 15

6-[2-(4-aminophenyl)ethyl]-3-(2-tert-butyl-4-hydroxymethyl-5-methyl-phenylsulfanyl)-4-hydroxy-6-phenyl-5,6-dihydro-pyran-2-one The title compound was prepared as described in General Method 9 using 0.23 g (0.65 mmol) of N-{4-[2-(4-hydroxy-6-oxo-2-phenyl-3,6-dihydro-2H-pyran-2-yl)-ethyl]-phenyl}-acetamide (prepared in Example RR), 0.33 g (0.90 mmol) of toluene-4-thiosulfonic acid S-(2-tert-butyl-4-hydroxymethyl-5-methyl-phenyl) ester (prepared in Example FFF), 0.54 g (3.9 mmol) of K$_2$CO$_3$, and 5 mL of DMF. The solution was stirred overnight at room temperature and then poured into glacial acetic acid (5 mL) and EtOAc (20 mL). After standard work-up, the residue was triturated with Et$_2$O, and the solids were filtered. The penultimate intermediate was dissolved in H$_2$0 (30 mL), 50% NaOH (4 mL), and MeOH (5 mL) and was refluxed for 18 hours. The mixture was cooled to room temperature, concentrated, and suspended in phosphate buffer (pH 7.5). Acidification to pH 6.8 with phosphoric acid was followed by extraction with CH$_2$Cl$_2$. The combined extracts were washed with brine, dried (MgSO$_4$), and concentrated to give the title compound, m.p. 218–221° C. $^1$H NMR (DMSO-d$_6$) δ 1.44 (s, 9 H), 1.76 (s, 3 H), 2.05–2.22 (m, 3 H), 2.40 (m, 1 H), 3.40 (m, partially obscured by H$_2$O, 2 H), 4.32 (s, 2 H), 4.90 (br s, 1 H), 6.17 (s, 1 H), 6.47 (d, 2 H), 6.75 (d, 2 H), 7.21 (s, 1 H), 7.38–7.43 (m, 5 H).

Example 16

6,6-Bis-[2-(4-aminophenyl)ethyl]-3-(2-tert-butyl-4-hydroxymethyl-5-methyl-phenylsulfanyl)-4-hydroxy-5,6-dihydro-pyran-2-one The title compound was prepared as described in General Method 9 using 0.38 g (0.69 mmol) of (1,1-dimethylethyl) [(3,6-dihydro-4-hydroxy-6-oxo-2H-pyran-2,2-diyl)bis[2,1-ethanediyl-(4,1-phenylene)]biscarbamate prepared in Example OO, 0.35 g (0.96 mmol) of toluene-4-thiosulfonic acid S-(2-tert-butyl-4-hydroxymethyl- 5-methyl-phenyl) ester (prepared in Example FFF), 0.58 g (4.2 mmol) of K$_2$CO$_3$, and 5 mL of DMF. The reaction mixture was stirred overnight, and then poured into glacial acetic acid (5 mL) and EtOAc (20 mL). After standard workup, the residue was chromatographed on silica gel, eluting with 1:1 hexane:EtOAc, to give the BOC-protected intermediate. This material was dissolved in CH$_2$Cl$_2$, cooled in an ice bath, and treated with a steady stream of gaseous HCl for 10 minutes. The solvent was evaporated. The residue was suspended in H$_2$O which was then made basic to pH 11.5 with 10% NaOH and stirred for 20 minutes. The solution was made basic to pH 6.5 with HOAc and extracted with EtOAc (3×50 mL). The combined extracts were washed with brine, dried (MgSO$_4$), and concentrated to give the title compound, m.p. 144–146° C. $^1$H NMR (DMSO-d$_6$) δ 1.43 (s, 9 H), 1.81 (s, 3 H), 1.95 (m, 4 H), 2.42 (m, partially obscured by DMSO, 4 H), 2.87 (br s, 2 H), 4.30 (s, 2 H), 4.90 (br s, 1 H), 6.45 (d, 4 H), 6.65 (s, 1 H), 6.80 (d, 4 H), 7.20 (s, 1 H).

Example 17

3-(tert-Butyl-4-hydroxymethyl-5-methyl-phenylsulfanyl)-4-hydroxy-6-phenethyl-6-phenyl-5,6-dihydro-pyran-2-one (S isomer)

The title compound was prepared as described in General Method 9 using 0.12 g (0.40 mmol) of (S)-4-hydroxy-6-phenethyl-6-phenyl-5,6-dihydro-pyran-2-one (prepared in Example VV), 0.16 g (0.44 mmol) of toluene-4-thiosulfonic acid S-(2-tert-butyl-4-hydroxymethyl-5-methyl-phenyl) ester (prepared in Example FFF), 0.22 g (1.6 mmol) of $K_2CO_3$, and DMF (2 mL). Upon standard work-up, the residue was chromatographed on silica gel, eluting with 4:1 $CHCl_3$:EtOAc, to give the title compound, m.p. 186–187° C. $^1$H NMR (DMSO-$d_6$) δ (s, 9 H), 1.75 (s, 3 H), 2.25 (m, 3 H), 2.55 (m, 1 H), 3.51 (q, partially obscured by $H_2O$, 2 H), 4.32 (br s , 2 H), 4.90 (br s , 1 H), 6.17 (s, 1 H), 7.09 (m, 2 H), 7.15 (m, 1 H), 7.23 (m, 3 H), 7.37 (m, 1 H), 7.44 (m, 4 H).

Example 18

3-[2-tert-Butyl-4-(2-hydroxy-ethoxy)-5-methyl-phenylsulfanyl]-4-hydroxy-6,6-bis-[2-(4-hydroxy-phenyl)-ethyl]-5,6-dihydro-pyran-2-one The title compound was synthesized using General Method 9 using 0.07 g (2 mmol) of 4-hydroxy-6,6-bis-[2-(4-hydroxy-phenyl)-ethyl]-5,6-dihydro-pyran-2-one (prepared in Example PP), 1.00 g (2 mmol) of toluene-4-thiosulfonic acid S-{2-tert-butyl-4-[2-(tert-butyl-dimethyl-silanyloxy)-ethoxy]-5-methyl-phenyl} ester (prepared in Example PPP), 1.06 g (8 mmol) $K_2CO_3$, and DMF (5 mL). The solid which was obtained was then dissolved in 20 mL MeOH and 2 mL of IN HCl. After 15 minutes the reaction was concentrated and the residue partitioned between EtOAc and $H_2O$; the organic layer was separated, dried ($Na_2SO_4$) and concentrated. Trituration with $Et_2O$ yielded the title compound, m.p. 106–107° C. $^1$H NMR (DMSO-$d_6$) δ 1.49 (s, 9 H), 1.75 (s, 3 H), 2.0 (t, 4 H), 2.5 (t, 4 H), 3.4 (dd, 2 H), 3.7 (bs, 2 H), 3.95 (t, 2 H), 4.8 (br s, 1 H), 6.66 (d, 4 H), 6.7 (s, 1 H), 6.8 (s, 1 H), 6.98 (d, 4 H), 9.17 (s, 2 H).

Example 19

(5-tert-Butyl-4-{4-hydroxy-6,6-bis-[2-(4-hydroxy-phenyl)-ethyl]-2-oxo-5,6-dihydro-2H-pyran-3-ylsulfanyl}-2-methyl-phenoxy)-acetic acid ethyl ester The title compound was synthesized via General Method 9 using 209 mg (0.6 mmol) of 4-hydroxy-6,6-bis-[2-(4-hydroxy-phenyl)-ethyl]-5,6-dihydro-pyran-2-one (prepared in Example PP), 250 mg (0.6 mmol) of [5-tert-butyl-2-methyl-4-(toluene-4-sulfonylsulfanyl)-phenoxy]-acetic acid (prepared in Example NNNN), 327 mg (2.4 mmol) of $K_2CO_3$, and DMF (2 mL). The reaction was conducted in EtOH to effect ester exchange. The reaction was worked up as described. The residue was chromatographed on silica gel eluting with (1:1 $CH_2Cl_2$:EtOAc+2% MeOH) to yield the product, m.p. 162–163° C. $^1$H NMR (DMSO-$d_6$) δ 1.21 (t, 3 H), 1.47 (s, 9 H), 1.8 (s, 3 H), 2.0 (m, 4 H), 2.6 (m, 6 H), 2.95 (s, 2 H), 4.25 (q, 2 H), 4;75 (s, 2 H), 6.65 (m, 5 H), 6.75 (s, 1 H), 7.0 (d 4 H), 9.18 (s, 2 H).

Example 20

3-(4-Amino-2-tert-butyl-5-methyl-phenylsulfanyl)-4-hydroxy-6,6-bis [2-(4-hydroxy-phenyl)ethyl]-5,6-dihydro-pyran-2-one The compound was synthesized following General Method 9 using 118 mg (0.33 mmol) of 4-hydroxy-6,6-bis-[2-(4-hydroxy-phenyl)-ethyl]-5,6-dihydro-pyran-2-one (prepared in Example PP), 150 mg (0.33 mmol) of toluene-4-thiosulfonic acid S-(4-amino-2-tert-butyl-5-methyl-phenyl) ester (prepared in Example HHHH), 184 mg (1.32 mmol) of $K_2CO_3$ and 2 mL of DMF. The reaction was worked up by partitioning between EtOAc and $H_2O$. The organic layer was separated and concentrated, then triturated with $Et_2O$. The resultant solid was placed in chilled HCl-saturated $CH_2Cl_2$ and stirred for 18 hours. After concentration, the residue was triturated with $Et_2O$ to yield the title compound, m.p. 140–145° C. $^1$H NMR (DMSO-$d_6$) δ 1.5 (s, 9 H), 1.9 (s, 3 H), 2.05 (m, 4 H), 2.5 (m, 6 H), 6.68 (d, 4 H), 6.75 (s, 1 H), 7.0 (d, 4 H), 7.35 (s, 1 H), 7.95 (s 2 H), 9.25 (s, 2 H).

Example 21

3-(2-tert-Butyl-4-hydroxymethyl-5-methyl-phenylsulfanyl)-4-hydroxy-6,6-bis-[2-(3-hydroxy-phenyl)ethyl]-5,6-dihydro-pyran-2-one The compound was synthesized following General Method 9 and using 172 mg (0.5 mmol) of 4-hydroxy-6,6-bis-[2-(3-hydroxy-phenyl)-ethyl]-5,6-dihydro-pyran-2-one (prepared in Example XX), 179 mg (0.5 mmol) of toluene-4-thiosulfonic acid S-(2-tert-butyl-4-hydroxymethyl-5-methyl-phenyl) ester (prepared in Example FFF), 270 mg (2.0 mmol) of $K_2CO_3$, and 2 mL of DMF. The reaction was worked up as described and chromatographed on silica get eluting with (1:1 $CH_2Cl_2$:EtOAc+2% MeOH), to yield the title compound, m.p. 92–94° C. $^1$H NMR (DMSO-$d_6$) δ 1.48 (s, 9 H), 1.80 (s, 3 H), 2,07 (m, 4 H), 2.6 (m, 4 H), 3.0 (s, 2 H), 4.35 (s, 2 H), 6.6 (m, 6 H), 6.65 (s, 1 H), 7.05 (t, 2 H), 7.25 (s, 1 H), 9.25 (s, 2 H).

Example 22

Dimethyl-sulfamic acid 5-tert-butyl-4-{4-hydroxy-6,6-bis-[2-(3-hydroxy-phenyl)-ethyl]-2-oxo-5,6-dihydro-2H-pyran-3-ylsulfanyl}-2-methyl-phenyl ester The compound was synthesized following General Method 9 and using 77 mg (0.2 mmol) of 4-hydroxy-6,6-bis-[2-(3-hydroxy-phenyl)-ethyl]-5,6-dihydro-pyran-2-one (prepared in Example XX), 100 mg (0.2 mmol) of toluene-4-thiosulfonic acid S-(2-tert-butyl-4-dimethylsulfamoyloxy-5-methyl-phenyl) ester (prepared in Example UUU), 18 mg (0.8 mmol) of $K_2CO_3$ and 5 mL of DMF. The reaction was worked up as described and chromatographed on silica gel, eluting with (1:1 $CH_2Cl_2$:EtOAc+2% MeOH), to give the title compound. $^1$H NMR (DMSO-$d_6$) δ 1.45 (s, 9 H), 1.9 (s, 3 H), 2.95 (m, 4 H), 2.6 (m, 4 H), 2.95 (s, 6 H), 3.35 (m, 2 H), 6.60 (m, 6 H), 6.8 (s, 1 H), 7.05 (t, 2 H), 7.15 (s, 1 H), 9.25 (s, 2 H).

Example 23

3-[2-tert-Butyl-4-(2-hydroxy-ethoxy)-5-methyl-phenylsulfanyl]-4-hydroxy-6,6-bis[2-(4-hydroxy-3-methoxy-phenyl)-ethyl]-5,6-dihydro-pyran-2-one The compound was prepared using General Method 9 and the following quantities: 100 mg (0.24 mmol) of 4-hydroxy-6,6-bis-[2-(4-hydroxy-3-methoxy-phenyl)-ethyl]-5,6-dihydro-pyran-2-one (prepared in Example QQ), 123 mg (0.24 mol) of toluene-4-thiosulfonic acid S-{2-tert-butyl-4-[2-(tert-butyl-dimethyl-silanyloxy)-ethoxy]-5-methyl-phenyl} ester (prepared in Example PPP), 133 mg (0.96 mmol) of $K_2CO_3$, and 10 mL of DMF. The reaction was worked up by addition of 10 mL 1. ON HCl and stirring for 10 minutes, followed by extraction with EtOAc. The organic layer was dried ($Na_2SO_4$), concentrated, and chromatographed on silica gel, eluting with (1:1 $CH_2Cl_2$:EtOAc+2%

MeOH), to give the title compound, m.p. 76–82° C. $^1$H NMR (DMSO-d$_6$) δ 1.5 (s, 9 H), 1.75 (s, 3 H), 2.05 (m, 4 H), 2.6 (m, 4 H), 2.95 (s, 2 H), 3.7 (m, 8 H), 3.95 (t, 2 H), 4.8 (br s, 1 H), 6.65 (m, 7 H), 7.0 (s, 1 H), 8.75 (s, 2 H).

Example 24

3-(2-tert-Butyl-4-hydroxy-5-methyl-phenylsulfanyl)-4-hydroxy-6-[4-(2-hydroxy-ethoxy)-phenyl]-6-phenethyl-5,6-dihydro-pyran-2-one The title compound was prepared as described in General Method 9 using 6-{4-[2-(tert-butyl-dimethyl-silanyloxy)-ethoxy]-phenyl}-4-hydroxy-6-phenethyl-5,6-dihydro-pyran-2-one (prepared in Example SS; 0.200 g, 0.43 mmol), toluene-4-thiosulfonic acid S-[2-tert-butyl-4-(tert-butyl-dimethyl-silanyloxy)-5-methyl-phenyl] ester prepared in Example JJJ (0.26 g, 0.56 mmol), K$_2$CO$_3$ (0.24 g, 1.7 mmol), and DMF (2.0 mL). After consumption of starting material, the mixture was diluted with MeOH and treated with 10 drops of concentrated HCl. The mixture was stirred for 20 minutes and then diluted with 15 mL of H$_2$O and extracted with CH$_2$Cl$_2$. The organic layers were combined, dried (Na$_2$SO$_4$) and concentrated. The product was purified by column chromatography (CH$_2$Cl$_2$ to 4% MeOH in CH$_2$Cl$_2$) to provide a solid, m.p. 168–170° C. (dec.). $^1$H NMR (DMSO-6) δ 1.41 (s, 9 H), 1.63 (s, 3 H), 2.29–2.16 (m, 4 H), 3.32 (d, 1 H, partially obscured by H$_2$0), 3.38 (d, 1 H, partially obscured by H$_2$O), 3.98 (t, 2 H), 3.72 (br d, 2 H), 4.88 (br s, 1 H), 6.07 (s, 1 H), 6.71 (s, 1 H), 6.83 (d, 2 H), 7.09 (d, 2 H), 7.17–7.13 (m, 1 H), 7.26–7.22 (m, 2 H), 7.31 (d, 2 H), 8.91 (s, 1 H).

Example 25

3-[2-tert-Butyl-4-(2-hydroxy-ethoxy)-5-methyl-phenylsulfanyl]-4-hydroxy-6-[4-(2-hydroxy-ethoxy)-phenyl] -6-phenethyl-5,6-dihydro-pyran-2-one To a round bottom flask equipped with a magnetic stirrer were added 6-{4-[2-(tert-butyl-dimethyl-silanyloxy)-ethoxy]-phenyl} -4-hydroxy-6-phenethyl-5,6-dihydro-pyran-2-one (prepared in Example SS; 0.260 g, 0.555 mmol), toluene-4-thiosulfonic acid S-{2-tert-butyl-4-[2-(tert-butyl-dimethyl-silanyloxy)-ethoxy]-5-methyl-phenyl) ester (prepared in Example PPP; 0.282 g, 0.555 mmol), K$_2$CO$_3$ (0.346 g, 2.50 mmol), and DMF (5 mL), as described in General Method 9. The mixture was stirred at room temperature for 2 days at which time MeOH (150 mL) was added and the solution taken to pH 3.0 with conc. HCl. The reaction was quenched with H$_2$O (500 mL) and extracted with EtOAc. The organics were dried over MgSO$_4$ and concentrated; the residue was taken up in a small amount of EtOAc and triturated with hexane. The solid was filtered and dried under high vacuum to yield the title compound, m.p. >190° C. (dec.). $^1$H NMR (DMSO-d$_6$) δ 1.45 (s, 9 H), 1.68 (s, 3 H), 2.22 (br m, 4 H), 2.51 (br m, partially obscured by DMSO, 2 H), 3.34 (d of ABX q, partially obscured by H$_2$0, 1 H), 3.40 (d of ABX q, partially obscured by H$_2$O, 1 H), 3.67 (br m, 2 H), 3.72 (br m, 2 H)3.91 (t, 2 H), 3.98 (t, 2 H), 6.76 (s, 1 H), 6.96 (s, 1 H), 6.99 (d, 2 H), 7.08–7.22 (m, 1 H), 7.10 (d, 2 H), 7.24 (d, 2 H), 7.30 (d, 2 H).

Example 26

Dimethyl-sulfamic acid 5-tert-butyl-4-{4-hydroxy-2-oxo-6-phenethyl-6-[4-(2-piperazin-1-yl-ethoxy)-phenyl]-5,6-dihydro-2H-pyran-3-ylsulfanyl}-2-methyl-phenyl ester To a round bottom flask equipped with a magnetic stirrer were added toluene-4-thiosulfonic acid S-(2-tert-butyl-4-dimethylsulfamoyloxy-5-methyl-phenyl) ester (prepared in Example UUU; 0.176 g, 0.383 mmol), 4-(2-{[4-hydroxy-6-oxo-2-phenethyl-3,6-dihydro-2H-pyran-2-yl]-phenoxy}ethyl)-piperazine-1-carboxylic acid tert-butyl ester (prepared in Example WW; 0.200 g, 0.383 mmol), K$_2$CO$_3$ (0.221 g, 1.60 mmol), and DMF (8 mL), as described in General Method 9. The slurry was stirred at room temperature overnight. After standard work-up, the residue was submitted to flash chromatography (97% CHCl$_3$, 3% MeOH). The product obtained was taken up in CH$_2$Cl$_2$ (40 mL), cooled to 0° C, and treated with gaseous HCl for 30 minutes. The solvent was evaporated and the residue taken up in a small amount of MeOH, triturated and neutralized with KH$_2$PO$_4$ buffer (pH 7.5). The solids were filtered, washed with H$_2$O followed by Et$_2$O, and dried overnight under high vacuum to yield the title compound, m.p. 181° C. (dec.). $^1$H NMR (DMSO-d$_6$) δ 1.40 (s, 9 H), 1.78 (s, 3 H), 2.12 (br m, 2 H), 2.64 (br m, 4 H), 2.75 (br m, 2 H), 2.79 (br m, 4 H), 2.89 (s, 6 H), 3.34 (d of ABX q, obscured by H$_2$0, 2 H), 3.40 (d of ABX q, obscured by H$_2$O, 2 H), 4.04 (br t, 2 H), 6.87–7.36 (br m, 11 H).

Example 27

Dimethyl-sulfamic acid 5-tert-butyl-4-{4-hydroxy-6,6-bis-[2-(4-hydroxy-phenyl)-ethyl]-2-oxo-5,6-dihydro-2H-pyran-3-ylsulfanyl}-2-methyl-phenyl ester To a round bottom flask equipped with a magnetic stirrer were added toluene-4-thiosulfonic acid S-(2-tert-butyl-4-dimethylsulfamoyloxy-5-methyl-phenyl) ester (prepared in Example UUU; 0.128 g, 0.280 mmol), 4-hydroxy-6,6-bis-[2-(4-hydroxy-phenyl)-ethyl]-5,6-dihydro-pyran-2-one (prepared in Example PP; 0.100 g, 0.280 mmol), K$_2$CO$_3$ (0.154 g, 1.12 mmol), and DMF (8 mL), as described in General Method 9. The slurry was stirred at room temperature overnight. After standard work-up, the residue was submitted to flash chromatography (97% CHCl$_3$:3% MeOH) to yield the title compound, m.p. 139° C. $^1$H NMR (CDCl$_3$) δ 1.53 (s, 9 H), 1.91 (s, 3 H), 2.11 (m, 4 H), 2.65 (m, 4 H), 2.86 (s, 2 H), 2.98 (s, 6 H), 4.80 (br s, 2 H), 6.72 (s, 1 H), 6.73 (d, 4 H), 6.98 (d, 4 H), 7.27 (s, 1 H).

Example 28

Ethyl-sulfamic acid 5-tert-butyl-4-{4-hydroxy-6,6-bis-[2-(4-hydroxy-phenyl)-ethyl]-2-oxo-5,6-dihydro-2H-pyran-3-ylsulfanyl}-2-methyl-phenyl ester To a round bottom flask equipped with a magnetic stirrer were added 4-hydroxy-6,6-bis-[2-(4-hydroxy-phenyl)-ethyl]-5,6-dihydro-pyran-2-one (prepared in Example PP; 0.100 g, 0.280 mmol), toluene-4-thiosulfonic acid S-(2-tert-butyl-4-ethylsulfamoyloxy-5-methyl-phenyl) ester (prepared in Example VVV; 0.128 g, 0.280 mmol), K$_2$CO$_3$ (0.154 g, 1.12 mmol), and DMF (8 mL), as described in General Method 9. The reaction was stirred at room temperature for 2 hours and then worked up in the usual manner. The residue was submitted to flash chromatography (95% CHCl$_3$:5% MeOH). The product obtained was taken up in a small amount of EtOAc, triturated with hexane, filtered and dried overnight under high vacuum to yield the title compound, m.p. 130° C. (dec.). $^1$H NMR (CDCl$_3$) δ 1.22 (t, 3 H), 1.52 (s, 9 H), 1.92 (s, 3 H), 2.11 (m, 4 H), 2.66 (m, 4 H), 2.87 (s, 2 H), 3.31 (m, 2 H), 4.52 (br t, 1 H), 4.78 (br s, 2 H), 6.73 (d, 4 H), 6.98 (d, 4 H), 7.25 (s, 1 H), 7.70 (s, 1 H).

Example 29

Ethyl-sulfamic acid 5-tert-butyl-4-{6,6-bis-[2-(4-aminophenyl)-ethyl]4-hydroxy-2-oxo-5,6-dihydro-2H-pyran-3-ylsulfanyl}2-methyl-phenyl ester To a round bottom flask equipped with a magnetic stirrer were added toluene-4-thiosulfonic acid S-(2-tert-butyl-4-ethylsulfamoyloxy-5-methyl-phenyl) ester (prepared in Example VVV; 0.218 g, 0.470 mmol), (1,1-dimethylethyl)[(3,6-dihydro-4-hydroxy-6-oxo-2H-pyran-2,2-diyl)bis[2,1-ethanediyl-(4, 1 -phenylene)]-biscarbamate (prepared in Example OO; 0.200 g, 0.380 mmol), $K_2CO_3$ (0.260 g, 1.88 mmol), and DMF (8 mL), as described in General Method 9. The reaction was stirred at room temperature for 3 hours and then worked up in the usual fashion. The residue was submitted to flash chromatography (100% EtOAc). The product form chromatography was taken up in EtOAc, triturated with hexane, filtered, and then taken up in $CH_2Cl_2$ (20 mL). Gaseous HCl was bubbled into this solution for 30 minutes. The solids that formed were filtered, washed with $Et_2O$ and dried under high vacuum to yield the title compound, m.p. 194° C. $^1H$ NMR (DMSO-$d_6$) δ 1.14 (t, 3 H), 1.49 (s, 9 H), 1.88 (s, 3 H), 2.09 (br m, 4 H), 2.70 (br m, 4 H), 3.12 (s, 2 H) 3.13 (m, 2 H), 6.79 (s, 1 H), 7.11 (s, 1 H), 7.27 (d, 4 H), 7.33 (d, 4 H), 8.40 (t, 1 H).

Example 30

4-Methyl-piperazine-1-sulfonic acid 5-tert-butyl-4-(4-hydroxy-6,6-bis-[2-(4-hydroxy-phenyl)-ethyl]-2-oxo-5,6-dihydro-2H-pyran-3-ylsulfanyl}-2-methyl-phenyl ester To a round bottom flask equipped with a magnetic stirrer were added 4-methyl-piperazine- 1 -sulfonic acid, 5-tert-butyl-2-methyl-4-(toluene-4-sulfonylsufanyl)-phenyl ester (prepared in Example WWW; 0.150 g, 0.290 mmol), 4-hydroxy-6,6-bis-[2-(4-hydroxy-phenyl)-ethyl]-5,6-dihydro-pyran-2-one (prepared in Example PP; 0.104 g, 0.290 mmol), $K_2CO_3$ (0.166 g, 1.20 mmol), and DMF (8 mL), as described in General Method 9. The reaction was stirred overnight at room temperature. The reaction was quenched with saturated $NH_4Cl$ solution and extracted with EtOAc; the insoluble product was filtered from the organic layer, washed with $H_2O$ followed by $Et_2O$, and dried under high vacuum at 50° C. to yield the title compound, m.p. 150° C. $^1H$ NMR (DMSO-$d_6$) δ 1.42 (s, 9 H), 1.83 (s, 3 H), 1.92 (br m, 4 H), 2.42 (s, partially obscured by DMSO, 3 H), 2.48 (br m, partially obscured by DMSO, 4 H), 2.71 (s, 2 H), 2.75 (br m, 4 H), 3.33 (br m, obscured by $H_2O$, 4 H), 6.62 (d, 4 H), 6.77 (s, 1 H), 6.92 (d, 4 H), 7.04 (s, 1 H), 9.10 (br s, 2 H).

Example 31

4-Methyl-piperazine-1-sulfonic acid 5-tert-butyl-4-{4-hydroxy-6-[2-(4-hydroxy-phenyl)-ethyl]-6-methyl-2-oxo-5,6-dihydro-2H-pyran-3-ylsulfanyl}-2-methyl-phenyl ester To a round bottom flask equipped with a magnetic stirrer were added 4-methyl-piperazine-1-sulfonic acid, 5-tert-butyl-2-methyl-4-(toluene-4-sulfonylsufanyl)-phenyl ester (prepared in Example WWW; 0.200 g, 0.390 mmol), 4-hydroxy-6-[2-(4-hydroxy-phenyl)-ethyl]-6-methyl-5,6-dihydro-pyran-2-one (prepared in Example KK; 0.097 g, 0.390 mmol), $K_2CO_3$ (0.221 g, 1.60 mmol), and DMF (8 mL), as described in General Method 9. The reaction was stirred at room temperature overnight and worked up in the standard fashion. The residue was submitted to flash chromatography (9:1 $CHCl_3$:MeOH). The product obtained was taken up in $Et_2O$, filtered and dried under high vacuum to yield the title compound, m.p. 240° C. (dec.). $^1H$ NMR (DMSO-$d_6$) δ 1.36 (s, 3 H), 1.42 (s, 9H), 1.87 (br m, 2 H), 1.97 (s, 3 H), 2.40 (s, 3 H), 2.50 (br m,2H),2.52 (d of ABX q, 1 H), 2.71 (br m, 4 H), 2.72 (d of ABX q, 1 H), 3.32 (br m, obscured by $H_2O$, 4 H), 6.61 (d, 2 H), 6.80 (s, 1 H), 6.92 (d, 2 H), 7.04 (s, 1 H), 9.10 (br s, 1 H).

Example 32

1-Methyl-1H-imidazole-4-sulfonic acid 5-tert-butyl-4-{4-hydroxy-6-[2-(4-hydroxy-phenyl)-ethyl]-6-methyl-2-oxo-5,6-dihydro-2H-pyran-3-ylsulfanyl}-2-methyl-phenyl ester To a round bottom flask equipped with a magnetic stirrer were added 1-methyl-1H-imidazole-4-sulfonic acid, 5-tert-butyl-2-methyl-4-(toluene-4-sulfonylsufanyl)-phenyl ester (prepared in Example XXX; 0.200 g, 0.404 mmol), 4-hydroxy-6-[2-(4-hydroxy-phenyl)-ethyl]-6-methyl-5,6-dihydro-pyran-2-one (prepared in Example KK; 0.100 g, 0.404 mmol), $K_2CO_3$ (0.221 g, 1.60 mmol), and DMF (8 mL) as described in General Method 9. The reaction was stirred at room temperature overnight and then worked up in the usual manner. The residue obtained was taken up in $CHCl_3$, diluted with $Et_2O$, filtered and dried under high vacuum at 50° C. overnight to yield the title compound, m.p. 160° C. (dec.). $^1H$ NMR (DMSO-$d_6$) δ 1.29 (s, 9 H), 1.40 (s, 3 H), 1.89 (br m, 2 H), 1.93 (s, 3 H), 2.48 (br m, 2 H), 2.80 (d of ABX q, 1 H), 2.94 (d of ABX q, 1 H), 3.66 (s, 3 H), 6.58 (s, 1 H), 6.62 (d, 2 H), 6.71 (s, 1 H), 6.93 (d, 3 H), 7.97 (s, 2 H), 9.12 (br s, 1 H).

Example 33

3-(2-tert-Butyl-5-methyl-phenylsulfanyl)-4-hydroxy-6-[4-(2-hydroxy-ethoxy)-phenyl]-6-phenethyl-5,6-dihydro-pyran-2-one The title compound was prepared as described in General Method 9 using 3.05 g (6.5 mmol) of 6-{4-[2-(tert-butyl-dimethyl-silanyloxy)-ethoxy]-phenyl}-4-hydroxy-6-phenethyl-5,6-dihydro-pyran-2-one from Example SS, 2.61 g (7.8 mmol) of 2-tert-butyl-5-methylphenyl-p-toluenethiosulfonate (prepared in Example LLLL), 3.6 g (26 mmol) of $K_2CO_3$, and 50 mL of DMF. The solution was stirred overnight at room temperature. Purification by silica gel chromatography, eluting with EtOAc:hexane (10:90 to 25:75), gave the requisite intermediate, m.p. 70–73° C.

Deprotection of 1.75 g (2.7 mmol) of 6-{4-[2-(tert-butyl-dimethyl-silanyloxy)-ethoxy]-phenyl } -3-(2-tert-butyl-5-methyl-phenylsulfanyl)-4-hydroxy-6-phenethyl-5,6-dihydro-pyran-2-one (prepared in the paragraph above) was accomplished as described in General Method 8 using 5.4 mL (5.4 mmol) of 1 M tetrabutylammonium fluoride and 10 mL of THF. Purification by silica gel chromatography, eluting with MeOH:(50% Hexane-50% $CH_2Cl_2$) (1:99 to 5:95) gave the title compound, m.p. 154–156° C.

Example 34

3-(2-tert-Butyl-5-methyl-phenylsulfanyl)-4-hydroxy-6-[4-(2-morpholin-4-yl-ethoxy)-phenyl]-6-phenethyl-5,6-dihydro-pyran-2-one 3-(2-tert-Butyl-5-methyl-phenylsulfanyl)-4-hydroxy-6-[4-(2-hydroxy-ethoxy)-phenyl]-6-phenethyl-5,6-dihydro-pyran-2-one (from Example 33; 1.2 g, 2.25 mmol) was dissolved in $CH_2Cl_2$ (25 mL) and treated consecutively with $NEt_3$ (0.72 mL, 5.2 mmol) and methane sulfonyl chloride (0.4 mL, 5.2 mmol). The reaction was stirred overnight at room temperature then poured onto 1N HCl. The product was partitioned between $CH_2Cl_2$ and $H_2O$. The organic layer was dried (MgSO₄) and concentrated. The residue was dissolved in DMF (2 mL) and treated with 0.5 mL of ammonium hydroxide followed by stirring for 3 hours at room temperature. The product was partitioned between EtOAc and 1N HCL. The organic layer was dried (MgSO₄) and concentrated. Purification by silica gel chromatography, eluting with MeOH:hexane:CH₂Cl₂ (1:50:50) gave a solid, m.p. 85–87° C.

The title compound was prepared by combining methanesulfonic acid 2-{4-[5-(2-tert-butyl-5-methyl-phenylsulfanyl)-4-hydroxy-6-oxo-2-phenethyl-3,6-dihydro-2H-pyran-2-yl]-phenoxy} -ethyl ester (0.07 g, 0.1 15 mmol) from the previous paragraph, K₂CO₃ (0.08 g, 0.57 mmol), and morpholine (0.15 mL, 1.72 mmol) in DMF (2 mL). The reaction was stirred overnight at room temperature then combined with H₂O and acidified to pH 6.0 with 1N HCl. The product was extracted with EtOAc, dried (MgSO₄) and concentrated. Purification by silica gel chromatography, eluting with MeOH:CH₂Cl₂:hexane (1:50:50) gave the title compound, m.p. 140–150° C. ¹H NMR (CDCl₃) δ 1.48 (s, 9 H), 1.80 (s, 3 H), 2.17–2.29 (m, 3 H), 2.38 (m, 1 H), 2.63 (m, 4 H), 2.84 (m, 2 H), 3.21 (dd, 2 H), 3.74 (m, 4 H), 4.00 (m, 2 H), 6.15 (s, 1 H), 6.78 (m, 2 H), 7.05 (d, 2 H), 7.10–7.22 (m, 5 H), 7.32 (d, 2 H).

Example 35

3-(2-tert-Butyl-5-methyl-phenylsulfanyl)-4-hydroxy-6-phenethyl-6-[4-(2-piperazin-1-yl-ethoxy)-phenyl]-5,6-dihydro-pyran-2-one The title compound was prepared as described in General Method 9 using 2.0 g (3.8 mmol) of 4-(2-{[4-hydroxy-6-oxo-2-phenethyl-3,6-dihydro-2H-pyran-2-yl]-phenoxy}ethyl)-piperazine-1-carboxylic acid tert-butyl ester prepared in Example WW, 1.41 g (4.22 mmol) of 2-tert-butyl-5-methylphenyl-p-toluenethiosulfonate (prepared in Example LLLL), 2.1 g (15.2 mmol) of K₂CO₃, and 15 mL of DMF. The solution was stirred 3 days at room temperature, then pumped to dryness under vacuum. The residue was combined with aqueous acetic acid, filtered and washed with EtOAc to give 4-(2-{4-[5-(2-tert-butyl-5-methyl-phenylsulfanyl)-4-hydroxy-6-oxo-2-phenethyl-3,6-dihydro-2H-pyran-2-yl]-phenoxy}-ethyl)-piperazine-1-carboxylic acid tert-butyl ester, m.p. 194–195° C.

The intermediate prepared in the previous paragraph (2.15 g, 3.07 mmol) was dissolved in CH₂Cl₂ (200 mL), cooled in an ice bath, and treated with a steady stream of gaseous HCl for 10 minutes. The reaction was warmed to room temperature over 2 hours and concentrated. The residue was triturated from CHCl₃ and hexane to give the title compound, m.p. 175° C. ¹H NMR (DMSO-d₆) δ 1.43 (s, 9 H), 1.86 (s, 3 H), 2.16–2.35 (m, 2 H), 2.55 (m, 1 H), 3.40–3.61 (m, 12 H), 4.41 (bs, 2 H), 6.21 (s, 1 H), 6.74 (d, 1 H), 7.06–7.27 (m, 8 H), 7.40 (d, 2 H), 9.79 (bs, 1 H), 12.18 (bs, 1 H).

Example 36

3-(2-tert-Butyl-4-hydroxymethyl-5-methyl-phenylsulfanyl)-4-hydroxy-6-[2-(4-hydroxy-phenyl)-ethyl]-6-phenyl-5,6-dihydro-pyran-2-one The title compound was prepared as described in General Method 9 using 4-hydroxy-6-[2-(4-hydroxy-phenyl)-ethyl]-6-phenyl-5,6-dihydro-pyran-2-one (0.2 g, 0.64 mmol) from Example TT, toluene-4-thiosulfonic acid S-(2-tert-butyl-4-hydroxymethyl-5-methyl-phenyl) ester (prepared in Example FFF; 0.26 g, 0.71 mmol), K₂CO₃ (0.35 g, 2.5 mmol), and DMF (3 mL). The solution was stirred overnight at room temperature and then poured into 1N HCl and EtOAc. The organic phase was dried (MgSO₄), and concentrated. Purification by silica gel chromatography, eluting with MeOH:CH₂Cl₂:hexane (5:80:20 to 5:95:0) gave the title compound, m.p. 196–199° C. ¹H NMR (DMSO-d₆) δ 1.44 (s, 9 H), 1.76 (s, 3 H), 2.08–2.21 (m, 3 H), 2.42 (m, 1 H), 3.41 (dd, 2 H), 4.32 (s, 2 H), 4.91 (br s, 1 H), 6.16 (s, 1 H), 6.61 (d, 2 H), 6.86 (d, 2 H), 7.21 (s, 1 H), 7.34–7.46 (m, 5 H), 9.14 (s, 1 H), 12.15 (bs, 1 H).

Example 37

3-(2-tert-Butyl-4-hydroxymethyl-5-methyl-phenylsulfanyl)-4-hydroxy-6-[2-(3-hydroxy-phenyl)-ethyl]-6-phenyl-5,6-dihydro-pyran-2-one The title compound was prepared as described in General Method 9 using 4-hydroxy-6-[2-(3-hydroxy-phenyl)-ethyl]-6-phenyl-5,6-dihydro-pyran-2-one (0.155 g, 0.5 mmol) from Example UU, toluene-4-thiosulfonic acid S-(2-tert-butyl-4-hydroxymethyl-5-methyl-phenyl) ester (prepared in Example FFF; 0.2 g, 0.55 mmol), K₂CO₃ (0.27 g, 1.95 mmol), and DMF (3 mL). The solution was stirred overnight at room temperature, concentrated and the residue partitioned between 1N HCl and EtOAc. The organic phase was dried (MgSO₄), and concentrated. Purification by silica gel chromatography, eluting with MeOH:CHCl₃:hexane (5:90:10 to 10:90:10) gave the title compound, m.p. 132–135° C. ¹H NMR (DMSO-d₆) δ 1.45 (s, 9 H), 1.76 (s, 3 H), 2.08–2.24 (m, 3 H), 2.48 (m, 1 H), 3.41 (dd, 2 H), 4.32 (s, 2 H), 4.91 (br s, 1 H), 6.17 (s, 1 H), 6.46–6.55 (m, 3 H), 7.02 (t, 1 H), 7.22 (s, 1 H), 7.35–7.46 (m, 5 H), 9.23 (s, 1 H), 12.15 (bs, 1 H).

Example 38

(S)-3-(2-tert-Butyl-4-hydroxymethyl-5-methyl-phenylsulfanyl)-4-hydroxy-6-[ 2-(4-hydroxy-phenyl)-ethyl]-6-isopropyl-5,6-dihydro-pyran-2-one (+)

The title compound was prepared as described in General Method 9 using (S)-4-hydroxy-6-[2-(4-hydroxy-phenyl)-ethyl]-6-isopropyl-5,6-dihydro-pyran-2-one (0.3 g, 1.09 mmol) from Example WWWW, toluene-4-thiosulfonic acid S-(2-tert-butyl-4-hydroxymethyl-5-methyl-phenyl) ester (0.43 g, 1.19 mmol) from Example FFF, K₂CO₃ (0.6 g, 4.34 mmol) and DMF (5 mL). The solution was stirred overnight at room temperature and then stripped to dryness. The product was partitioned between 1N NaOH and Et₂O. The aqueous layer was acidified to pH 4–5 with 1N HCl and extracted with ethyl acetate. The organic phase was dried (MgSO₄), and concentrated. Purification by trituration with Et₂O gave the title compound (m.p. 205–207° C.). ¹H-NMR (DMSO-d₆) δ 0.92 (d, 3 H), 0.96 (d, 3 H), 1.49 (s, 9 H), 1.89 (s, 3 H), 1.92–2.0 (m, 2 H), 2.2 (m, 1H), 2.35–2.6 (m, 2 H), 2.75 (d of ABX q, 1 H), 2.97 (d, ABX q, 1 H), 4.36 (s, 2 H), 4.94 (br s, 1 H), 6.65 (d, 2 H), 6.69 (s, 1 H), 6.96 (d, 2 H), 7.28 (s, 1 H), 9.15 (s, 1 H), 11.97 (br s, 1 H).

Example 39

3-(2-tert-Butyl-4-hydroxymethyl-5-methyl-phenylsulfanyl)-6-cyclopentyl-4-hydroxy-6-[2-(3-hydroxy-phenyl)-ethyl]-5,6-dihydro-pyran-2-one The title compound was prepared as described in General Method 9 using 6-cyclopentyl-4-hydroxy-6-[2-(3-hydroxy-phenyl)-ethyl]-5,6-dihydro-pyran-2-one (0.26 g, 0.9 mmol) from Example AAAAA, toluene-4-thiosulfonic acid S-(2-tert-butyl-4-hydroxymethyl-5-methyl-phenyl) ester (prepared in Example FFF; 0.35 g, 1.0 mmol), 0.54 g (3.9 mmol) of K₂CO₃ in DMF (10 mL). The product was purified by column chromatography on silica gel eluting with EtOAc:hexane:CH₂Cl₂ (1:1:1) to afford the product in 81% yield as a white solid (m.p. 172–174° C.). ¹H-NMR (DMSO-d₆) δ 1.47 (s, 9 H), 1.4–1.7 (m, 8 H, 1.9 (s, 3 H), 1.95–2.1 (m, 2 H), 2.35 (t, 1 H), 2.5–2.6 (m, 2 H, partially obscured by DMSO), 2.7 (q, 2 H), 4.35 (s, 2 H), 4.95 (bs, 1 H), 6.55 (t, 3 H), 6.65 (s, 1 H), 7.05 (t, 1 H), 7.25 (s, 1 H), 9.25 (s, 1 H).

Example 40

(S) 3-(2-tert-Butyl-4-hydroxymethyl-5-methyl-phenylsulfanyl)-6-cyclopentyl-4-hydroxy-6-[2-(3-hydroxy-phenyl)-ethyl]-5,6-dihydro-pyran-2-one (+)

The title compound was prepared as described in General Method 9 using (S)-6-cyclopentyl-4-hydroxy-6-[2-(3-hydroxy-phenyl)-ethyl]-5,6-dihydro-pyran-2-one (0.44 g, 1.47 mmol) from Example FFFFF, toluene-4-thiosulfonic acid S-(2-tert-butyl-4-hydroxymethyl-5-methyl-phenyl) ester (0.59 g, 1.62 mmol) from Example FFF, potassium carbonate (0.81 g, 5.86 mmol) and DMF (5 mL). The solution was stirred overnight at room temperature and stripped to dryness. The product was partitioned between 1N NaOH and Et₂O. The aqueous layer was acidified to pH 4–5 with 1N HCl and extracted with EtOAc. The organic phase was dried (MgSO₄), and concentrated. Purification by trituration with Et₂O gave the title compound, m.p. 128–132° C. ¹H-NMR (DMSO-d₆) δ 1.47 (s, 9 H), 1.4–1.7 (m, 8 H), 1.9 (s, 3 H), 1.95–2.1 (m, 2 H), 2.35 (t, 1 H), 2.5–2.6 (m, 2 H, partially obscured by DMSO), 2.7 (q, 2 H), 3.35 (bs, 1 H), 4.35 (s, 2 H), 4.95 (bs, 1 H), 6.55 (t, 3 H), 6.65 (s, 1 H), 7.05 (t, 1 H), 7.25 (s, 1 H), 9.25 (s, 1 H).

Example 41

(S)-(6-[2-(4-Amino-phenyl)-ethyl]-3-(2-tert-butyl-4-hydroxymethyl-5-methyl-phenylsulfanyl)-4-hydroxy-6-isopropyl-5,6-dihydro-pyran-2-one To a round bottom flask was charged (S)-((4-{2-[5-(2-tert-butyl-4-hydroxymethyl-5-methyl-phenylsulfanyl)-4-hydroxy-2-isopropyl-6-oxo-3,6-dihydro-2H-pyran-2-yl]-ethyl}-phenyl)-carbamic acid tert-butyl ester (1.71 g, 2.93 mmol) from Example OOOO and CH₂Cl₂ (5 mL) to form a clear solution. To this was added a mixture of TFA (5.0 mL) and H₂O (1.0 mL). The reaction was allowed to stir for 2 hours at room temperature. The reaction was quenched with 1.0N NaOH until the pH was brought to 13.0. The aqueous layer was extracted with Et₂O and the aqueous layer was acidified to pH 6.5 with saturated NH₄HPO₄, resulting in the formation of a precipitate. The precipitate was partitioned into EtOAc (3×). The organics were combined, washed with brine, and dried with MgSO₄. The solvent was removed under reduced pressure and the residue submitted to flash chromatography (silica gel, 95% CH₂Cl₂ 5% EtOH). The fractions were combined and the solvent removed under reduced pressure. The residue was taken up in a small amount of CH₂Cl₂ and then triturated with hexane. The resulting solid was filtered and dried overnight in high vacuum oven at 50° C. to yield the title compound. ¹H NMR (DMSO-d₆) δ 0.93 (dd, 6 H), 1.47 (s, 9 H), 1.91 (s, 3 H), 1.92–1.97 (m, 2 H), 2.16–2.20 (m, 1 H), 2.41–2.47 (m, 2 H), 2.72 (d of abq, 1 H), 2.90 (d of abq, 1 H), 4.34 (s, 2 H), 6.49 (d, 2 H), 6.69 (s, 1 H), 6.80 (d, 2 H), 7.26 (s, 1 H).

Example 42

(S) 3-(4-Amino-2-tert-butyl-5-methyl-phenylsulfanyl)-4-hydroxy-6-[2-(4-hydroxy-phenyl)-ethyl]-6-isopropyl-5,6-dihydro-pyran-2-one The title compound was prepared as described in General Method 9 using 3.0 g (10.86 mmol) of (S)4-hydroxy-6-[2-(4-hydroxy-phenyl)-ethyl]-6-isopropyl-5,6-dihydro-pyran-2-one (prepared in Example WWWW), 3.98 g (11.40 mmol) of toluene-4-thiosulfonic acid S-(4-amino-2-tert-butyl-5-methyl-phenyl) ester (prepared in Example HHHH), 4.50 g of anhydrous K₂CO₃ and 54 mL DMF. The reaction was stirred at room temperature overnight. The reaction was quenched with saturated NH₄Cl solution and extracted with EtOAc. The organic phase was dried over MgSO₄ and concentrated. The crude material was purified by flash silica gel chromatography, eluting with EtOAc, to give the title compound, m.p. 147–149° C. (dec.). ¹H-NMR (DMSO-d₆) δ 0.89 (d, 3 H), 0.93 (d, 3 H), 1.42 (s, 9 H), 1.71 (s, 3 H), 1.85–1.93 (m, 2 H), 2.15 (m, 1 H), 2.41–2.50 (m, 2 H, partially obscured by DMSO), 2.67 (d of ABX q, 1 H), 2.89 (d of ABX q, 1 H), 6.55 (s, 1 EH), 6.60 (s, 1 H), 6.64 (d, 2H), 6.93 (d, 2H), 9.13 (br s, 1 H).

Table 1 below recites Examples 1–42 as described above and additional Examples 43–105 which were prepared by the procedures taught in Examples 1–42 and in Example 106 below.

TABLE 1

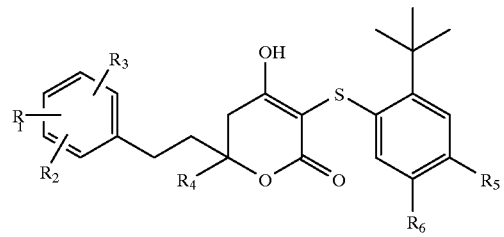

| Example # | R₁ | R₂ | R₄ | R₅ | R₆ | Melting or Decomp Pt ° C. | Mass Spec ion (Rel %) |
|---|---|---|---|---|---|---|---|
| 1 | 4-OH | —H | —CH₃ | —OCH₂CH₂OH | —Me | 203—205 | |
| 2 | 4-OH | —H | —CH(CH₃)₂ | —CH₂OH | —Me | 116–118 | |
| 3 | 4-OH | —H | —CH₃ | —OSO₂NHEt | —Me | 102–104 | |
| 4 | 4-OH | —H | —CH₃ | —OSO₂N(Me)₂ | —Me | 181–183 | |
| 5 | 4-OH | —H | —CH(CH₃)₂ | —OCH₂CH₂OH | —Me | 90–92 | |
| 6 | 4-OH | —H | —CH₃ | —OSO₂NHt-Bu | —Me | 108–110 | |
| 7 | 4-OH | —H | —CH₂(CH₂)₂CH₃ | —CH₂OH | —Me | 128–130 | |
| 8 | 4-OH | —H | -c-hexyl | —OSO₂NHEt | —Me | 88 | |

TABLE 1-continued

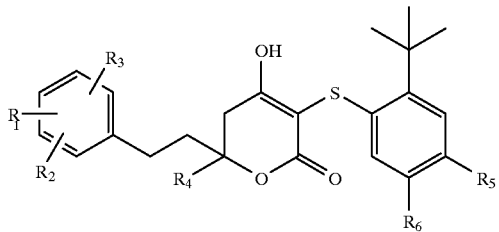

| Example # | R₁ | R₂ | R₄ | R₅ | R₆ | Melting or Decomp Pt ° C. | Mass Spec ion (Rel %) |
|---|---|---|---|---|---|---|---|
| 9 | 4-OH | —H | -c-hexyl | —CH₂OH | —Me | 138–139 | |
| 10 | 4-OH | —H | -c-hexyl | —OH | —Me | 100–103 | |
| 11 | 4-OH | —H | —CH₃ | —NH₂ | —Me | 158–168 | |
| 12 | 4-OH | —H | —CH₂CH₂—C₆H₄-4-OH | —NHSO₂N(Me)₂ | —Me | | 655(100) |
| 13 | 4-OH | —H | —CH₃ | —NHSO₂—C₆H₄-4-CN | —Me | 153 | |
| 14 | 4-OH | —H | —CH₂CH₂—C₆H₄-4-OH | —CH₂OH | —Me | 192–194 | |
| 15 | 4-NH₂ | —H | -Ph | —CH₂OH | —Me | 218–221 | |
| 16 | 4-NH₂ | —H | —CH₂CH₂—C₆H₄-4-NH₂ | —CH₂OH | —Me | 144–146 | |
| 17* | —H | —H | -Ph | —CH₂OH | —Me | 186–187 | |
| 18 | 4-OH | —H | —CH₂CH₂—C₆H₄-4-OH | —OCH₂CH₂OH | —Me | 106–107 | |
| 19 | 4-OH | —H | —CH₂CH₂—C₆H₄-4-OH | —OCH₂CO₂Et | —Me | 162–163 | |
| 20 | 4-OH | —H | —CH₂CH₂—C₆H₄-4-OH | —NH₂ | —Me | 140–145 | |
| 21 | 3-OH | —H | —CH₂CH₂—C₆H₄-3-OH | —CH₂OH | —Me | 92–94 | |
| 22 | 3-OH | —H | —CH₂CH₂—C₆H₄-3-OH | —OSO₂N(Me)₂ | —Me | | 656(100) |
| 23 | 4-OH, 3-OCH₃ | —H | —CH₂CH₂—C₆H₃-3-OMe—4-OH | —OCH₂CH₂OH | —Me | 76–82 | |
| 24 | —H | —H | —C₆H₄-4-OCH₂CH₂OH | —OH | —Me | 168–170 | |
| 25 | —H | —H | —C₆H₄-4-OCH₂CH₂OH | —OCH₂CH₂OH | —Me | >190 | |
| 26 | —H | —H | —C₆H₄-4-OCH₂CH₂-1-piperazine | —OSO₂N(Me)₂ | —Me | 181 | |
| 27 | 4-OH | —H | —CH₂CH₂—C₆H₄-4-OH | —OSO₂N(Me)₂ | —Me | 139 | |
| 28 | 4-OH | —H | —CH₂CH₂—C₆H₄-4-OH | —OSO₂NHEt | —Me | 130 | |
| 29 | 4-NH₂ | —H | —CH₂CH₂—C₆H₄-4-NH₂ | —OSO₂NHEt | —Me | 194 | |
| 30 | 4-OH | —H | —CH₂CH₂—C₆H₄-4-OH | —OSO₂-1-piperazine-4-Me | —Me | 150 | |
| 31 | 4-OH | —H | —CH₃ | —OSO₂-1-piperazine-4-Me | —Me | 240 | |
| 32 | 4-OH | —H | —CH₃ | —OSO₂-4-imidazole-1-Me | —Me | 160 | |
| 33 | —H | —H | —C₆H₄-4-OCH₂CH₂OH | —H | —Me | 154–156 | |
| 34 | —H | —H | —C₆H₄-4-OCH₂CH₂-1-morpholine | —H | —Me | 140–150 | |
| 35 | —H | —H | —C₆H₄-4-OCH₂CH₂-1-piperazine | —H | —Me | 175 | |
| 36 | 4-OH | —H | -Ph | —CH₂OH | —Me | 196–199 | |
| 37 | 3-OH | —H | -Ph | —CH₂OH | —Me | 132–135 | |
| 38* | 4-OH | —H | —CH(CH₃)₂ | —CH₂OH | —Me | 205–207 | |
| 39 | 3-OH | —H | -c-pentyl | —CH₂OH | —Me | 172–174 | |
| 40* | 3-OH | —H | -c-pentyl | —CH₂OH | —Me | 128–132 | |
| 41* | 4-NH₂ | —H | —CH(CH₃)₂ | —CH₂OH | —Me | | 482(70) 306(100) |
| 42* | 4-OH | —H | —CH(CH₃)₂ | —NH₂ | —Me | 147–149 | |
| 43 | 4-OH | —H | —CH₃ | —OSO₂NH₂ | —Me | 127 | |
| 44 | 4-OH | —H | —CH₂CH₃ | —CH₂OH | —Me | 96–98 | |
| 45 | 4-OH | —H | —CH₃ | —NH₂SO₂N(Me)₂ | —Me | 203 | |
| 46 | —H | —H | —C₆H₄-4-OCH₂CH₂OH | —OSO₂-1-piperazine-4-Me | —Me | 175 | |
| 47 | 4-OH | —H | —CH₃ | —OSO₂-1-piperazine-4-Me | —Me | 240 | |
| 48 | 4-OH | 3-OMe | —C₆H₄-4-OCH₂CH₂OH | —OSO₂NHEt | —Me | 140 | |
| 49 | 4-OH | —H | —CH₃ | —NHSO₂Ph | —Me | | 582(100) |
| 50 | 3-NH₂ | —H | —C₆H₄-4-OCH₂CH₂-1-piperazine | —CH₂OH | —Me | >280 | |
| 51 | 4-OH | —H | —CH₃ | —OSO₂C₆H₄-4-Me | —Me | 205 | |
| 52 | 4-OH | —H | -c-hexyl | —OSO₂-4-imidazole-1-Me | —Me | 127–141 | |
| 53 | 4-OH | —H | —CH(CH₃)₂ | —NHCOMe | —Me | 126–145 | |
| 54 | 3-OH | —H | -c-hexyl | —CH₂OH | —Me | | 524(80) |
| 55 | 3-OH | —H | c-hexyl | —OSO₂NHEt | —Me | | 618(100) |
| 56 | 4-NH₂ | 3-Cl | -c-hexyl | —CH₂OH | —Me | 133–135 | |
| 57 | 4-NH₂ | —H | -c-hexyl | —CH₂OH | —Me | 214–216 | |
| 58 | 4-OH | —H | —CH(CH₃)₂ | —NHCOPh | —Me | 104–120 | |
| 59 | 4-OH | —H | -c-propyl | —CH₂OH | —Me | 152–154 | |

TABLE 1-continued

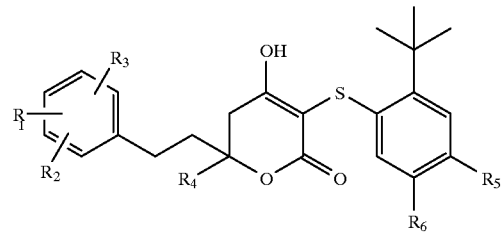

| Example # | R$_1$ | R$_2$ | R$_4$ | R$_5$ | R$_6$ | Melting or Decomp Pt ° C. | Mass Spec ion (Rel %) |
|---|---|---|---|---|---|---|---|
| 60 | 4-OH | —H | —CH$_2$CH(CH$_3$)$_2$ | —CH$_2$OH | —Me | 108–110 | |
| 61 | | 3,4-OCH$_2$O— | —CH(CH$_3$)$_2$ | —CH$_2$OH | —Me | 90–92 | |
| 62 | 4-OH | —H | -c-pentyl | —CH$_2$OH | —Me | 117–119 | |
| 63 | 4-OH | —H | —CH(CH$_3$)$_2$ | —OSO$_2$NHEt | —Me | 97–99 | |
| 64 | 4-NH$_2$ | —H | —CH(CH$_3$)$_2$ | —OSO$_2$NHEt | —Me | 185–188 | |
| 65 | 4-OH | —H | -c-hexyl | —OSO$_2$NHMe | —Me | >200 | |
| 66 | 4-OH | —H | —CH(CH$_3$)$_2$ | —OSO$_2$NHMe | —Me | >200 | |
| 67 | 4-OH | —H | —CH(CH$_3$)$_2$ | —OSO$_2$-1-piperazine-4-Me | —Me | 235 | |
| 68 | 4-OH | —H | —CH$_3$ | —NHCO—C$_6$H$_4$-4-CN | —Me | | 571(100) |
| 69 | 4-OH | —H | 4-piperidine-1-CO$_2$—t-Bu | —CH$_2$OH | —Me | 129–135 | |
| 70 | 4-NH$_2$ | —H | -c-propyl | —OSO$_2$NHEt | —Me | 168–171 | |
| 71 | 4-OH | —H | —CH$_3$ | —NHSO$_2$—C$_6$H$_4$-4-F | —Me | | 600(100) |
| 72 | 4-NH$_2$ | 2-CH$_3$ | -c-hexyl | —CH$_2$OH | —Me | 140–150 | |
| 73 | 4-OH | —H | -c-propyl | —NH$_2$ | —Me | 126–127 | |
| 74 | 4-OH | —H | —CH$_2$(CH$_2$)$_2$CH$_3$ | —CH$_2$OH | —Me | 127–129 | |
| 75 | 4-OH | —H | —CH(CH$_3$)$_2$ | —OCH$_2$CONH$_2$ | —Me | >180 | |
| 76 | 4-OH | —H | —CH(CH$_3$)$_2$ | —NHSO$_2$—C$_6$H$_4$-4-Cl | —Me | 214–218 | |
| 77 | 4-OH | —H | —CH(CH$_3$)$_2$ | —NHSO$_2$-2-thiophene | —Me | 207–212 | |
| 78 | 4-OH | —H | —CH$_3$ | —NHCO-3-pyridine | —Me | 231–233 | |
| 79 | 4-OH | —H | —CH(CH$_3$)$_2$ | —NHCO-2-pyridine | —Me | 143–145 | |
| 80 | 4-OH | —H | —CH(CH$_3$)$_2$ | —NHSO$_2$—C$_6$H$_4$-4-CF$_3$ | —Me | 227–229 | |
| 81 | 3-OH | —H | -c-propyl | —OCH$_2$CH$_2$OH | —Me | | 513(100) |
| 82 | 4-OH | —H | —CH(CH$_3$)$_2$ | —NHSO$_2$N(Me) | —Me | 187–189 | |
| 83 | 4-OH | —H | —CH(CH$_3$)$_2$ | —NHCS-I-piperazine | —Me | 187–189 | |
| 84 | | 3-,4-OCH$_2$O— | —CH(CH$_3$)$_2$ | —OSO$_2$NHEt | —Me | 87–89 | |
| 85 | 3-OH | H | -c-pentyl | —OSO$_2$NHEt | —Me | 69–72 | |
| 86 | 4-NH$_2$ | —H | —CH(CH$_3$)$_2$ | —OSO$_2$-C$_6$H$_4$-4-CN | —Me | | 635(100) |
| 87 | 4-OH | —H | —C$_6$H$_4$-4-F | —CH$_2$OH | —Me | | 579(100) |
| 88 | 4-OH | —H | —CH(CH$_3$)$_2$ | —OSO$_2$Me | —Me | >180 | |
| 89 | 4-OH | —H | -4-piperidine-1-COCH$_3$ | —OSO$_2$NHEt | —Me | 140–146 | |
| 90 | 4-OH | —H | —CH(CH$_3$)$_2$ | —OSO$_2$-1-morpholine | —Me | >180 | |
| 91 | 4-OH | —H | -4-pyran | —OSO$_2$NHEt | —Me | 220–223 | |
| 92 | 4-OH | —H | —C$_6$H$_4$-4-OCH$_3$ | —CH$_2$OH | —Me | | 549(40) |
| 93 | 4-OH | —H | —CH(CH$_3$)$_2$ | —N(Me)$_2$ | —Me | 158–160 | |
| 94 | 4-OH | 2-CH$_3$ | —CH(CH$_3$)$_2$ | —CH$_2$OH | —Me | 194–196 | |
| 95 | 4-OH | —H | —CH(CH$_3$)$_2$ | —OSO$_2$CH$_2$CH$_2$-1-morpholine | —Me | >180 | |
| 96 | 4-OH | —H | —CH(CH$_3$)$_2$ | —OCON(Me)$_2$ | —Me | >180 | |
| 97 | 4-OH | —H | —CH(CH$_3$)$_2$ | —CH$_2$OH | —Et | 156–158 | |
| 98 | 4-OH | —H | -c-butyl | —CH$_2$OH | —Me | 99–102 | |
| 99 | 4-OH | —H | —CH(CH$_3$)$_2$ | —NHSO$_2$—C$_6$H$_4$-3-CN | —Me | | 635(100) |
| 100 | 4-OH | 3-CH$_3$ | —CH(CH$_3$)$_2$ | —CH$_2$OH | —Me | 136–138 | |
| 101 | 4-OH | —H | -c-pentyl | —CONH$_2$ | —Me | 142–146 | |
| 102 | 4-OH | 2-CH$_2$CH$_3$ | —CH(CH$_3$)$_2$ | —CH$_2$OH | —Me | 95–106 | |
| 103 | 4-NH$_2$ | 3-F | —CH(CH$_3$)$_2$ | —CH$_2$OH | —Me | 96–100 | |
| 104 | 3-OH | 2-CH$_3$ | —CH(CH$_3$)$_2$ | —NH$_2$ | —Me | | 483(48) |
| 105 | 4-OH | —H | —CH(CH$_3$)$_2$ | —CH$_2$CH$_2$OH | —Me | | 497(100) |
| 106 | 4-NH$_2$ | —H | —CH(CH$_3$)$_2$ | —CH$_2$OH | —Me | 139–141 | |

*Single enantiomer1

Example 106

6-[2-(4-Amino-phenyl)-ethyl]-3-(2-tert-butyl-4-hydroxymethyl-5-methyl-phenylsulfanyl)-4-hydroxy-6-isopropyl-5,6-dihydro-pyran-2-one A solution of {4-[2-(4-hydroxy-2-isopropyl-6-oxo-3,6-dihydro-2H-pyran-2-yl)-ethyl]-phenyl}-carbamic acid 1,1-dimethylethyl ester (0.26 g, 0.69 mmol; prepared in Example QQQQQ) in CH$_2$Cl$_2$ was cooled to 5° C. and treated with a steady stream of gaseous HCl for 5 minutes. The solution was concentrated, and the residue was triturated with ether. The crude material was dissolved in DMF (5 mL) and treated with 1.0 g (7.0 mmol) of K$_2$CO$_3$ and 0.25 g (0.69 mmol) of toluene-4-thiosulfonic acid S-(2-tert-butyl-4-hydroxymethyl-5-methyl-phenyl) ester (prepared in Example FFF). The reaction mixture was stirred overnight at room temperature. Water (30 mL) and EtOAc (50 mL) were added; the mixture was cooled in an ice bath and acidified to pH 5.5 with AcOH. The organic layer was separated, washed with brine, dried (MgSO$_4$), and concentrated. The product was chromatographed on silica gel, eluting with CHCl$_3$:MeOH (90:10) to give the title compound, m.p. 139–141° C. $^1$H NMR (DMSO-d$_6$) δ 0.88 (m, 6 H), 1.42 (s, 9 H), 1.87 (m, 5 H), 2.14 (m, 1 H), 2.40 (m, partially obscured by DMSO, 2 H), 2.66 (d of ABXq, 1 H), 2.88 (d, of ABXq, 1 H), 4.30 (s, 2 H), 4.90 (br s, 1 H), 6.43 (d, 2 H), 6.64 (s, 1 H), 6.77 (d, 2 H), 7.20 (s, 1 H).

The compounds of the present invention were evaluated for their in vitro inhibition of HIV-1 protease and for their antiviral efficacy in HIV infected lymphocytes.

HIV Protease Assay:

Materials

Recombinant HIV-1 protease (>96% purity) and HIV protease substrate III (the undecapeptide H-His-Lys-Ala-Arg-Val-Leu-Nph-Glu-Ala-Nle-Ser-NH$_2$, >97% purity) were purchased from Bachem Bioscience Inc. (King of Prussia, Pa.).

Method

The methods employed follow the procedures of Tummino, et al. (*Archives of Biochemistry and Biophysics* 1995, 316, 523). For determination of IC$_{50}$ values, HIV-1 protease, 6.0 nM final concentration, was added to a solution containing inhibitor, 40 μM substrate III and 1.0% Me$_2$SO in assay buffer: 80 mM MES, 160 mM NaCl, 1.0 mM EDTA 0.1 % polyethylene glycol (Mr 8000) pH 6.2 at 37° C. (total volume, 100 μl). Polyethylene glycol was used in the assay in place of glycerol since the former was reported to be a more effective stabilizing agent of the protease (Jordan, et. al. *J. Biol. Chem.* 1992, 267, 20028). The final inhibitor concentrations used were 0 (0.1, 0.2, in some experiments), 0.5, 1 2, 5, 10, 20, 50, and 100 μM. The solution was mixed, incubated for 5 minutes and the reaction quenched by addition of trifluoracetic acid, 2% final. The (leu-p-nitro-phe) bond of the substrate is cleaved by the enzyme and substrate and products separated by reverse-phase HPLC. Absorbance was measured at 220 nm, peak areas determined, and percentage conversion to product used to calculate percentage control (=[% conversion (+inhibitor)/% conversion (−inhibitor)]×100).

Cellular Infection Assay

Compounds were tested in lymphocyte derived CEM cells using the XTT cytopathic procedures and were performed at Southern Research Institute (Buckheit, et. al. *Antiviral Res.* 1993, 21, 247; see also Weislow, et al. *J. Nat. Cancer Inst.,* 1989, 81, 577). Compound concentrations were 0.32, 1, 3.2, 10, 32 and 100 μM. The EC$_{50}$ represents the concentration of agent which reduces HIV cytopathic effects 50% relative to untreated control. EC$_{95}$ represents the concentration of agent protecting the cells 95% relative to untreated control. Cellular toxicity of the agents are estimated from the TC$_{50}$ which represents the concentration of the agent which inhibits 50% of the viability of uninfected cells.

Table 2 contains the results of the HIV protease assay (IC$_{50}$) and the antiviral efficacy (EC$_{50}$, TC$_{50}$, EC$_{95}$) screening.

TABLE 2

Inhibition of HIV-Protease and Antiviral Efficacy in CEM Cell Infection Assay

| Example # | Inhib of HIV-Protease IC$_{50}$ (nM) | Antiviral Efficacy | | |
|---|---|---|---|---|
| | | EC$_{50}$ (μM) | TC$_{50}$ (μM) | EC$_{95}$ (μM) |
| Ref A | 150 | >23 | 23 | — |
| Ref B | 35 | >55 | 55 | — |
| Ref C | 70 | >28 | 28 | — |
| 1 | 6.8 | 3.4 | >100 | 18 |
| 2 | 3.6 | 0.6 | >100 | 1 |
| 3 | 2.3 | 1.5 | 66 | 12 |
| 4 | 1.6 | 2.5 | 71 | 17 |
| 5 | 2.8 | 1.5 | 66 | 3.2 |
| 6 | 3.8 | 2.3 | 56 | 8.5 |
| 7 | 4.1 | 0.9 | 63 | 3.0 |
| 8 | 4.8 | 1.4 | 67 | 5.3 |
| 9 | 2.5 | 0.5 | 75 | 1.2 |
| 10 | 2.9 | 3.1 | 73 | 8.9 |
| 11 | 13 | 3.7 | >100 | 9.1 |
| 13 | 2.1 | 5.0 | >100 | 20 |
| 14 | 1.3 | 6.3 | 69 | 24 |
| 15 | 3.1 | 3.7 | 94 | 9.4 |
| 16 | 1.6 | 1.2 | 72 | 15 |
| 17 | 3.9 | 1.9 | 60 | 7.5 |
| 20 | 2.9 | 5.0 | 65 | 9.6 |
| 21 | 2.1 | 4.8 | 66 | 9.3 |
| 22 | 9.0 | 2.3 | 66 | 8.3 |
| 23 | 3.4 | 2.0 | 61 | 7.9 |
| 26 | 5.1 | 5.1 | >100 | 9.3 |
| 28 | 1.3 | 5.5 | 67 | 9.4 |
| 29 | 1.8 | 1.2 | 66 | 2.9 |
| 30 | 5.5 | 5.0 | 66 | 9.3 |
| 31 | 7.1 | 2.3 | >100 | 8.4 |
| 35 | 6.3 | 3.5 | 84 | 8.0 |
| 36 | 1.6 | 4.7 | >100 | 20 |
| 37 | 2.5 | 6.1 | >100 | — |
| 38 | 1.0 | <0.3 | >100 | 1.0 |
| 39 | 1.9 | <0.3 | >100 | 0.6 |
| 40 | | <0.3 | >100 | <0.3 |
| 43 | 1.8 | 5.2 | 69 | 9.4 |
| 46 | 12 | 5.4 | 58 | 9.8 |
| 48 | 2.4 | 6.9 | >100 | 26 |
| 58 | 21 | 2.8 | 66 | 24 |
| 61 | 3.1 | 1.0 | 78 | 15 |
| 62 | 3.1 | 0.6 | >100 | 2.5 |
| 67 | 3.1 | 0.5 | >100 | 2.0 |
| 68 | 56 | 16 | >100 | 30 |
| 71 | 3.7 | 2.4 | 93 | 8.6 |
| 72 | 4.4 | 0.5 | 66 | 8.5 |
| 77 | 8.7 | 1.8 | >100 | 5.2 |
| 83 | 41 | 43 | >100 | 92 |
| 86 | 1.3 | 0.4 | 53 | 3.7 |
| 87 | 1.7 | 5.1 | 89 | 10 |
| 89 | 12 | 32 | >100 | 89 |
| 93 | 11 | 1.9 | 68 | 10 |
| 97 | — | 0.8 | >100 | 2.8 |
| 98 | 2.2 | 0.8 | >100 | 1.9 |
| 100 | — | 0.33 | 84 | 0.9 |

Table 2 shows that compounds of the invention display significantly greater antiviral activity than the reference examples. The reference examples, while being good HIV-protease inhibitors (IC$_{50}$'s 35–150 nM) do not contain the polar group substitutions which are present in all the compounds of the invention. The polar groups do increase HIV protease inhibition, but moreover the polar groups enhance antiviral activity with EC$_{50}$'s and EC$_{95}$'s all more potent than the reference agents. In addition, the cytotoxicity has been decreased (larger TC$_{50}$'s) relative to the reference agents. This data fully supports the invention that the appropriate placement of polar groups on the dihydropyrone protease inhibitors improves antiviral activity in the cellular infection assay.

6,046,355
73
Scheme 1
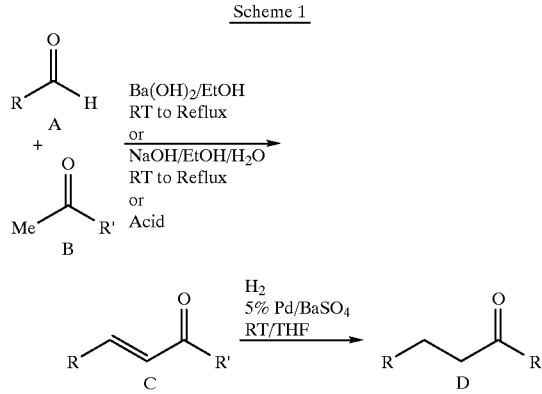
Scheme 2
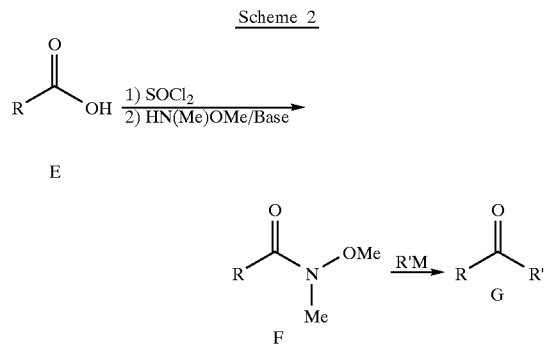
Scheme 3
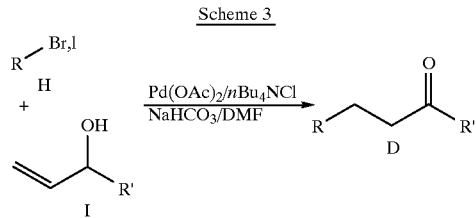
Scheme 4
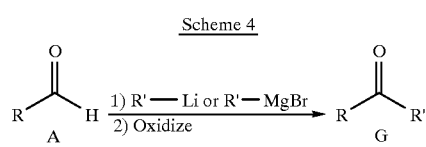
Scheme 5
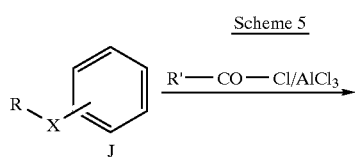
74
-continued
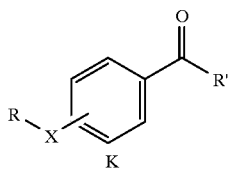
Scheme 6
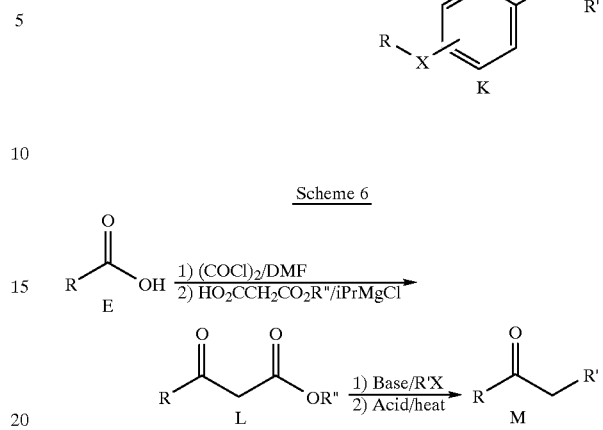
Scheme 7
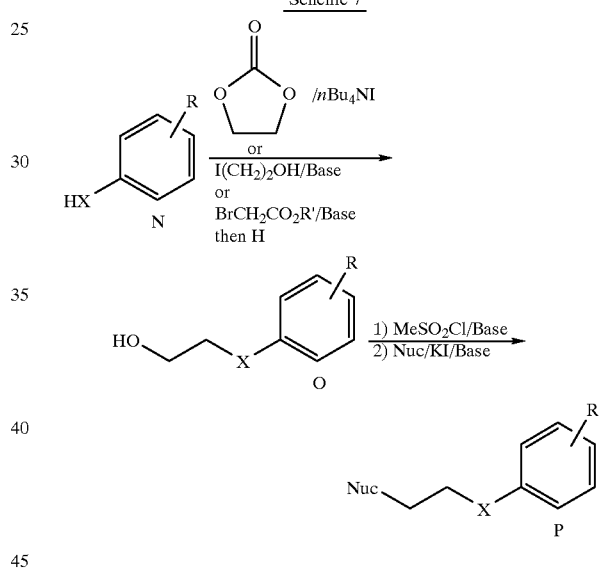
Scheme 8
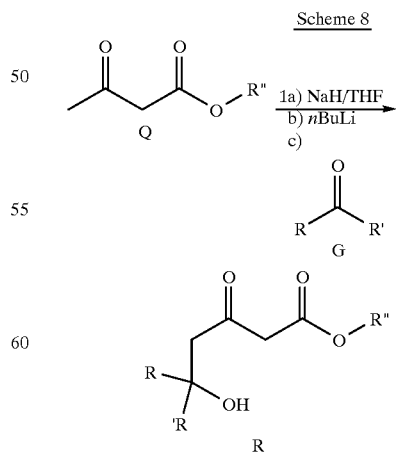

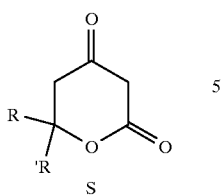
Scheme 9
wherein the * means a chiral compound
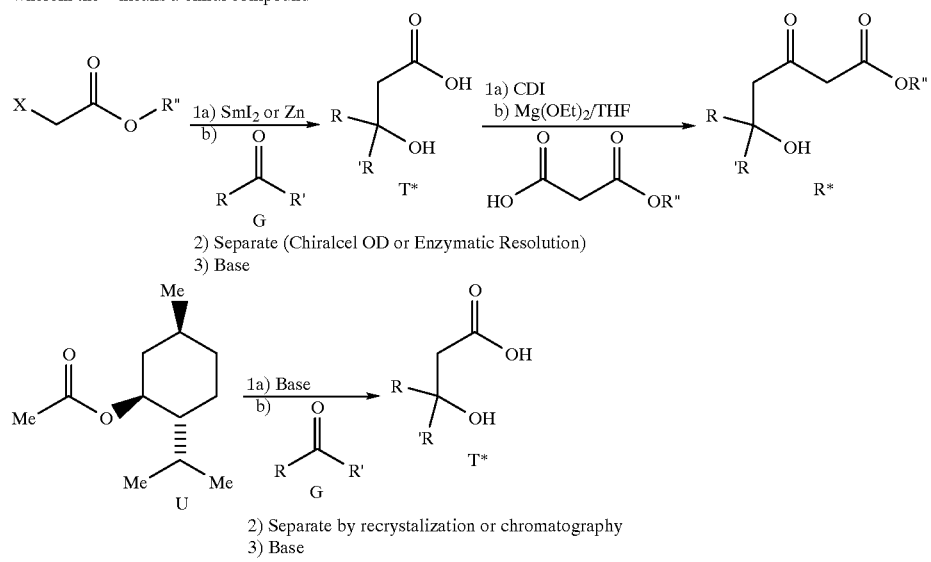
Scheme 10
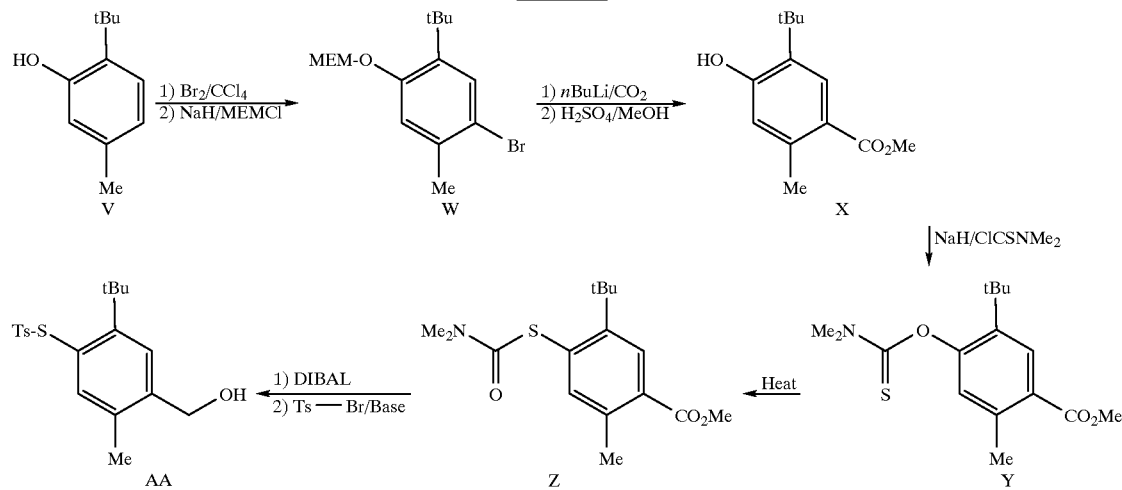

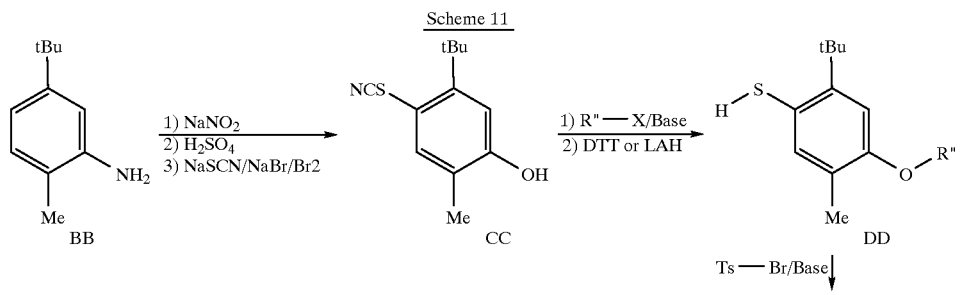
Scheme 11
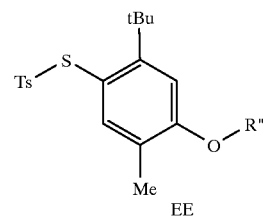
Scheme 12
Scheme 13

Scheme 14

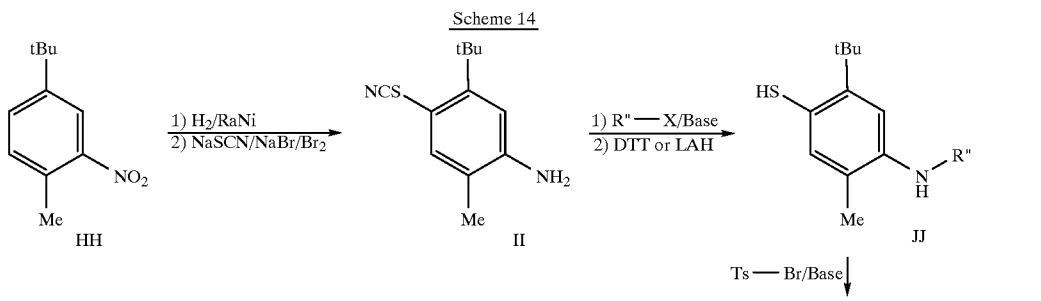

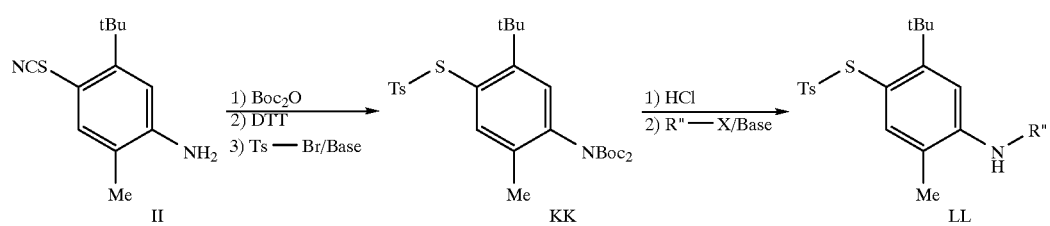

Scheme 15

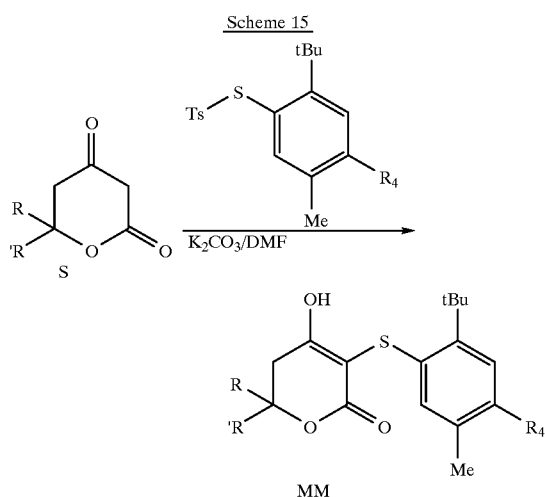

Scheme 16

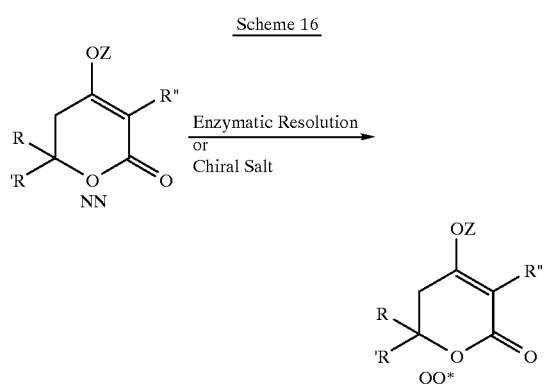

We claim:

1. A compound from the group consisting of
   Toluene-4-thiosulfonic acid S-(2-tert-butyl-4-hydroxymethyl-5-methyl-phenyl) ester;
   Toluene-4-thiosulfonic acid S-[2-tert-butyl-4-(tert-butyl-dimethyl-silanyloxy)-5-methyl-phenyl]ester;
   Toluene-4-thiosulfonic acid S-{2-tert-butyl-4-[2-(tert-butyl-dimethyl-silanyloxy)-ethoxy]-5-methyl-phenyl} ester;
   Toluene-4-thiosulfonic acid S-(2-tert-butyl-4-hydroxy-5-methyl-phenyl) ester;
   Toluene-4-thiosulfonic acid S-(2-tert-butyl-4-dimethylsulfamoyloxy-5-methyl-phenyl) ester;
   Toluene-4-thiosulfonic acid S-(2-tert-butyl-4-ethylsulfamoyloxy-5-methyl-phenyl) ester;
   4-Methyl-piperazine-1-sulfonic acid, 5-tert-butyl-2-methyl-4-(toluene-4-sulfonylsufanyl)-phenyl ester;
   1-Methyl-1H-imidazole-4-sulfonic acid, 5-tert-butyl-2-methyl-4-(toluene-4-sulfonylsufanyl)-phenyl ester;
   Toluene-4-thiosulfonic acid S-(2-tert-butyl-4-tert-butylsulfamoyloxy-5-methyl-phenyl) ester;
   Toluene 4-thiosulfonic acid S-[2-tert-butyl-4-(2-methoxymethoxy-ethoxy)-5-methyl-phenyl]ester;
   [5-(1,1-dimethylethyl)-2-methyl-4-[[(4-methylphenyl)sulfonyl)-thio]phenyl]-imidodicarbonic acid bis(1,1-dimethylethyl) ester;
   Toluene-4-thiosulfonic acid S-(4-amino-2-tert-butyl-5-methyl-phenyl) ester;
   4-methyl-benzenesulfonothioic acid[4-[[(dimethylamino)sulfonyl]-amino]-2-(1,1-dimethylethyl)-5-methylphenyl] ester;
   Toluene-4-thiosulfonic acid S-[2-tert-butyl-4-(4-cyano-benzenesulfonylamino)-5-methyl-phenyl] ester;
   2-tert-Butyl-5-methylphenyl-p-toluenethiosulfonate; and
   [5-tert-Butyl-2-methyl-4-(toluene-4-sulfonylsulfanyl)-phenoxy]-acetic acid.

* * * * *